US011591620B2

(12) United States Patent
Finley et al.

(10) Patent No.: US 11,591,620 B2
(45) Date of Patent: Feb. 28, 2023

(54) GENOME EDITING SYSTEM

(71) Applicant: CARGILL, INCORPORATED, Wayzata, MN (US)

(72) Inventors: Kenneth R. Finley, St. Bonifacius, MN (US); Briana Kozlowicz, Hopkins, MN (US); Ana Negrete-Raymond, Chanhassen, MN (US); Gregory M. Poynter, St. Paul, MN (US); Amit Vas, Minneapolis, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 119 days.

(21) Appl. No.: 16/613,948

(22) PCT Filed: May 18, 2018

(86) PCT No.: PCT/US2018/033496
§ 371 (c)(1),
(2) Date: Nov. 15, 2019

(87) PCT Pub. No.: WO2018/213771
PCT Pub. Date: Nov. 22, 2018

(65) Prior Publication Data
US 2022/0177926 A1  Jun. 9, 2022

Related U.S. Application Data

(60) Provisional application No. 62/508,040, filed on May 18, 2017.

(51) Int. Cl.
| | |
|---|---|
| C12N 9/22 | (2006.01) |
| C12N 15/90 | (2006.01) |
| A61K 38/46 | (2006.01) |
| C07K 14/39 | (2006.01) |
| C07K 19/00 | (2006.01) |
| C12N 15/10 | (2006.01) |
| C12N 15/11 | (2006.01) |

(52) U.S. Cl.
CPC .......... *C12N 15/905* (2013.01); *A61K 38/465* (2013.01); *C07K 14/39* (2013.01); *C07K 19/00* (2013.01); *C12N 9/22* (2013.01); *C12N 15/102* (2013.01); *C12N 15/111* (2013.01); *C07K 2319/85* (2013.01); *C12N 2310/20* (2017.05); *C12N 2320/32* (2013.01)

(58) Field of Classification Search
CPC ........ C12N 15/90; C12N 15/905; C12N 9/22; A61K 38/465
See application file for complete search history.

(56) References Cited

U.S. PATENT DOCUMENTS

| 5,364,780 A | 11/1994 | Hershey |
|---|---|---|
| 6,603,061 B1 | 8/2003 | Armstrong |
| 7,868,149 B2 | 1/2011 | Boukharov |
| 2009/0100536 A1 | 4/2009 | Adams |
| 2015/0211023 A1 | 7/2015 | Shiboleth |
| 2016/0289659 A1 | 10/2016 | Doudna |

FOREIGN PATENT DOCUMENTS

| WO | 1997006268 A2 | 2/1997 |
|---|---|---|
| WO | 1997006269 A1 | 2/1997 |
| WO | 2014189628 A1 | 11/2014 |

OTHER PUBLICATIONS

Aoyama et al., "A glucocorticoid-mediated transcriptional induction system in transgenic plants". The Plant Journal (1997) 11(3), 605-612.
C. Gatz, "Chemical Control of Gene Expression", Annu. Reb. Plant Physiol. Plant Mol. Biol. 1997. 48:89-108.
Choudhury, R., et al., "Engineering RNA Endonucleases with Customized Sequence Specificities", Nature Communications. 2012; vol. 3, No. 1147; pp. 1-18; DOI: 10.1038/ncomms2154.
Christiane Gatz, "Chemically inducible promoters in transgenic plants", Current Opinion in Biotechnology, 1996, 7:168-172.
Keeney, S., Giroux, C.N., and Kleckner, N. (1997) Meiosis-specific DNA double-strain breaks are catalyzed by Spo1 1, a member of a widely conserved protein family. Cell (88): 375-384.
Kenney, S. (2008) Spa11 and the formation of DNA double-strand breaks in meiosis. Genome Dyn Stab. (2): 81-123.
Morrell et al., "Crop genomics:advances and applications", Nat. Reb. Genet. Dec. 2011. 29; 13(2):85-96.
Nelles, Da, et al., "Applications of Cas9 as an RNA-Programmed RNA-Binding Protein", BioEssays. Apr. 19, 2015; vol. 37, No. 7; pp. 1-16; DOI: 10.1002/bies.201500001.
Shichino, Y., Yamashita, A., and Yamamoto, M. (2014) Meiotic long non-coding meiRNA accumulates as a dot at its genetic locus facilitated by Mmil and plays as a decoy to lure Mmil. Open Biology (4): 140022.
Sun, T., et al., "An RNA Recognition Motif-Containing Protein is Required for Plastid RNA Editing in Arabidopsis and Maize", Proceedings of the National Academy of Science of the United States of America. Mar. 4, 2013; vol. 110, No. 12; pp. E1169-E1178; DOI: 10.1073/pnas.1220162110.
Watanabe Y et al: "S. pombe mei2 encodes an RNA-binding protein essential for premeiotic DNA synthesis and meiosis I, which cooperates with a novel RNA species meiRNA", Cell, Elsevier, Amsterdam NL, vol. 78, No. 3, Aug. 12, 1994 (Aug. 12, 1994), pp. 487-498, XP024245908, ISSN:0092-8674, DOI: 10.1016/0092-8674(94)90426-X.

(Continued)

Primary Examiner — Tekchand Saidha

(57) ABSTRACT

A system for editing of a target sequence at a locus of a host cell is disclosed. The system has a nucleic acid molecule comprising a nucleic acid segment comprising a targeting RNA sequence and an RNA segment that binds a protein. The system also has a nucleic acid molecule comprising a nucleic acid segment encoding a polypeptide with endonuclease activity fused to a protein that binds the RNA segment. The system also comprises a double stranded DNA molecule comprising DNA comprising at least one nucleotide sequence that is capable of binding to the target sequence at the locus.

20 Claims, 5 Drawing Sheets

Specification includes a Sequence Listing.

(56) References Cited

OTHER PUBLICATIONS

Wood, V., et al., "The Genome Sequence of Schizosaccharomyces", Pombe. Nature. Feb. 21, 2002; vol. 415, No. 6874; pp. 871-880; DOI: 10.1038/nature724.

Y. Watanabe et al: "The S.pombe mei2 gene encoding a crucial molecule for commitment to meiosis is under the regulation of cAMP", The Embo Journal, vol. 7, No. 3,Mar. 1, 1988 *Mar. 1, 1988), pp. 761-767, XP055765395, ISSN:0261-4189, DOI: 10.1002/j.1460-2075.1988.tb02873.x.

Yamashita, A., Shichino, Y., Tanaka, H., Hiriart, E., Touat-Todeschini, L., Vavasseur, A., Ding, D.-Q., Hiraoka, Y., Verdel, A., and Yamamoto, M. (2012) Hexanucleotide motifs mediate recruitement of the RNA elimination machinery to silent meiotic genes. Open Biology (2): 120014.

SEQUENCE LISTING

<160> NUMBER OF SEQ ID NOS: 36

<210> SEQ ID NO 1
<211> LENGTH: 398
<212> TYPE: PRT
<213> ORGANISM: Saccharomyces cerevisiae

<400> SEQUENCE: 1

```
Met Ala Leu Glu Gly Leu Arg Lys Lys Tyr Lys Thr Arg Gln Glu Leu
1               5                   10                  15

Val Lys Ala Leu Thr Pro Lys Arg Arg Ser Ile His Leu Asn Ser Asn
            20                  25                  30

Gly His Ser Asn Gly Thr Pro Cys Ser Asn Ala Asp Val Leu Ala His
        35                  40                  45

Ile Lys His Phe Leu Ser Leu Ala Ala Asn Ser Leu Glu Gln His Gln
    50                  55                  60

Gln Pro Ile Ser Ile Val Phe Gln Asn Lys Lys Lys Gly Asp Thr
65                  70                  75                  80

Ser Ser Pro Asp Ile His Thr Thr Leu Asp Phe Pro Leu Asn Gly Pro
                85                  90                  95

His Leu Cys Thr His Gln Phe Lys Leu Lys Arg Cys Ala Ile Leu Leu
            100                 105                 110

Asn Leu Leu Lys Val Val Met Glu Lys Leu Pro Leu Gly Lys Asn Thr
        115                 120                 125

Thr Val Arg Asp Ile Phe Tyr Ser Asn Val Glu Leu Phe Gln Arg Gln
    130                 135                 140
```

Ala Asn Val Val Gln Trp Leu Asp Val Ile Arg Phe Asn Phe Lys Leu
145                 150                 155                 160

Ser Pro Arg Lys Ser Leu Asn Ile Ile Pro Ala Gln Lys Gly Leu Val
            165                 170                 175

Tyr Ser Pro Phe Pro Ile Asp Ile Tyr Asp Asn Ile Leu Thr Cys Glu
        180                 185                 190

Asn Glu Pro Lys Met Gln Lys Gln Thr Ile Phe Pro Gly Lys Pro Cys
    195                 200                 205

Leu Ile Pro Phe Phe Gln Asp Asp Ala Val Ile Lys Leu Gly Thr Thr
210                 215                 220

Ser Met Cys Asn Ile Val Ile Val Glu Lys Ala Val Phe Thr Lys
225                 230                 235                 240

Leu Val Asn Asn Tyr His Lys Leu Ser Thr Asn Thr Met Leu Ile Thr
                245                 250                 255

Gly Lys Gly Phe Pro Asp Phe Leu Thr Arg Leu Phe Leu Lys Lys Leu
            260                 265                 270

Glu Gln Tyr Cys Ser Lys Leu Ile Ser Asp Cys Ser Ile Phe Thr Asp
        275                 280                 285

Ala Asp Pro Tyr Gly Ile Ser Ile Ala Leu Asn Tyr Thr His Ser Asn
    290                 295                 300

Glu Arg Asn Ala Tyr Ile Cys Thr Met Ala Asn Tyr Lys Gly Ile Arg
305                 310                 315                 320

Ile Thr Gln Val Leu Ala Gln Asn Asn Glu Val His Asn Lys Ser Ile
                325                 330                 335

Gln Leu Leu Ser Leu Asn Gln Arg Asp Tyr Ser Leu Ala Lys Asn Leu
            340                 345                 350

Ile Ala Ser Leu Thr Ala Asn Ser Trp Asp Ile Ala Thr Ser Pro Leu
        355                 360                 365

Lys Asn Val Ile Ile Glu Cys Gln Arg Glu Ile Phe Phe Gln Lys Lys
    370                 375                 380

Ala Glu Met Asn Glu Ile Asp Ala Arg Ile Phe Glu Tyr Lys
385                 390                 395

<210> SEQ ID NO 2
<211> LENGTH: 397
<212> TYPE: PRT
<213> ORGANISM: Saccharomyces bayanus
<220> FEATURE:
<221> NAME/KEY: misc_feature
<222> LOCATION: (397)..(397)
<223> OTHER INFORMATION: Xaa can be any naturally occurring amino acid

<400> SEQUENCE: 2

Met Ala Leu His Arg Leu Arg Lys Lys His Arg Thr Arg Gln Glu Leu
1               5                   10                  15

Leu Lys Ala Leu Thr Pro Arg Thr Arg Ser Ile His Leu Ser Pro Asn
            20                  25                  30

Glu His Ser Asn Gly Ser Thr Ser Ser Asn Ala Glu Val Leu Ser His
        35                  40                  45

Ile Lys Gln Ile Leu Ser Leu Ala Ala Asn Ser Leu Glu Gln His Gln
    50                  55                  60

Gln Pro Ile Ser Ile Ile Phe His Asn Lys Thr Lys Gly Asn Ser Ser
65                  70                  75                  80

Gly Asn Ser Ile Thr Thr Lys Leu Asp Phe Pro Leu Asn Gly Pro His
            85                  90                  95

-continued

```
Leu Phe Thr His Gln Phe Lys Leu Lys Arg Cys Ser Ile Leu Leu Asn
                100                 105                 110

Leu Leu Lys Ile Val Met Glu Lys Leu Pro Leu Gly Gln Asn Thr Thr
        115                 120                 125

Ile Arg Asp Ile Phe Tyr Ser Asn Val Glu Leu Phe Gln Arg Gln Ala
130                 135                 140

Asn Val Val Gln Trp Leu Asp Val Ile Arg Phe Asn Phe Lys Leu Ser
145                 150                 155                 160

Pro Arg Lys Ser Leu Asn Ile Ile Pro Ala Gln Lys Gly Leu Ile Tyr
                165                 170                 175

Ser Pro Phe Pro Ile Tyr Val Tyr Asp Ser Ile Thr Lys Tyr Glu Asp
            180                 185                 190

Asp Phe Arg Val Glu Lys Gln Thr Val Ser Pro Gly Lys Pro Cys Leu
        195                 200                 205

Ile Pro Phe Phe Gln Asp Asp Ala Val Ile Arg Leu Glu Thr Thr Ser
210                 215                 220

His Cys Asn Ile Val Ile Val Glu Lys Glu Ala Val Phe Thr Lys Leu
225                 230                 235                 240

Val Ser Thr Tyr Asn Lys Leu Ser Ala Asn Thr Val Leu Ile Thr Gly
                245                 250                 255

Lys Gly Phe Pro Asp Phe Leu Thr Arg Leu Phe Leu Lys Lys Leu Glu
            260                 265                 270

Gln Asn Cys Ser Asn Leu Ile Ser Asn Cys Ser Ile Phe Thr Asp Ala
        275                 280                 285

Asp Pro Tyr Gly Ile Ser Ile Ala Leu Asn Tyr Ile Asn Ser Asn Ala
290                 295                 300

Asn Ala Ala Tyr Asn Cys Pro Met Val Asn Tyr Lys Gly Val Tyr Ile
305                 310                 315                 320

Thr Gln Ile Leu Ala Gln Asn Asn Arg Met Gly Ser Lys Val Val Gln
                325                 330                 335

Leu Leu Ser Leu Asn Gln Arg Asp Tyr Ser Leu Ala Lys Asn Leu Ile
            340                 345                 350

Val Ser Leu Thr Asn Ser Gly Glu Gly Val Val Ser Ser Pro Phe Lys
        355                 360                 365

Asn Phe Ile Val Glu Cys Gln Arg Glu Ile Phe Phe Gln Lys Lys Ala
370                 375                 380

Glu Met Asn Glu Ile Asp Val Gly Met Phe Gln Phe Xaa
385                 390                 395
```

<210> SEQ ID NO 3
<211> LENGTH: 372
<212> TYPE: PRT
<213> ORGANISM: Candida glabrata

<400> SEQUENCE: 3

```
Met Asn Phe Thr Leu Ala Asp Ile Tyr Asp Ser Ala Asp Ile Ser Glu
1               5                   10                  15

Leu Arg Ala Arg Leu Thr Ala Asp Lys Arg Ala Val Phe Phe Ser Pro
            20                  25                  30

Val Val Asp Asp Asn Ala Asp Lys Ser Gln Gln Ile His Asn Lys Ile
        35                  40                  45

Gln Asp Ile Leu Thr Leu Cys Lys Asn Ser Val Gly Gln Gln Gln Gln
    50                  55                  60

Gly Phe Gln Leu His Gly Leu Phe Lys Lys Pro Ile Glu Phe Pro Leu
65                  70                  75                  80
```

Ser Gly Arg Leu Lys Gly Lys Leu Leu Gln Asn Lys Ile Gln Lys Leu
            85                  90                  95

Ser Ile Thr Phe Thr Leu Leu Lys Glu Ile Gln Arg Asn Ile Glu Lys
            100                 105                 110

Cys Thr Ala Phe Thr Ser Arg Asp Ile Phe Tyr Arg Asn Val Glu Leu
            115                 120                 125

Phe Lys Ser Gln Arg Leu Val Val Asp Thr Val Asp His Ile Gln Lys
130                 135                 140

Ala Leu Gly Leu Thr Ile Arg Glu Asp Leu Asn Ile Thr Ala Thr Gln
145                 150                 155                 160

Lys Gly Leu Ile Phe Thr Ala Val Asp Ile Ile Asn Ser Ser Asp
            165                 170                 175

Thr Lys Lys Ile Lys Ile Thr Lys Gly Lys Ser Gln Leu Ile Pro Gln
            180                 185                 190

Phe Asp Ser Asn Ala Phe Ile Met Val Cys Lys Asp Pro Gln Met
            195                 200                 205

Ile Leu Lys Val Leu Val Ile Glu Lys Asp Ala Val Tyr Asn Thr Ile
            210                 215                 220

Ile Gln Lys Pro Thr Glu Gly Tyr Ile Val Val Thr Gly Lys Gly Tyr
225                 230                 235                 240

Pro Asp Met Leu Thr Arg Lys Phe Leu His Arg Leu Glu Gln Cys Asn
            245                 250                 255

Ser Asn Leu Gln Phe Val Ile Leu Thr Asp Pro Asp Pro His Gly Ile
            260                 265                 270

Asn Ile Ala Met Lys Tyr Gln Gly Phe Thr Thr Asp Ser Ile Tyr Pro
            275                 280                 285

Cys Ala Ser Leu Ile Arg Lys Gly Ile Ser Ile Leu Glu Leu Ile Asp
            290                 295                 300

Gly His Ser Ser Thr Ile Ala Gln Val Leu Pro Leu Ser Thr Arg Asp
305                 310                 315                 320

Ile Lys Leu Ala Gln Asn Ile Leu Phe Ser Gly His Ser Asp Leu Tyr
            325                 330                 335

Ala Asn Met Arg Thr Glu Leu Gln Arg Gln Leu Phe Leu Thr Lys Lys
            340                 345                 350

Gly Glu Met Asn Thr Thr Ile Ile Glu His Leu Leu Ser Asn Asp Arg
            355                 360                 365

Ile Thr Asn Tyr
    370

<210> SEQ ID NO 4
<211> LENGTH: 337
<212> TYPE: PRT
<213> ORGANISM: Yarrowia lipolytica

<400> SEQUENCE: 4

Met Asp Gln Asp Asp Thr Lys Ala Ile Ile Asn Lys Thr Ile Ser Arg
1               5                   10                  15

Leu Lys Lys Gln Phe His Glu Asp Ile Ser Ser Ala Ser Ile Phe Glu
            20                  25                  30

Thr His Ala Ser Lys Gly Ile Pro Leu Thr Thr Leu Cys Gly Asn Ser
            35                  40                  45

Val Asn Arg Phe Ser Ile Tyr Leu Arg Leu Gln Ile Ile Lys Ser
            50                  55                  60

Cys Leu Asp Lys Asp Lys Ile Thr Thr Lys Arg Asp Ile Tyr Tyr Asp

```
                65                  70                  75                  80
        Ala Val Asn Leu Phe Lys Thr Gln Gly Val Val Asp Ser Cys Ile Ala
                        85                  90                  95

Arg Ile Thr Asn Asp Phe Leu Gln Val Pro Arg Asp Ser Leu Asn Val
                    100                 105                 110

Val Ala Ala Gln Lys Gly Leu Ile Tyr Ser Ala Cys Asp Ser Ala Leu
                    115                 120                 125

Thr Ile Ser Tyr Lys Asp Asp Tyr Arg Ala Pro Val Thr Ile Pro Thr
                130                 135                 140

His Thr Thr Thr Leu Ile Pro Tyr Thr Thr Asn Ile Ser Asp Ile Gln
        145                 150                 155                 160

Leu Ala Pro Gln Val Asn Cys Ile Leu Ile Val Glu Lys Glu Ala Val
                        165                 170                 175

Phe Thr Thr Leu Cys Ala Tyr Ile Pro Lys Asp Thr Leu Leu Ile Thr
                    180                 185                 190

Gly Lys Gly Tyr Pro Asp His Met Thr Gln Asp Phe Val Arg Leu Phe
                    195                 200                 205

Asp Glu Met Leu Pro Leu Phe Ile Cys Val Asp Ala Asp Pro His Gly
                210                 215                 220

Ile His Ile Ala Ala Thr Tyr Arg Tyr Arg Ser Phe Val Arg Ala Pro
        225                 230                 235                 240

Ser Leu Gln Gly Leu Gly Ser Ser Ile Ser Tyr Ile Gly Val Ser Leu
                        245                 250                 255

Val Asp Phe Lys Arg Gly His Leu Pro Leu Glu Asp Lys Asn Arg Lys
                    260                 265                 270

His Ala Gly Arg Leu Leu Ser Ala Ile Thr Gly Arg Gln Ala Glu Ala
                    275                 280                 285

Leu Glu Leu Gly Asp Tyr Ile Glu Met Asn Lys Trp Lys Leu Glu Leu
                290                 295                 300

Gln Arg Met Leu Phe Leu Gly Lys Val Ala Glu Met Asn Val Ala Gly
        305                 310                 315                 320

Asp Gly Ser Glu Gly Arg Asn Leu Ala Arg Tyr Ile Phe Asp Arg Ile
                        325                 330                 335

His

<210> SEQ ID NO 5
<211> LENGTH: 750
<212> TYPE: PRT
<213> ORGANISM: Schizosaccharomyces pombe

<400> SEQUENCE: 5

Met Ile Met Glu Thr Glu Ser Pro Leu Ser Ile Thr Ser Pro Ser Pro
        1               5                   10                  15

Ser Asp Ser Thr Phe Gln Val Asp Met Glu Lys Thr Met His Ala Leu
                    20                  25                  30

Pro Ser Ser Leu Leu Asp Ser Pro Leu Leu Ser Thr Asn Glu His Tyr
                35                  40                  45

Pro Pro Lys Ser Thr Leu Leu Leu Ser Gly Pro Ser Pro Ile Arg Asn
            50                  55                  60

Ile Gln Leu Ser Ala Thr Lys Ser Ser Glu Ser Asn Ser Ile Asp Tyr
        65                  70                  75                  80

Leu Thr Asp Thr Gln Asn Ile Phe Pro Asn Phe Val Asn Asn Glu Asn
                        85                  90                  95

Asn Tyr Gln Phe Ser Thr Ala Pro Leu Asn Pro Ile Asp Ala Cys Arg
```

```
                100                 105                 110
Val Gly Glu Arg Lys Val Phe Thr Thr Gly Asn Val Leu Leu Ser Ala
            115                 120                 125

Asp Arg Gln Pro Leu Ser Thr Trp Gln Gln Asn Ile Ser Val Leu Ser
130                 135                 140

Glu Ser Pro Pro Gln Asn Gly Ile Gln Ser Tyr Ile Ser Ser Ser Glu
145                 150                 155                 160

Gln Ala Ala Gln Ala Leu Thr Arg Lys Pro Ser Val Thr Gly Phe Arg
            165                 170                 175

Ser Ser Ser Leu Asn Ser Asn Ser Asp Asp Ile Asp Ile Phe Ser His
            180                 185                 190

Ala Ser Arg Tyr Leu Phe Val Thr Asn Leu Pro Arg Ile Val Pro Tyr
            195                 200                 205

Ala Thr Leu Leu Glu Leu Phe Ser Lys Leu Gly Asp Val Lys Gly Ile
            210                 215                 220

Asp Thr Ser Ser Leu Ser Thr Asp Gly Ile Cys Ile Val Ala Phe Phe
225                 230                 235                 240

Asp Ile Arg Gln Ala Ile Gln Ala Ala Lys Ser Leu Arg Ser Gln Arg
            245                 250                 255

Phe Phe Asn Asp Arg Leu Leu Tyr Phe Gln Phe Cys Gln Arg Ser Ser
            260                 265                 270

Ile Gln Lys Met Ile Asn Gln Gly Ala Thr Ile Gln Phe Leu Asp Asp
            275                 280                 285

Asn Glu Gly Gln Leu Leu Leu Asn Met Gln Gly Gly Ser Val Leu Ser
            290                 295                 300

Ile Leu Gln Leu Gln Ser Ile Leu Gln Thr Phe Gly Pro Leu Leu Ile
305                 310                 315                 320

Met Lys Pro Leu Arg Ser Gln Asn Val Ser Gln Ile Ile Cys Glu Phe
            325                 330                 335

Tyr Asp Thr Arg Asp Ala Ser Phe Ala Leu Asp Glu Leu Asp Gly Arg
            340                 345                 350

Ile Ile His Asn Cys Cys Leu Gln Val Ala Tyr Tyr Asp Ala Met Ala
            355                 360                 365

Asp Ser Val Ser Thr Ser Ser Ala Ser Ser Leu Ser Val Pro Arg Gly
            370                 375                 380

Phe Ser Gly Met Leu Asn Asn Asn Ser Glu Trp Asn Asn Ser Met Thr
385                 390                 395                 400

Met Ser Ser Asn Gln Glu Thr Pro Thr Ala Ala Ser Cys Ala Val Ser
            405                 410                 415

Arg Ile Gly Ser Ser Tyr Gly Met Ser Asn Asn Phe Gly Ser Val Pro
            420                 425                 430

Leu Gly Arg Thr Glu Ser Ser Pro Ala Trp Gly Thr Ser Gly Tyr Tyr
            435                 440                 445

Asp Val Ser Ser Thr Ser Pro Val Ala Pro Ser Asp Arg Asn Pro Ser
            450                 455                 460

Arg Gln Tyr Asn Ser Ile Arg Tyr Gly Leu Asp Val Asn Pro Ile Ala
465                 470                 475                 480

Pro Pro Asn Ser Ser Arg Leu Lys Gln Arg Asn Ser Asp Leu Leu Asn
            485                 490                 495

Gly Ile Asn Pro Gln Trp Ser Pro Phe Ser Ser Asn Thr Gly Lys Val
            500                 505                 510

Phe Asp Ser Pro Thr Gly Ser Leu Gly Met Arg Arg Ser Leu Thr Val
            515                 520                 525
```

-continued

Gly Ala Asn Ala Ser Cys Ser Asn Pro Thr Asn Leu Ser Phe Ala Ser
            530                 535                 540

Leu Thr Leu His Asp Ser Lys Ala Asp Ser Thr Leu Ser Ala Ser Ser
545                 550                 555                 560

Leu Asn Pro Asp Leu Asn Leu Gln Arg Tyr Thr Pro Thr Val Glu Lys
                565                 570                 575

His Ala Ser Asp Arg Asn Ser Val Asp Tyr Ala Gln Ile Ala Ser Gly
            580                 585                 590

Ile Asp Thr Arg Thr Thr Val Met Ile Lys Asn Ile Pro Asn Lys Phe
        595                 600                 605

Thr Gln Gln Met Leu Arg Asp Tyr Ile Asp Val Thr Asn Lys Gly Thr
    610                 615                 620

Tyr Asp Phe Leu Tyr Leu Arg Ile Asp Phe Val Asn Lys Cys Asn Val
625                 630                 635                 640

Gly Tyr Ala Phe Ile Asn Phe Ile Glu Pro Gln Ser Ile Ile Thr Phe
                645                 650                 655

Gly Lys Ala Arg Val Gly Thr Gln Trp Asn Val Phe His Ser Glu Lys
            660                 665                 670

Ile Cys Asp Ile Ser Tyr Ala Asn Ile Gln Gly Lys Asp Arg Leu Ile
        675                 680                 685

Glu Lys Phe Arg Asn Ser Cys Val Met Asp Glu Asn Pro Ala Tyr Arg
    690                 695                 700

Pro Lys Ile Phe Val Ser His Gly Pro Asn Arg Gly Met Glu Glu Pro
705                 710                 715                 720

Phe Pro Ala Pro Asn Asn Ala Arg Arg Lys Leu Arg Ser Ile Ala Ser
                725                 730                 735

Ala Gln Gln Ile Gly Leu Phe Pro Pro Thr Ala Ser Lys Cys
            740                 745                 750

<210> SEQ ID NO 6
<211> LENGTH: 76
<212> TYPE: PRT
<213> ORGANISM: Schizosaccharomyces pombe

<400> SEQUENCE: 6

Arg Tyr Leu Phe Val Thr Asn Leu Pro Arg Ile Val Pro Tyr Ala Thr
1               5                   10                  15

Leu Leu Glu Leu Phe Ser Lys Leu Gly Asp Val Lys Gly Ile Asp Thr
            20                  25                  30

Ser Ser Leu Ser Thr Asp Gly Ile Cys Ile Val Ala Phe Phe Asp Ile
        35                  40                  45

Arg Gln Ala Ile Gln Ala Ala Lys Ser Leu Arg Ser Gln Arg Phe Phe
    50                  55                  60

Asn Asp Arg Leu Leu Tyr Phe Gln Phe Cys Gln Arg
65                  70                  75

<210> SEQ ID NO 7
<211> LENGTH: 97
<212> TYPE: PRT
<213> ORGANISM: Schizosaccharomyces pombe

<400> SEQUENCE: 7

Arg Thr Thr Val Met Ile Lys Asn Ile Pro Asn Lys Phe Thr Gln Gln
1               5                   10                  15

Met Leu Arg Asp Tyr Ile Asp Val Thr Asn Lys Gly Thr Tyr Asp Phe
            20                  25                  30

```
Leu Tyr Leu Arg Ile Asp Phe Val Asn Lys Cys Asn Val Gly Tyr Ala
         35                  40                  45

Phe Ile Asn Phe Ile Glu Pro Gln Ser Ile Ile Thr Phe Gly Lys Ala
 50                  55                  60

Arg Val Gly Thr Gln Trp Asn Val Phe His Ser Glu Lys Ile Cys Asp
 65                  70                  75                  80

Ile Ser Tyr Ala Asn Ile Gln Gly Lys Asp Arg Leu Ile Glu Lys Phe
             85                  90                  95

Arg

<210> SEQ ID NO 8
<211> LENGTH: 1562
<212> TYPE: DNA
<213> ORGANISM: Schizosaccharomyces pombe

<400> SEQUENCE: 8
```

| | | | | |
|---|---|---|---|---|
| taaattattg dacagaattg agtttctttc actatgcatt ggaaattcct ataaatagtc | | | | 60 |
| gatgaagtct gcgaaacaag ggaggtaaac agacttagtg ggtattaaaa tgttggtcaa | | | | 120 |
| tcttctgccg tcttgattta aaagcacttc tcttttacta ttgtaagacg gaatatgcat | | | | 180 |
| gcaagatcgc tttagttggt tgaatgtctc tttctttgtg ttgtggtttg ttcgtttttt | | | | 240 |
| tctaatttgg aatattataa gaaacgttgt tttcttgcaa cattttgaaa tggtcattca | | | | 300 |
| aaaagctgga ttcggtacca cttttctttt taccttgtct tctaagctct gttaaatttc | | | | 360 |
| ttgatggggt ccagttaaac caaccccaa gttggtttat gtgagccttg tctctttttt | | | | 420 |
| ggatgaatag tagcttagat agtgatagtt attattatga ctgatggaat ctacttaaaa | | | | 480 |
| atggattcca tttttgtct actgtaattg aattcttttt ggtacacttt ttggctgcat | | | | 540 |
| tgttatcctt gaaagcactt acaatgttta actttgcga atgactgaaa cagaaaagaa | | | | 600 |
| ataaaacgac tgtacctgaa ctattgttga acaatatta aaacgtattc ctgaaacaga | | | | 660 |
| ttaaactaca ttaaattttg ttaatgaatt aaacgtgaaa cttgaaagtt tgatgcgaaa | | | | 720 |
| caaaacccgc agtttgttta aacgctatt tgtgattaaa attgatgaac cagtttaaac | | | | 780 |
| tatgaaagtg tttgaaaacg tgctgaaacc attcgttaaa ccctgcaaac caacataaaa | | | | 840 |
| aaaattgaaa ataaacaata accacagcaa gctaattcaa ttccaacaat ggtatgttgc | | | | 900 |
| attggtcttc ggttgtgctg tgctccctct tttttttgagc atagttaaaa ccattaatac | | | | 960 |
| tatttaaaca tttctcttta aaaagagaa gagaatagca acacatagaa tttccaaatt | | | | 1020 |
| caacatgcct tcaaatttga aatcgcaagg aacagctatt aatgaatgaa acgagttaaa | | | | 1080 |
| ttgaaataaa tcaaacacta taagattat tattctatttt cttgcttaaa acacacttta | | | | 1140 |
| aggaattgaa atttttcacg taaatgttg atgaactggc tttaaattta catgcaagtc | | | | 1200 |
| ttgattgtga aatgatgcgt tggaagcatg aattggtatt ttcttttttta aaaaaagcaa | | | | 1260 |
| tgaaaagttt gaaaaaggca ataaaacttg gaggtggttg gacttgccg atttcacgaa | | | | 1320 |
| gtttttcttt gctgtttgaa actcaaccaa ataaattaaa cagtggtagc agccccaatt | | | | 1380 |
| aaactgaaaa tctatcagtt atatgttcat gaatgtgtaa aagcagcaga acagacagat | | | | 1440 |
| cccagcattt ttcccttctc tttgcactac attatgagag ggataactga tattctgtaa | | | | 1500 |
| tgtagatctg agaaaacgaa ggcaaagcta atcccgaatg taaggtttag ggagctactt | | | | 1560 |
| gt | | | | 1562 |

<210> SEQ ID NO 9

```
<211> LENGTH: 508
<212> TYPE: DNA
<213> ORGANISM: Schizosaccharomyces pombe

<400> SEQUENCE: 9
taaattattg acagaattg agtttctttc actatgcatt ggaaattcct ataaatagtc      60
gatgaagtct gcgaaacaag ggaggtaaac agacttagtg ggtattaaaa tgttggtcaa     120
tcttctgccg tcttgattta aaagcacttc tcttttacta ttgtaagacg gaatatgcat     180
gcaagatcgc tttagttggt tgaatgtctc tttctttgtg ttgtggtttg ttcgttttt     240
tctaatttgg aatattataa gaaacgttgt tttcttgcaa cattttgaaa tggtcattca     300
aaaagctgga ttcggtacca cttttctttt taccttgtct tctaagctct gttaaatttc     360
ttgatggggt ccagttaaac caaccccaa gttggtttat gtgagccttg tctcttttt      420
ggatgaatag tagcttagat agtgatagtt attattatga ctgatggaat ctacttaaaa    480
atggattcca ttttttgtct actgtaat                                       508

<210> SEQ ID NO 10
<211> LENGTH: 582
<212> TYPE: DNA
<213> ORGANISM: Schizosaccharomyces pombe

<400> SEQUENCE: 10
taaattattg acagaattg agtttctttc actatgcatt ggaaattcct ataaatagtc      60
gatgaagtct gcgaaacaag ggaggtaaac agacttagtg ggtattaaaa tgttggtcaa     120
tcttctgccg tcttgattta aaagcacttc tcttttacta ttgtaagacg gaatatgcat     180
gcaagatcgc tttagttggt tgaatgtctc tttctttgtg ttgtggtttg ttcgttttt     240
tctaatttgg aatattataa gaaacgttgt tttcttgcaa cattttgaaa tggtcattca     300
aaaagctgga ttcggtacca cttttctttt taccttgtct tctaagctct gttaaatttc     360
ttgatggggt ccagttaaac caaccccaa gttggtttat gtgagccttg tctcttttt      420
ggatgaatag tagcttagat agtgatagtt attattatga ctgatggaat ctacttaaaa    480
atggattcca ttttttgtct actgtaattg aattctttt ggtacacttt ttggctgcat     540
tgttatcctt gaaagcactt acaatgttta aactttcga at                        582

<210> SEQ ID NO 11
<211> LENGTH: 238
<212> TYPE: PRT
<213> ORGANISM: Aequorea victoria

<400> SEQUENCE: 11
```

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val

```
                100             105             110
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 12
<211> LENGTH: 221
<212> TYPE: PRT
<213> ORGANISM: Mus musculus

<400> SEQUENCE: 12

Met Ala Gly Lys Pro Val Leu His Tyr Phe Asp Gly Arg Gly Arg Met
1               5                   10                  15

Glu Pro Ile Arg Trp Leu Leu Ala Ala Ala Gly Val Glu Phe Glu Glu
            20                  25                  30

Lys Phe Leu Lys Thr Arg Asp Asp Leu Ala Arg Leu Arg Ser Asp Gly
        35                  40                  45

Ser Leu Met Phe Gln Gln Val Pro Met Val Glu Ile Asp Gly Met Lys
50                  55                  60

Leu Val Gln Thr Lys Ala Ile Leu Asn Tyr Ile Ala Ser Lys Tyr Asn
65                  70                  75                  80

Leu Tyr Gly Lys Asp Met Lys Glu Arg Ala Ile Ile Asp Met Tyr Thr
                85                  90                  95

Glu Gly Val Ala Asp Leu Glu Ile Met Ile Leu Tyr Tyr Pro His Met
            100                 105                 110

Pro Pro Glu Glu Lys Glu Ala Ser Leu Ala Lys Ile Lys Glu Gln Thr
        115                 120                 125

Arg Asn Arg Tyr Phe Pro Ala Phe Glu Lys Val Leu Lys Ser His Gly
130                 135                 140

Gln Asp Tyr Leu Val Gly Asn Arg Leu Ser Arg Ala Asp Ile Ala Leu
145                 150                 155                 160

Val Glu Leu Leu Tyr His Val Glu Glu Leu Asp Pro Gly Val Val Asp
                165                 170                 175

Asn Phe Pro Leu Leu Lys Ala Leu Arg Ser Arg Val Ser Asn Leu Pro
            180                 185                 190

Thr Val Lys Lys Phe Leu Gln Pro Gly Ser Gln Arg Lys Pro Phe Asp
        195                 200                 205

Asp Ala Lys Cys Val Glu Ser Ala Lys Lys Ile Phe Ser
210                 215                 220

<210> SEQ ID NO 13
<211> LENGTH: 292
```

<212> TYPE: PRT
<213> ORGANISM: Zea mays

<400> SEQUENCE: 13

Met Ala Thr Thr Glu Pro Ala Ala Val Arg Leu Val Gly Ser Phe Ala
1               5                   10                  15

Ser Pro Phe Val His Arg Ala Glu Val Ala Leu Arg Leu Lys Gly Val
            20                  25                  30

Pro Tyr Glu Leu Ile Leu Glu Asp Leu Gly Asn Lys Ser Glu Leu Leu
        35                  40                  45

Leu Ala His Asn Pro Val His Lys Leu Val Pro Val Leu Leu His Gly
    50                  55                  60

Asp Arg Ala Ile Ser Glu Ser Leu Val Ile Leu Glu Tyr Val Asp Glu
65                  70                  75                  80

Ala Phe Asp Gly Pro Pro Leu Leu Pro Ala Glu Pro His Ala Arg Ala
                85                  90                  95

Asp Ala Arg Phe Trp Ala His Phe Ile Asp Gln Lys Phe Ala Arg Pro
            100                 105                 110

Phe Trp Met Ser Phe Trp Thr Asp Asp Glu Glu Arg Arg Glu Ala Met
        115                 120                 125

Ala Lys Glu Ala Lys Glu Asn Leu Ala Leu Leu Glu Ala Gln Leu Arg
    130                 135                 140

Gly Gln Arg Phe Gly Gly Glu Ala Ile Gly Phe Val Asp Ile Ala
145                 150                 155                 160

Ala Cys Ala Leu Ala His Trp Val Gly Val Ile Glu Glu Ala Ala Gly
                165                 170                 175

Val Val Leu Val Gly Gly Glu Glu Phe Pro Ala Leu Arg Glu Trp Ala
            180                 185                 190

Asp Ala Tyr Val Asn Asp Ala Thr Val Lys Gln Cys Leu Arg Ser Arg
        195                 200                 205

Asp Glu Leu Val Asp Tyr Phe Ser Ala Arg Lys Glu Met Tyr Leu Leu
    210                 215                 220

Arg Ala Arg Ala Thr Pro Arg Ser Met Thr Glu Arg Pro Ser Asp Leu
225                 230                 235                 240

Val Val Asn Lys Leu Val Leu Phe Val Lys Gly Thr Ala Thr Ser
                245                 250                 255

Thr His Asn Thr Val Lys Pro Leu Ile Leu Glu Glu Leu Gly Val
            260                 265                 270

Pro His Asp Ile Tyr Val Val Glu Lys Val Ser Ala Pro Trp Phe Ser
        275                 280                 285

Glu Ile Asn Pro
    290

<210> SEQ ID NO 14
<211> LENGTH: 219
<212> TYPE: PRT
<213> ORGANISM: Saccharomyces cerevisiae

<400> SEQUENCE: 14

Met Lys Gln Lys Met Ile Ile Tyr Asp Thr Pro Ala Gly Pro Tyr Pro
1               5                   10                  15

Ala Arg Val Arg Ile Ala Leu Ala Glu Lys Asn Met Leu Ser Ser Val
            20                  25                  30

Gln Phe Val Arg Ile Asn Leu Trp Lys Gly Glu His Lys Lys Pro Glu
        35                  40                  45

```
Phe Leu Ala Lys Asn Tyr Ser Gly Thr Val Pro Val Leu Glu Leu Asp
    50                  55                  60

Asp Gly Thr Leu Ile Ala Glu Cys Thr Ala Ile Thr Glu Tyr Ile Asp
 65                  70                  75                  80

Ala Leu Asp Gly Thr Pro Thr Leu Thr Gly Lys Thr Pro Leu Glu Lys
                     85                  90                  95

Gly Val Ile His Met Met Asn Lys Arg Ala Glu Leu Glu Leu Leu Asp
                100                 105                 110

Pro Val Ser Val Tyr Phe His Ala Thr Pro Gly Leu Gly Pro Glu
                115                 120                 125

Val Glu Leu Tyr Gln Asn Lys Glu Trp Gly Leu Arg Gln Arg Asp Lys
    130                 135                 140

Ala Leu His Gly Met His Tyr Phe Asp Thr Val Leu Arg Glu Arg Pro
145                 150                 155                 160

Tyr Val Ala Gly Asp Ser Phe Ser Met Ala Asp Ile Thr Val Ile Ala
                165                 170                 175

Gly Leu Ile Phe Ala Ala Ile Val Lys Leu Gln Val Pro Glu Glu Cys
                180                 185                 190

Glu Ala Leu Arg Ala Trp Tyr Lys Arg Met Gln Gln Arg Pro Ser Val
    195                 200                 205

Lys Lys Leu Leu Glu Ile Arg Ser Lys Ser Ser
    210                 215

<210> SEQ ID NO 15
<211> LENGTH: 240
<212> TYPE: PRT
<213> ORGANISM: Aspergillus niger

<400> SEQUENCE: 15

Met Thr Glu Arg Pro Ser Asp Leu Val Val Asn Lys Leu Val Leu Phe
 1               5                  10                  15

Val Val Lys Gly Thr Ala Thr Ser Thr His Asn Thr Val Lys Pro Leu
                20                  25                  30

Ile Leu Leu Glu Glu Leu Gly Val Pro His Asp Ile Tyr Val Val Glu
                35                  40                  45

Lys Val Ser Ala Pro Trp Phe Ser Glu Ile Asn Pro His Lys Met Val
    50                  55                  60

Pro Ala Ile Leu Asp Arg Ser Pro Asp Ser Gln Asp Thr Leu Arg Ala
 65                  70                  75                  80

Trp Glu Ser Thr Ser Thr Leu Met Tyr Ile Ala Asp Ala Tyr Asp Lys
                 85                  90                  95

Asp Gly Thr Phe Gly Gly Arg Asn Val Gln Glu Arg Ala Glu Ile Asn
                100                 105                 110

Asn Trp Leu Thr Leu His Thr Ala Ala Leu Gly Pro Thr Ala Lys Tyr
                115                 120                 125

Trp Leu Tyr Phe Tyr Lys Leu His Pro Glu Lys Leu Pro Lys Thr Ile
    130                 135                 140

Glu Lys Leu Arg Ser Asn Ile Thr Val Gln Tyr Asp Ile Leu Glu Arg
145                 150                 155                 160

Arg Leu Asn Glu Pro Gly Gln Glu Tyr Leu Ala Leu Lys Asp Arg Pro
                165                 170                 175

Ser Ile Ala Asp Ile Ala Thr Leu Pro Phe Ala Met Lys Ser Thr Ala
                180                 185                 190

Glu Leu Phe Gly Leu Glu Phe Glu Arg Trp Pro Lys Leu Gln Glu Trp
    195                 200                 205
```

```
Ser Val Arg Met Ser Glu Arg Glu Ala Val Lys Arg Ala Trp Gln Arg
    210                 215                 220

Val Ala Gly Phe Gly His Gly Glu Lys Glu Tyr Gly Met Leu Glu Ala
225                 230                 235                 240
```

<210> SEQ ID NO 16
<211> LENGTH: 380
<212> TYPE: PRT
<213> ORGANISM: Mus musculus

<400> SEQUENCE: 16

```
Met Met Phe Ser Gly Phe Asn Ala Asp Tyr Glu Ala Ser Ser Ser Arg
1               5                   10                  15

Cys Ser Ser Ala Ser Pro Ala Gly Asp Ser Leu Ser Tyr Tyr His Ser
                20                  25                  30

Pro Ala Asp Ser Phe Ser Ser Met Gly Ser Pro Val Asn Thr Gln Asp
            35                  40                  45

Phe Cys Ala Asp Leu Ser Val Ser Ser Ala Asn Phe Ile Pro Thr Val
    50                  55                  60

Thr Ala Ile Ser Thr Ser Pro Asp Leu Gln Trp Leu Val Gln Pro Thr
65                  70                  75                  80

Leu Val Ser Ser Val Ala Pro Ser Gln Thr Arg Ala Pro His Pro Tyr
                85                  90                  95

Gly Leu Pro Thr Gln Ser Ala Gly Ala Tyr Ala Arg Ala Gly Met Val
            100                 105                 110

Lys Thr Val Ser Gly Gly Arg Ala Gln Ser Ile Gly Arg Arg Gly Lys
        115                 120                 125

Val Glu Gln Leu Ser Pro Glu Glu Glu Lys Arg Arg Ile Arg Arg
    130                 135                 140

Glu Arg Asn Lys Met Ala Ala Ala Lys Cys Arg Asn Arg Arg Arg Glu
145                 150                 155                 160

Leu Thr Asp Thr Leu Gln Ala Glu Thr Asp Gln Leu Glu Asp Glu Lys
                165                 170                 175

Ser Ala Leu Gln Thr Glu Ile Ala Asn Leu Leu Lys Glu Lys Glu Lys
            180                 185                 190

Leu Glu Phe Ile Leu Ala Ala His Arg Pro Ala Cys Lys Ile Pro Asp
        195                 200                 205

Asp Leu Gly Phe Pro Glu Glu Met Ser Val Ala Ser Leu Asp Leu Thr
    210                 215                 220

Gly Gly Leu Pro Glu Ala Ser Thr Pro Glu Ser Glu Glu Ala Phe Thr
225                 230                 235                 240

Leu Pro Leu Leu Asn Asp Pro Glu Pro Lys Pro Ser Leu Glu Pro Val
                245                 250                 255

Lys Ser Ile Ser Asn Val Glu Leu Lys Ala Glu Pro Phe Asp Asp Phe
            260                 265                 270

Leu Phe Pro Ala Ser Ser Arg Pro Ser Gly Ser Glu Thr Ser Arg Ser
        275                 280                 285

Val Pro Asp Val Asp Leu Ser Gly Ser Phe Tyr Ala Ala Asp Trp Glu
    290                 295                 300

Pro Leu His Ser Asn Ser Leu Gly Met Gly Pro Met Val Thr Glu Leu
305                 310                 315                 320

Glu Pro Leu Cys Thr Pro Val Val Thr Cys Thr Pro Gly Cys Thr Thr
                325                 330                 335

Tyr Thr Ser Ser Phe Val Phe Thr Tyr Pro Glu Ala Asp Ser Phe Pro
```

```
                          340                 345                 350
        Ser Cys Ala Ala Ala His Arg Lys Gly Ser Ser Ser Asn Glu Pro Ser
                        355                 360                 365

Ser Asp Ser Leu Ser Ser Pro Thr Leu Leu Ala Leu
                        370                 375                 380

<210> SEQ ID NO 17
        <211> LENGTH: 380
        <212> TYPE: PRT
        <213> ORGANISM: Homo sapiens

<400> SEQUENCE: 17

Met Met Phe Ser Gly Phe Asn Ala Asp Tyr Glu Ala Ser Ser Ser Arg
        1               5                   10                  15

Cys Ser Ser Ala Ser Pro Ala Gly Asp Ser Leu Ser Tyr Tyr His Ser
                        20                  25                  30

Pro Ala Asp Ser Phe Ser Ser Met Gly Ser Pro Val Asn Ala Gln Asp
                        35                  40                  45

Phe Cys Thr Asp Leu Ala Val Ser Ser Ala Asn Phe Ile Pro Thr Val
                50                  55                  60

Thr Ala Ile Ser Thr Ser Pro Asp Leu Gln Trp Leu Val Gln Pro Ala
        65                  70                  75                  80

Leu Val Ser Ser Val Ala Pro Ser Gln Thr Arg Ala Pro His Pro Phe
                        85                  90                  95

Gly Val Pro Ala Pro Ser Ala Gly Ala Tyr Ser Arg Ala Gly Val Val
                        100                 105                 110

Lys Thr Met Thr Gly Gly Arg Ala Gln Ser Ile Gly Arg Arg Gly Lys
                        115                 120                 125

Val Glu Gln Leu Ser Pro Glu Glu Glu Lys Arg Arg Ile Arg Arg
                        130                 135                 140

Glu Arg Asn Lys Met Ala Ala Ala Lys Cys Arg Asn Arg Arg Arg Glu
        145                 150                 155                 160

Leu Thr Asp Thr Leu Gln Ala Glu Thr Asp Gln Leu Glu Asp Glu Lys
                        165                 170                 175

Ser Ala Leu Gln Thr Glu Ile Ala Asn Leu Leu Lys Glu Lys Glu Lys
                        180                 185                 190

Leu Glu Phe Ile Leu Ala Ala His Arg Pro Ala Cys Lys Ile Pro Asp
                        195                 200                 205

Asp Leu Gly Phe Pro Glu Glu Met Ser Val Ala Ser Leu Asp Leu Thr
                        210                 215                 220

Gly Gly Leu Pro Glu Val Ala Thr Pro Glu Ser Glu Glu Ala Phe Thr
        225                 230                 235                 240

Leu Pro Leu Leu Asn Asp Pro Glu Pro Lys Pro Ser Val Glu Pro Val
                        245                 250                 255

Lys Ser Ile Ser Ser Met Glu Leu Lys Thr Glu Pro Phe Asp Asp Phe
                        260                 265                 270

Leu Phe Pro Ala Ser Ser Arg Pro Ser Gly Ser Glu Thr Ala Arg Ser
                        275                 280                 285

Val Pro Asp Met Asp Leu Ser Gly Ser Phe Tyr Ala Ala Asp Trp Glu
                        290                 295                 300

Pro Leu His Ser Gly Ser Leu Gly Met Gly Pro Met Ala Thr Glu Leu
        305                 310                 315                 320

Glu Pro Leu Cys Thr Pro Val Val Thr Cys Thr Pro Ser Cys Thr Ala
                        325                 330                 335
```

```
Tyr Thr Ser Ser Phe Val Phe Thr Tyr Pro Glu Ala Asp Ser Phe Pro
            340                 345                 350

Ser Cys Ala Ala Ala His Arg Lys Gly Ser Ser Ser Asn Glu Pro Ser
        355                 360                 365

Ser Asp Ser Leu Ser Ser Pro Thr Leu Leu Ala Leu
    370                 375                 380

<210> SEQ ID NO 18
<211> LENGTH: 334
<212> TYPE: PRT
<213> ORGANISM: Mus musculus

<400> SEQUENCE: 18

Met Thr Ala Lys Met Glu Thr Thr Phe Tyr Asp Asp Ala Leu Asn Ala
1               5                   10                  15

Ser Phe Leu Gln Ser Glu Ser Gly Ala Tyr Gly Tyr Ser Asn Pro Lys
            20                  25                  30

Ile Leu Lys Gln Ser Met Thr Leu Asn Leu Ala Asp Pro Val Gly Ser
        35                  40                  45

Leu Lys Pro His Leu Arg Ala Lys Asn Ser Asp Leu Leu Thr Ser Pro
    50                  55                  60

Asp Val Gly Leu Leu Lys Leu Ala Ser Pro Glu Leu Glu Arg Leu Ile
65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
        115                 120                 125

Ser Val Thr Ser Ala Ala Gln Pro Val Ser Gly Ala Gly Met Val Ala
    130                 135                 140

Pro Ala Val Ala Ser Val Ala Gly Ala Gly Gly Gly Gly Tyr Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ser Gln Pro Gln Gln Gln Gln Pro Pro
        195                 200                 205

Gln Pro Pro His His Leu Pro Gln Gln Ile Pro Val Gln His Pro Arg
    210                 215                 220

Leu Gln Ala Leu Lys Glu Glu Pro Gln Thr Val Pro Glu Met Pro Gly
225                 230                 235                 240

Glu Thr Pro Pro Leu Ser Pro Ile Asp Met Glu Ser Gln Glu Arg Ile
                245                 250                 255

Lys Ala Glu Arg Lys Arg Met Arg Asn Arg Ile Ala Ala Ser Lys Cys
            260                 265                 270

Arg Lys Arg Lys Leu Glu Arg Ile Ala Arg Leu Glu Glu Lys Val Lys
        275                 280                 285

Thr Leu Lys Ala Gln Asn Ser Glu Leu Ala Ser Thr Ala Asn Met Leu
    290                 295                 300

Arg Glu Gln Val Ala Gln Leu Lys Gln Lys Val Met Asn His Val Asn
305                 310                 315                 320

Ser Gly Cys Gln Leu Met Leu Thr Gln Gln Leu Gln Thr Phe
                325                 330
```

<210> SEQ ID NO 19
<211> LENGTH: 331
<212> TYPE: PRT
<213> ORGANISM: Homo sapiens

<400> SEQUENCE: 19

Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
        35                  40                  45

Leu Lys Pro His Leu Arg Ala Lys Asn Ser Asp Leu Leu Thr Ser Pro
    50                  55                  60

Asp Val Gly Leu Leu Lys Leu Ala Ser Pro Glu Leu Glu Arg Leu Ile
65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
        115                 120                 125

Ser Val Thr Ser Ala Ala Gln Pro Val Asn Gly Ala Gly Met Val Ala
    130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285

Ala Gln Asn Ser Glu Leu Ala Ser Thr Ala Asn Met Leu Arg Glu Gln
    290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330

<210> SEQ ID NO 20
<211> LENGTH: 2549
<212> TYPE: PRT
<213> ORGANISM: Homo sapiens

<400> SEQUENCE: 20

```
Met Leu Gly Thr Gly Pro Ala Ala Thr Ala Thr Thr Ser
1               5                   10              15

Ser Asn Val Ser Val Leu Gln Gln Phe Ala Ser Gly Leu Lys Ser Arg
                20                  25                  30

Asn Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                      70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
                100                 105                 110

Asn Leu Leu Pro Ser Asn Asp Pro Val Val Met Glu Met Ala Ser Lys
            115                 120                 125

Ala Ile Gly Arg Leu Ala Met Ala Gly Asp Thr Phe Thr Ala Glu Tyr
            130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
            195                 200                 205

Ala Val Ala Ala Leu Arg Ala Cys Leu Ile Leu Thr Thr Gln Arg Glu
            210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
            290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
            325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
            355                 360                 365

Lys Phe Asp Gln Val Cys Gln Trp Val Leu Lys Cys Arg Asn Ser Lys
            370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415
```

```
Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
            820                 825                 830

Leu Leu Ala Lys Arg Gln Val Ala Leu Trp Thr Leu Gly Gln Leu Val
```

-continued

```
            835                 840                 845
Ala Ser Thr Gly Tyr Val Val Glu Pro Tyr Arg Lys Tyr Pro Thr Leu
    850                 855                 860
Leu Glu Val Leu Leu Asn Phe Leu Lys Thr Glu Gln Asn Gln Gly Thr
865                 870                 875                 880
Arg Arg Glu Ala Ile Arg Val Leu Gly Leu Gly Ala Leu Asp Pro
                885                 890                 895
Tyr Lys His Lys Val Asn Ile Gly Met Ile Asp Gln Ser Arg Asp Ala
        900                 905                 910
Ser Ala Val Ser Leu Ser Glu Ser Lys Ser Ser Gln Asp Ser Ser Asp
        915                 920                 925
Tyr Ser Thr Ser Glu Met Leu Val Asn Met Gly Asn Leu Pro Leu Asp
    930                 935                 940
Glu Phe Tyr Pro Ala Val Ser Met Val Ala Leu Met Arg Ile Phe Arg
945                 950                 955                 960
Asp Gln Ser Leu Ser His His His Thr Met Val Val Gln Ala Ile Thr
                965                 970                 975
Phe Ile Phe Lys Ser Leu Gly Leu Lys Cys Val Gln Phe Leu Pro Gln
                980                 985                 990
Val Met Pro Thr Phe Leu Asn Val  Ile Arg Val Cys Asp  Gly Ala Ile
                995                 1000                1005
Arg Glu  Phe Leu Phe Gln Gln  Leu Gly Met Leu Val  Ser Phe Val
        1010                1015                1020
Lys Ser  His Ile Arg Pro Tyr  Met Asp Glu Ile Val  Thr Leu Met
        1025                1030                1035
Arg Glu  Phe Trp Val Met Asn  Thr Ser Ile Gln Ser  Thr Ile Ile
        1040                1045                1050
Leu Leu  Ile Glu Gln Ile Val  Val Ala Leu Gly Gly  Glu Phe Lys
        1055                1060                1065
Leu Tyr  Leu Pro Gln Leu Ile  Pro His Met Leu Arg  Val Phe Met
        1070                1075                1080
His Asp  Asn Ser Pro Gly Arg  Ile Val Ser Ile Lys  Leu Leu Ala
        1085                1090                1095
Ala Ile  Gln Leu Phe Gly Ala  Asn Leu Asp Asp Tyr  Leu His Leu
        1100                1105                1110
Leu Leu  Pro Pro Ile Val Lys  Leu Phe Asp Ala Pro  Glu Ala Pro
        1115                1120                1125
Leu Pro  Ser Arg Lys Ala Ala  Leu Glu Thr Val Asp  Arg Leu Thr
        1130                1135                1140
Glu Ser  Leu Asp Phe Thr Asp  Tyr Ala Ser Arg Ile  Ile His Pro
        1145                1150                1155
Ile Val  Arg Thr Leu Asp Gln  Ser Pro Glu Leu Arg  Ser Thr Ala
        1160                1165                1170
Met Asp  Thr Leu Ser Ser Leu  Val Phe Gln Leu Gly  Lys Lys Tyr
        1175                1180                1185
Gln Ile  Phe Ile Pro Met Val  Asn Lys Val Leu Val  Arg His Arg
        1190                1195                1200
Ile Asn  His Gln Arg Tyr Asp  Val Leu Ile Cys Arg  Ile Val Lys
        1205                1210                1215
Gly Tyr  Thr Leu Ala Asp Glu  Glu Glu Asp Pro Leu  Ile Tyr Gln
        1220                1225                1230
His Arg  Met Leu Arg Ser Gly  Gln Gly Asp Ala Leu  Ala Ser Gly
        1235                1240                1245
```

-continued

Pro Val Glu Thr Gly Pro Met Lys Lys Leu His Val Ser Thr Ile
1250                    1255                1260

Asn Leu Gln Lys Ala Trp Gly Ala Ala Arg Arg Val Ser Lys Asp
1265                    1270                1275

Asp Trp Leu Glu Trp Leu Arg Arg Leu Ser Leu Glu Leu Leu Lys
1280                    1285                1290

Asp Ser Ser Ser Pro Ser Leu Arg Ser Cys Trp Ala Leu Ala Gln
1295                    1300                1305

Ala Tyr Asn Pro Met Ala Arg Asp Leu Phe Asn Ala Ala Phe Val
1310                    1315                1320

Ser Cys Trp Ser Glu Leu Asn Glu Asp Gln Gln Asp Glu Leu Ile
1325                    1330                1335

Arg Ser Ile Glu Leu Ala Leu Thr Ser Gln Asp Ile Ala Glu Val
1340                    1345                1350

Thr Gln Thr Leu Leu Asn Leu Ala Glu Phe Met Glu His Ser Asp
1355                    1360                1365

Lys Gly Pro Leu Pro Leu Arg Asp Asp Asn Gly Ile Val Leu Leu
1370                    1375                1380

Gly Glu Arg Ala Ala Lys Cys Arg Ala Tyr Ala Lys Ala Leu His
1385                    1390                1395

Tyr Lys Glu Leu Glu Phe Gln Lys Gly Pro Thr Pro Ala Ile Leu
1400                    1405                1410

Glu Ser Leu Ile Ser Ile Asn Asn Lys Leu Gln Gln Pro Glu Ala
1415                    1420                1425

Ala Ala Gly Val Leu Glu Tyr Ala Met Lys His Phe Gly Glu Leu
1430                    1435                1440

Glu Ile Gln Ala Thr Trp Tyr Glu Lys Leu His Glu Trp Glu Asp
1445                    1450                1455

Ala Leu Val Ala Tyr Asp Lys Lys Met Asp Thr Asn Lys Asp Asp
1460                    1465                1470

Pro Glu Leu Met Leu Gly Arg Met Arg Cys Leu Glu Ala Leu Gly
1475                    1480                1485

Glu Trp Gly Gln Leu His Gln Gln Cys Cys Glu Lys Trp Thr Leu
1490                    1495                1500

Val Asn Asp Glu Thr Gln Ala Lys Met Ala Arg Met Ala Ala Ala
1505                    1510                1515

Ala Ala Trp Gly Leu Gly Gln Trp Asp Ser Met Glu Glu Tyr Thr
1520                    1525                1530

Cys Met Ile Pro Arg Asp Thr His Asp Gly Ala Phe Tyr Arg Ala
1535                    1540                1545

Val Leu Ala Leu His Gln Asp Leu Phe Ser Leu Ala Gln Gln Cys
1550                    1555                1560

Ile Asp Lys Ala Arg Asp Leu Leu Asp Ala Glu Leu Thr Ala Met
1565                    1570                1575

Ala Gly Glu Ser Tyr Ser Arg Ala Tyr Gly Ala Met Val Ser Cys
1580                    1585                1590

His Met Leu Ser Glu Leu Glu Glu Val Ile Gln Tyr Lys Leu Val
1595                    1600                1605

Pro Glu Arg Arg Glu Ile Ile Arg Gln Ile Trp Trp Glu Arg Leu
1610                    1615                1620

Gln Gly Cys Gln Arg Ile Val Glu Asp Trp Gln Lys Ile Leu Met
1625                    1630                1635

```
Val Arg Ser Leu Val Val Ser Pro His Glu Asp Met Arg Thr Trp
    1640                1645                1650

Leu Lys Tyr Ala Ser Leu Cys Gly Lys Ser Gly Arg Leu Ala Leu
    1655                1660                1665

Ala His Lys Thr Leu Val Leu Leu Leu Gly Val Asp Pro Ser Arg
    1670                1675                1680

Gln Leu Asp His Pro Leu Pro Thr Val His Pro Gln Val Thr Tyr
    1685                1690                1695

Ala Tyr Met Lys Asn Met Trp Lys Ser Ala Arg Lys Ile Asp Ala
    1700                1705                1710

Phe Gln His Met Gln His Phe Val Gln Thr Met Gln Gln Gln Ala
    1715                1720                1725

Gln His Ala Ile Ala Thr Glu Asp Gln Gln His Lys Gln Glu Leu
    1730                1735                1740

His Lys Leu Met Ala Arg Cys Phe Leu Lys Leu Gly Glu Trp Gln
    1745                1750                1755

Leu Asn Leu Gln Gly Ile Asn Glu Ser Thr Ile Pro Lys Val Leu
    1760                1765                1770

Gln Tyr Tyr Ser Ala Ala Thr Glu His Asp Arg Ser Trp Tyr Lys
    1775                1780                1785

Ala Trp His Ala Trp Ala Val Met Asn Phe Glu Ala Val Leu His
    1790                1795                1800

Tyr Lys His Gln Asn Gln Ala Arg Asp Glu Lys Lys Lys Leu Arg
    1805                1810                1815

His Ala Ser Gly Ala Asn Ile Thr Asn Ala Thr Thr Ala Ala Thr
    1820                1825                1830

Thr Ala Ala Thr Ala Thr Thr Thr Ala Ser Thr Glu Gly Ser Asn
    1835                1840                1845

Ser Glu Ser Glu Ala Glu Ser Thr Glu Asn Ser Pro Thr Pro Ser
    1850                1855                1860

Pro Leu Gln Lys Lys Val Thr Glu Asp Leu Ser Lys Thr Leu Leu
    1865                1870                1875

Met Tyr Thr Val Pro Ala Val Gln Gly Phe Phe Arg Ser Ile Ser
    1880                1885                1890

Leu Ser Arg Gly Asn Asn Leu Gln Asp Thr Leu Arg Val Leu Thr
    1895                1900                1905

Leu Trp Phe Asp Tyr Gly His Trp Pro Asp Val Asn Glu Ala Leu
    1910                1915                1920

Val Glu Gly Val Lys Ala Ile Gln Ile Asp Thr Trp Leu Gln Val
    1925                1930                1935

Ile Pro Gln Leu Ile Ala Arg Ile Asp Thr Pro Arg Pro Leu Val
    1940                1945                1950

Gly Arg Leu Ile His Gln Leu Leu Thr Asp Ile Gly Arg Tyr His
    1955                1960                1965

Pro Gln Ala Leu Ile Tyr Pro Leu Thr Val Ala Ser Lys Ser Thr
    1970                1975                1980

Thr Thr Ala Arg His Asn Ala Ala Asn Lys Ile Leu Lys Asn Met
    1985                1990                1995

Cys Glu His Ser Asn Thr Leu Val Gln Gln Ala Met Met Val Ser
    2000                2005                2010

Glu Glu Leu Ile Arg Val Ala Ile Leu Trp His Glu Met Trp His
    2015                2020                2025

Glu Gly Leu Glu Glu Ala Ser Arg Leu Tyr Phe Gly Glu Arg Asn
```

-continued

```
            2030                2035                2040

Val Lys Gly Met Phe Glu Val Leu Glu Pro Leu His Ala Met Met
            2045                2050                2055

Glu Arg Gly Pro Gln Thr Leu Lys Glu Thr Ser Phe Asn Gln Ala
            2060                2065            2070

Tyr Gly Arg Asp Leu Met Glu Ala Gln Glu Trp Cys Arg Lys Tyr
        2075                2080                2085

Met Lys Ser Gly Asn Val Lys Asp Leu Thr Gln Ala Trp Asp Leu
        2090                2095            2100

Tyr Tyr His Val Phe Arg Arg Ile Ser Lys Gln Leu Pro Gln Leu
        2105                2110            2115

Thr Ser Leu Glu Leu Gln Tyr Val Ser Pro Lys Leu Leu Met Cys
        2120                2125            2130

Arg Asp Leu Glu Leu Ala Val Pro Gly Thr Tyr Asp Pro Asn Gln
        2135                2140            2145

Pro Ile Ile Arg Ile Gln Ser Ile Ala Pro Ser Leu Gln Val Ile
        2150                2155            2160

Thr Ser Lys Gln Arg Pro Arg Lys Leu Thr Leu Met Gly Ser Asn
        2165                2170            2175

Gly His Glu Phe Val Phe Leu Leu Lys Gly His Glu Asp Leu Arg
        2180                2185            2190

Gln Asp Glu Arg Val Met Gln Leu Phe Gly Leu Val Asn Thr Leu
        2195                2200            2205

Leu Ala Asn Asp Pro Thr Ser Leu Arg Lys Asn Leu Ser Ile Gln
        2210                2215            2220

Arg Tyr Ala Val Ile Pro Leu Ser Thr Asn Ser Gly Leu Ile Gly
        2225                2230            2235

Trp Val Pro His Cys Asp Thr Leu His Ala Leu Ile Arg Asp Tyr
        2240                2245            2250

Arg Glu Lys Lys Lys Ile Leu Leu Asn Ile Glu His Arg Ile Met
        2255                2260            2265

Leu Arg Met Ala Pro Asp Tyr Asp His Leu Thr Leu Met Gln Lys
        2270                2275            2280

Val Glu Val Phe Glu His Ala Val Asn Asn Thr Ala Gly Asp Asp
        2285                2290            2295

Leu Ala Lys Leu Leu Trp Leu Lys Ser Pro Ser Ser Glu Val Trp
        2300                2305            2310

Phe Asp Arg Arg Thr Asn Tyr Thr Arg Ser Leu Ala Val Met Ser
        2315                2320            2325

Met Val Gly Tyr Ile Leu Gly Leu Gly Asp Arg His Pro Ser Asn
        2330                2335            2340

Leu Met Leu Asp Arg Leu Ser Gly Lys Ile Leu His Ile Asp Phe
        2345                2350            2355

Gly Asp Cys Phe Glu Val Ala Met Thr Arg Glu Lys Phe Pro Glu
        2360                2365            2370

Lys Ile Pro Phe Arg Leu Thr Arg Met Leu Thr Asn Ala Met Glu
        2375                2380            2385

Val Thr Gly Leu Asp Gly Asn Tyr Arg Ile Thr Cys His Thr Val
        2390                2395            2400

Met Glu Val Leu Arg Glu His Lys Asp Ser Val Met Ala Val Leu
        2405                2410            2415

Glu Ala Phe Val Tyr Asp Pro Leu Leu Asn Trp Arg Leu Met Asp
        2420                2425            2430
```

```
Thr Asn Thr Lys Gly Asn Lys Arg Ser Arg Thr Arg Thr Asp Ser
        2435            2440                2445

Tyr Ser Ala Gly Gln Ser Val Glu Ile Leu Asp Gly Val Glu Leu
2450                2455                2460

Gly Glu Pro Ala His Lys Lys Thr Gly Thr Thr Val Pro Glu Ser
2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
2525                2530                2535

Cys Gln Cys Tyr Ile Gly Trp Cys Pro Phe Trp
    2540                2545

<210> SEQ ID NO 21
<211> LENGTH: 2549
<212> TYPE: PRT
<213> ORGANISM: Mus musculus

<400> SEQUENCE: 21

Met Leu Gly Thr Gly Pro Ala Val Ala Thr Ala Ser Ala Ala Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ser Thr Arg Ile Gly Arg Phe Ala Asn Tyr Leu Arg
            100                 105                 110

Asn Leu Leu Pro Ser Ser Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
```

-continued

```
                245                 250                 255
Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Pro Asn Ala Leu Val Gly Leu Leu Gly Tyr
                325                 330                 335

Ser Ser Pro Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Ser Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Thr Val Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
    530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Ala Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670
```

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
        690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940

Glu Phe Tyr Pro Ala Val Ser Met Val Ala Leu Met Arg Ile Phe Arg
945                 950                 955                 960

Asp Gln Ser Leu Ser His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val Ile Arg Val Cys Asp Gly Ala Ile
        995                 1000                1005

Arg Glu Phe Leu Phe Gln Gln Leu Gly Met Leu Val Ser Phe Val
    1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Val Ala Leu Gly Gly Glu Phe Lys
    1055                1060                1065

Leu Tyr Leu Pro Gln Leu Ile Pro His Met Leu Arg Val Phe Met
    1070                1075                1080

```
His Asp Asn Ser Gln Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Val Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Asp Pro Leu Ile Tyr Gln
    1220                1225                1230

His Arg Met Leu Arg Ser Ser Gln Gly Asp Ala Leu Ala Ser Gly
    1235                1240                1245

Pro Val Glu Thr Gly Pro Met Lys Lys Leu His Val Ser Thr Ile
    1250                1255                1260

Asn Leu Gln Lys Ala Trp Gly Ala Ala Arg Arg Val Ser Lys Asp
    1265                1270                1275

Asp Trp Leu Glu Trp Leu Arg Arg Leu Ser Leu Glu Leu Leu Lys
    1280                1285                1290

Asp Ser Ser Ser Pro Ser Leu Arg Ser Cys Trp Ala Leu Ala Gln
    1295                1300                1305

Ala Tyr Asn Pro Met Ala Arg Asp Leu Phe Asn Ala Ala Phe Val
    1310                1315                1320

Ser Cys Trp Ser Glu Leu Asn Glu Asp Gln Gln Asp Glu Leu Ile
    1325                1330                1335

Arg Ser Ile Glu Leu Ala Leu Thr Ser Gln Asp Ile Ala Glu Val
    1340                1345                1350

Thr Gln Thr Leu Leu Asn Leu Ala Glu Phe Met Glu His Ser Asp
    1355                1360                1365

Lys Gly Pro Leu Pro Leu Arg Asp Asp Asn Gly Ile Val Leu Leu
    1370                1375                1380

Gly Glu Arg Ala Ala Lys Cys Arg Ala Tyr Ala Lys Ala Leu His
    1385                1390                1395

Tyr Lys Glu Leu Glu Phe Gln Lys Gly Pro Thr Pro Ala Ile Leu
    1400                1405                1410

Glu Ser Leu Ile Ser Ile Asn Asn Lys Leu Gln Gln Pro Glu Ala
    1415                1420                1425

Ala Ser Gly Val Leu Glu Tyr Ala Met Lys His Phe Gly Glu Leu
    1430                1435                1440

Glu Ile Gln Ala Thr Trp Tyr Glu Lys Leu His Glu Trp Glu Asp
    1445                1450                1455

Ala Leu Val Ala Tyr Asp Lys Lys Met Asp Thr Asn Lys Glu Asp
    1460                1465                1470

Pro Glu Leu Met Leu Gly Arg Met Arg Cys Leu Glu Ala Leu Gly
```

-continued

```
            1475                1480                1485

Glu Trp Gly Gln Leu His Gln Gln Cys Cys Glu Lys Trp Thr Leu
    1490                1495                1500

Val Asn Asp Glu Thr Gln Ala Lys Met Ala Arg Met Ala Ala Ala
    1505                1510                1515

Ala Ala Trp Gly Leu Gly Gln Trp Asp Ser Met Glu Tyr Thr
    1520                1525                1530

Cys Met Ile Pro Arg Asp Thr His Asp Gly Ala Phe Tyr Arg Ala
    1535                1540                1545

Val Leu Ala Leu His Gln Asp Leu Phe Ser Leu Ala Gln Gln Cys
    1550                1555                1560

Ile Asp Lys Ala Arg Asp Leu Leu Asp Ala Glu Leu Thr Ala Met
    1565                1570                1575

Ala Gly Glu Ser Tyr Ser Arg Ala Tyr Gly Ala Met Val Ser Cys
    1580                1585                1590

His Met Leu Ser Glu Leu Glu Glu Val Ile Gln Tyr Lys Leu Val
    1595                1600                1605

Pro Glu Arg Arg Glu Ile Ile Arg Gln Ile Trp Trp Glu Arg Leu
    1610                1615                1620

Gln Gly Cys Gln Arg Ile Val Glu Asp Trp Gln Lys Ile Leu Met
    1625                1630                1635

Val Arg Ser Leu Val Val Ser Pro His Glu Asp Met Arg Thr Trp
    1640                1645                1650

Leu Lys Tyr Ala Ser Leu Cys Gly Lys Ser Gly Arg Leu Ala Leu
    1655                1660                1665

Ala His Lys Thr Leu Val Leu Leu Leu Gly Val Asp Pro Ser Arg
    1670                1675                1680

Gln Leu Asp His Pro Leu Pro Thr Ala His Pro Gln Val Thr Tyr
    1685                1690                1695

Ala Tyr Met Lys Asn Met Trp Lys Ser Ala Arg Lys Ile Asp Ala
    1700                1705                1710

Phe Gln His Met Gln His Phe Val Gln Thr Met Gln Gln Gln Ala
    1715                1720                1725

Gln His Ala Ile Ala Thr Glu Asp Gln Gln His Lys Gln Glu Leu
    1730                1735                1740

His Lys Leu Met Ala Arg Cys Phe Leu Lys Leu Gly Glu Trp Gln
    1745                1750                1755

Leu Asn Leu Gln Gly Ile Asn Glu Ser Thr Ile Pro Lys Val Leu
    1760                1765                1770

Gln Tyr Tyr Ser Ala Ala Thr Glu His Asp Arg Ser Trp Tyr Lys
    1775                1780                1785

Ala Trp His Ala Trp Ala Val Met Asn Phe Glu Ala Val Leu His
    1790                1795                1800

Tyr Lys His Gln Asn Gln Ala Arg Asp Glu Lys Lys Lys Leu Arg
    1805                1810                1815

His Ala Ser Gly Ala Asn Ile Thr Asn Ala Thr Thr Ala Ala Thr
    1820                1825                1830

Thr Ala Ala Ser Ala Ala Ala Ala Thr Ser Thr Glu Gly Ser Asn
    1835                1840                1845

Ser Glu Ser Glu Ala Glu Ser Asn Glu Asn Ser Pro Thr Pro Ser
    1850                1855                1860

Pro Leu Gln Lys Lys Val Thr Glu Asp Leu Ser Lys Thr Leu Leu
    1865                1870                1875
```

```
Leu Tyr Thr Val Pro Ala Val Gln Gly Phe Phe Arg Ser Ile Ser
    1880            1885                1890

Leu Ser Arg Gly Asn Asn Leu Gln Asp Thr Leu Arg Val Leu Thr
    1895            1900                1905

Leu Trp Phe Asp Tyr Gly His Trp Pro Asp Val Asn Glu Ala Leu
    1910            1915                1920

Val Glu Gly Val Lys Ala Ile Gln Ile Asp Thr Trp Leu Gln Val
    1925            1930                1935

Ile Pro Gln Leu Ile Ala Arg Ile Asp Thr Pro Arg Pro Leu Val
    1940            1945                1950

Gly Arg Leu Ile His Gln Leu Leu Thr Asp Ile Gly Arg Tyr His
    1955            1960                1965

Pro Gln Ala Leu Ile Tyr Pro Leu Thr Val Ala Ser Lys Ser Thr
    1970            1975                1980

Thr Thr Ala Arg His Asn Ala Ala Asn Lys Ile Leu Lys Asn Met
    1985            1990                1995

Cys Glu His Ser Asn Thr Leu Val Gln Gln Ala Met Met Val Ser
    2000            2005                2010

Glu Glu Leu Ile Arg Val Ala Ile Leu Trp His Glu Met Trp His
    2015            2020                2025

Glu Gly Leu Glu Glu Ala Ser Arg Leu Tyr Phe Gly Glu Arg Asn
    2030            2035                2040

Val Lys Gly Met Phe Glu Val Leu Glu Pro Leu His Ala Met Met
    2045            2050                2055

Glu Arg Gly Pro Gln Thr Leu Lys Glu Thr Ser Phe Asn Gln Ala
    2060            2065                2070

Tyr Gly Arg Asp Leu Met Glu Ala Gln Glu Trp Cys Arg Lys Tyr
    2075            2080                2085

Met Lys Ser Gly Asn Val Lys Asp Leu Thr Gln Ala Trp Asp Leu
    2090            2095                2100

Tyr Tyr His Val Phe Arg Arg Ile Ser Lys Gln Leu Pro Gln Leu
    2105            2110                2115

Thr Ser Leu Glu Leu Gln Tyr Val Ser Pro Lys Leu Leu Met Cys
    2120            2125                2130

Arg Asp Leu Glu Leu Ala Val Pro Gly Thr Tyr Asp Pro Asn Gln
    2135            2140                2145

Pro Ile Ile Arg Ile Gln Ser Ile Ala Pro Ser Leu Gln Val Ile
    2150            2155                2160

Thr Ser Lys Gln Arg Pro Arg Lys Leu Thr Leu Met Gly Ser Asn
    2165            2170                2175

Gly His Glu Phe Val Phe Leu Leu Lys Gly His Glu Asp Leu Arg
    2180            2185                2190

Gln Asp Glu Arg Val Met Gln Leu Phe Gly Leu Val Asn Thr Leu
    2195            2200                2205

Leu Ala Asn Asp Pro Thr Ser Leu Arg Lys Asn Leu Ser Ile Gln
    2210            2215                2220

Arg Tyr Ala Val Ile Pro Leu Ser Thr Asn Ser Gly Leu Ile Gly
    2225            2230                2235

Trp Val Pro His Cys Asp Thr Leu His Ala Leu Ile Arg Asp Tyr
    2240            2245                2250

Arg Glu Lys Lys Lys Ile Leu Leu Asn Ile Glu His Arg Ile Met
    2255            2260                2265
```

-continued

```
Leu Arg Met Ala Pro Asp Tyr Asp His Leu Thr Leu Met Gln Lys
    2270                2275                2280

Val Glu Val Phe Glu His Ala Val Asn Asn Thr Ala Gly Asp Asp
    2285                2290                2295

Leu Ala Lys Leu Leu Trp Leu Lys Ser Pro Ser Ser Glu Val Trp
    2300                2305                2310

Phe Asp Arg Arg Thr Asn Tyr Thr Arg Ser Leu Ala Val Met Ser
    2315                2320                2325

Met Val Gly Tyr Ile Leu Gly Leu Gly Asp Arg His Pro Ser Asn
    2330                2335                2340

Leu Met Leu Asp Arg Leu Ser Gly Lys Ile Leu His Ile Asp Phe
    2345                2350                2355

Gly Asp Cys Phe Glu Val Ala Met Thr Arg Glu Lys Phe Pro Glu
    2360                2365                2370

Lys Ile Pro Phe Arg Leu Thr Arg Met Leu Thr Asn Ala Met Glu
    2375                2380                2385

Val Thr Gly Leu Asp Gly Asn Tyr Arg Thr Thr Cys His Thr Val
    2390                2395                2400

Met Glu Val Leu Arg Glu His Lys Asp Ser Val Met Ala Val Leu
    2405                2410                2415

Glu Ala Phe Val Tyr Asp Pro Leu Leu Asn Trp Arg Leu Met Asp
    2420                2425                2430

Thr Asn Thr Lys Gly Asn Lys Arg Ser Arg Thr Arg Thr Asp Ser
    2435                2440                2445

Tyr Ser Ala Gly Gln Ser Val Glu Ile Leu Asp Gly Val Glu Leu
    2450                2455                2460

Gly Glu Pro Ala His Lys Lys Ala Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 22
<211> LENGTH: 108
<212> TYPE: PRT
<213> ORGANISM: Homo sapiens

<400> SEQUENCE: 22

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80
```

```
Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 23
<211> LENGTH: 108
<212> TYPE: PRT
<213> ORGANISM: Mus musculus

<400> SEQUENCE: 23

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Thr Leu Gly Lys Gln Glu Val Ile Arg Gly Trp Glu Glu Gly Val
    50                  55                  60

Ala Gln Met Ser Val Gly Gln Arg Ala Lys Leu Ile Ile Ser Ser Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 24
<211> LENGTH: 245
<212> TYPE: PRT
<213> ORGANISM: Escherichia virus T4 (T4)

<400> SEQUENCE: 24

Met Lys Ser Gly Ile Tyr Gln Ile Lys Asn Thr Leu Asn Asn Lys Val
1               5                   10                  15

Tyr Val Gly Ser Ala Lys Asp Phe Glu Lys Arg Trp Lys Arg His Phe
            20                  25                  30

Lys Asp Leu Glu Lys Gly Cys His Ser Ser Ile Lys Leu Gln Arg Ser
        35                  40                  45

Phe Asn Lys His Gly Asn Val Phe Glu Cys Ser Ile Leu Glu Glu Ile
    50                  55                  60

Pro Tyr Glu Lys Asp Leu Ile Ile Glu Arg Glu Asn Phe Trp Ile Lys
65                  70                  75                  80

Glu Leu Asn Ser Lys Ile Asn Gly Tyr Asn Ile Ala Asp Ala Thr Phe
                85                  90                  95

Gly Asp Thr Cys Ser Thr His Pro Leu Lys Glu Ile Ile Lys Lys
            100                 105                 110

Arg Ser Glu Thr Val Lys Ala Lys Met Leu Lys Leu Gly Pro Asp Gly
        115                 120                 125

Arg Lys Ala Leu Tyr Ser Lys Pro Gly Ser Lys Asn Gly Arg Trp Asn
    130                 135                 140

Pro Glu Thr His Lys Phe Cys Lys Cys Gly Val Arg Ile Gln Thr Ser
145                 150                 155                 160

Ala Tyr Thr Cys Ser Lys Cys Arg Asn Arg Ser Gly Glu Asn Asn Ser
                165                 170                 175

Phe Phe Asn His Lys His Ser Asp Ile Thr Lys Ser Lys Ile Ser Glu
            180                 185                 190
```

```
Lys Met Lys Gly Lys Lys Pro Ser Asn Ile Lys Ile Ser Cys Asp
            195                 200                 205

Gly Val Ile Phe Asp Cys Ala Ala Asp Ala Ala Arg His Phe Lys Ile
210                 215                 220

Ser Ser Gly Leu Val Thr Tyr Arg Val Lys Ser Asp Lys Trp Asn Trp
225                 230                 235                 240

Phe Tyr Ile Asn Ala
                245

<210> SEQ ID NO 25
<211> LENGTH: 235
<212> TYPE: PRT
<213> ORGANISM: Saccharomyces cerevisiae

<400> SEQUENCE: 25

Met Lys Asn Ile Lys Lys Asn Gln Val Met Asn Leu Gly Pro Asn Ser
1               5                   10                  15

Lys Leu Leu Lys Glu Tyr Lys Ser Gln Leu Ile Glu Leu Asn Ile Glu
            20                  25                  30

Gln Phe Glu Ala Gly Ile Gly Leu Ile Leu Gly Asp Ala Tyr Ile Arg
        35                  40                  45

Ser Arg Asp Glu Gly Lys Thr Tyr Cys Met Gln Phe Glu Trp Lys Asn
50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
            85                  90                  95

Ile Thr Trp Gly Ala Gln Thr Phe Lys His Gln Ala Phe Asn Lys Leu
        100                 105                 110

Ala Asn Leu Phe Ile Val Asn Asn Lys Lys Thr Ile Pro Asn Asn Leu
        115                 120                 125

Val Glu Asn Tyr Leu Thr Pro Met Ser Leu Ala Tyr Trp Phe Met Asp
        130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Leu Ile Phe
        195                 200                 205

Tyr Asn Leu Ile Lys Pro Tyr Leu Ile Pro Gln Met Met Tyr Lys Leu
        210                 215                 220

Pro Asn Thr Ile Ser Ser Glu Thr Phe Leu Lys
225                 230                 235

<210> SEQ ID NO 26
<211> LENGTH: 583
<212> TYPE: PRT
<213> ORGANISM: Planomicrobium okeanokoites

<400> SEQUENCE: 26

Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30
```

```
Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
 50                  55                  60

Gln His Asp Leu Ile Tyr Thr Tyr Lys Glu Leu Val Gly Thr Gly Thr
 65                  70                  75                  80

Ser Ile Arg Ser Glu Ala Pro Cys Asp Ala Ile Gln Ala Thr Ile
                 85                  90                  95

Ala Asp Gln Gly Asn Lys Lys Gly Tyr Ile Asp Asn Trp Ser Ser Asp
                100                 105                 110

Gly Phe Leu Arg Trp Ala His Ala Leu Gly Phe Ile Glu Tyr Ile Asn
             115                 120                 125

Lys Ser Asp Ser Phe Val Ile Thr Asp Val Gly Leu Ala Tyr Ser Lys
130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Glu Asp Gly
                165                 170                 175

Gln His Leu Thr Lys Phe Asp Leu Gly Lys Asn Leu Gly Phe Ser Gly
             180                 185                 190

Glu Ser Gly Phe Thr Ser Leu Pro Glu Gly Ile Leu Leu Asp Thr Leu
         195                 200                 205

Ala Asn Ala Met Pro Lys Asp Lys Gly Glu Ile Arg Asn Asn Trp Glu
         210                 215                 220

Gly Ser Ser Asp Lys Tyr Ala Arg Met Ile Gly Gly Trp Leu Asp Lys
225                 230                 235                 240

Leu Gly Leu Val Lys Gln Gly Lys Lys Glu Phe Ile Ile Pro Thr Leu
                245                 250                 255

Gly Lys Pro Asp Asn Lys Glu Phe Ile Ser His Ala Phe Lys Ile Thr
             260                 265                 270

Gly Glu Gly Leu Lys Val Leu Arg Arg Ala Lys Gly Ser Thr Lys Phe
         275                 280                 285

Thr Arg Val Pro Lys Arg Val Tyr Trp Glu Met Leu Ala Thr Asn Leu
         290                 295                 300

Thr Asp Lys Glu Tyr Val Arg Thr Arg Arg Ala Leu Ile Leu Glu Ile
305                 310                 315                 320

Leu Ile Lys Ala Gly Ser Leu Lys Ile Glu Gln Ile Gln Asp Asn Leu
                325                 330                 335

Lys Lys Leu Gly Phe Asp Glu Val Ile Glu Thr Ile Glu Asn Asp Ile
             340                 345                 350

Lys Gly Leu Ile Asn Thr Gly Ile Phe Ile Glu Ile Lys Gly Arg Phe
         355                 360                 365

Tyr Gln Leu Lys Asp His Ile Leu Gln Phe Val Ile Pro Asn Arg Gly
         370                 375                 380

Val Thr Lys Gln Leu Val Lys Ser Glu Leu Glu Lys Lys Ser Glu
385                 390                 395                 400

Leu Arg His Lys Leu Lys Tyr Val Pro His Glu Tyr Ile Glu Leu Ile
                405                 410                 415

Glu Ile Ala Arg Asn Ser Thr Gln Asp Arg Ile Leu Glu Met Lys Val
             420                 425                 430

Met Glu Phe Phe Met Lys Val Tyr Gly Tyr Arg Gly Lys His Leu Gly
         435                 440                 445
```

Gly Ser Arg Lys Pro Asp Gly Ala Ile Tyr Thr Val Gly Ser Pro Ile
            450                 455                 460

Asp Tyr Gly Val Ile Val Asp Thr Lys Ala Tyr Ser Gly Gly Tyr Asn
465                 470                 475                 480

Leu Pro Ile Gly Gln Ala Asp Glu Met Gln Arg Tyr Val Glu Asn
            485                 490                 495

Gln Thr Arg Asn Lys His Ile Asn Pro Asn Glu Trp Trp Lys Val Tyr
            500                 505                 510

Pro Ser Ser Val Thr Glu Phe Lys Phe Leu Phe Val Ser Gly His Phe
            515                 520                 525

Lys Gly Asn Tyr Lys Ala Gln Leu Thr Arg Leu Asn His Ile Thr Asn
            530                 535                 540

Cys Asn Gly Ala Val Leu Ser Val Glu Glu Leu Leu Ile Gly Glu
545                 550                 555                 560

Met Ile Lys Ala Gly Thr Leu Thr Leu Glu Glu Val Arg Arg Lys Phe
            565                 570                 575

Asn Asn Gly Glu Ile Asn Phe
            580

<210> SEQ ID NO 27
<211> LENGTH: 586
<212> TYPE: PRT
<213> ORGANISM: Saccharomyces cerevisiae S288C

<400> SEQUENCE: 27

Met Leu Ser Glu Asn Thr Thr Ile Leu Met Ala Asn Gly Glu Ile Lys
1               5                   10                  15

Asp Ile Ala Asn Val Thr Ala Asn Ser Tyr Val Met Cys Ala Asp Gly
                20                  25                  30

Ser Ala Ala Arg Val Ile Asn Val Thr Gln Gly Tyr Gln Lys Ile Tyr
            35                  40                  45

Asn Ile Gln Gln Lys Thr Lys His Arg Ala Phe Glu Gly Glu Pro Gly
50                  55                  60

Arg Leu Asp Pro Arg Arg Thr Val Tyr Gln Arg Leu Ala Leu Gln
65                  70                  75                  80

Cys Thr Ala Gly His Lys Leu Ser Val Arg Val Pro Thr Lys Pro Leu
                85                  90                  95

Leu Glu Lys Ser Gly Arg Asn Ala Thr Lys Tyr Lys Val Arg Trp Arg
            100                 105                 110

Asn Leu Gln Gln Cys Gln Thr Leu Asp Gly Arg Ile Ile Ile Pro
            115                 120                 125

Lys Asn His His Lys Thr Phe Pro Met Thr Val Glu Gly Glu Phe Ala
130                 135                 140

Ala Lys Arg Phe Ile Glu Glu Met Glu Arg Ser Lys Gly Glu Tyr Phe
145                 150                 155                 160

Asn Phe Asp Ile Glu Val Arg Asp Leu Asp Tyr Leu Asp Ala Gln Leu
                165                 170                 175

Arg Ile Ser Ser Cys Ile Arg Phe Gly Pro Val Leu Ala Gly Asn Gly
            180                 185                 190

Val Leu Ser Lys Phe Leu Thr Gly Arg Ser Asp Leu Val Thr Pro Ala
            195                 200                 205

Val Lys Ser Met Ala Trp Met Leu Gly Leu Trp Leu Gly Asp Ser Thr
210                 215                 220

Thr Lys Glu Pro Glu Ile Ser Val Asp Ser Leu Asp Pro Lys Leu Met
225                 230                 235                 240

Glu Ser Leu Arg Glu Asn Ala Lys Ile Trp Gly Leu Tyr Leu Thr Val
            245                 250                 255

Cys Asp Asp His Val Pro Leu Arg Ala Lys His Val Arg Leu His Tyr
            260                 265                 270

Gly Asp Gly Pro Asp Glu Asn Arg Lys Thr Arg Asn Leu Arg Lys Asn
            275                 280                 285

Asn Pro Phe Trp Lys Ala Val Thr Ile Leu Lys Phe Lys Arg Asp Leu
            290                 295                 300

Asp Gly Glu Lys Gln Ile Pro Glu Phe Met Tyr Gly Glu His Ile Glu
305                 310                 315                 320

Val Arg Glu Ala Phe Leu Ala Gly Leu Ile Asp Ser Asp Gly Tyr Val
            325                 330                 335

Val Lys Lys Gly Glu Gly Pro Glu Ser Tyr Lys Ile Ala Ile Gln Thr
            340                 345                 350

Val Tyr Ser Ser Ile Met Asp Gly Ile Val His Ile Ser Arg Ser Leu
            355                 360                 365

Gly Met Ser Ala Thr Val Thr Thr Arg Ser Ala Arg Glu Glu Ile Ile
            370                 375                 380

Glu Gly Arg Lys Val Gln Cys Gln Phe Thr Tyr Asp Cys Asn Val Ala
385                 390                 395                 400

Gly Gly Thr Thr Ser Gln Asn Val Leu Ser Tyr Cys Arg Ser Gly His
            405                 410                 415

Lys Thr Arg Glu Val Pro Pro Ile Ile Lys Arg Glu Pro Val Tyr Phe
            420                 425                 430

Ser Phe Thr Asp Asp Phe Gln Gly Glu Ser Thr Val Tyr Gly Leu Thr
            435                 440                 445

Ile Glu Gly His Lys Asn Phe Leu Leu Gly Asn Lys Ile Glu Val Lys
            450                 455                 460

Ser Cys Arg Gly Cys Cys Val Gly Glu Gln Leu Lys Ile Ser Gln Lys
465                 470                 475                 480

Lys Asn Leu Lys His Cys Val Ala Cys Pro Arg Lys Gly Ile Lys Tyr
            485                 490                 495

Phe Tyr Lys Asp Trp Ser Gly Lys Asn Arg Val Cys Ala Arg Cys Tyr
            500                 505                 510

Gly Arg Tyr Lys Phe Ser Gly His His Cys Ile Asn Cys Lys Tyr Val
            515                 520                 525

Pro Glu Ala Arg Glu Val Lys Lys Ala Lys Asp Lys Gly Glu Lys Leu
            530                 535                 540

Gly Ile Thr Pro Glu Gly Leu Pro Val Lys Gly Pro Glu Cys Ile Lys
545                 550                 555                 560

Cys Gly Gly Ile Leu Gln Phe Asp Ala Val Arg Gly Pro His Lys Ser
            565                 570                 575

Cys Gly Asn Asn Ala Gly Ala Arg Ile Cys
            580                 585

<210> SEQ ID NO 28
<211> LENGTH: 200
<212> TYPE: DNA
<213> ORGANISM: Artificial Sequence
<220> FEATURE:
<223> OTHER INFORMATION: Synthetic - Primer

<400> SEQUENCE: 28
gttaagattt acccttctcc agagacaatc gaaatcatta aggacaaata cagacagaaa    60

```
gaacatttgg tgcaacatgg tgttgcagtt gcagactctg ttagcgttga aagcaccgag    120
acagcattgc aaaatgttgg tttgaaattt ggtttcccat ttatgctgaa gtccaaaact    180
gtttctccct tccctgatag                                                 200
```

<210> SEQ ID NO 29
<211> LENGTH: 200
<212> TYPE: DNA
<213> ORGANISM: Artificial Sequence
<220> FEATURE:
<223> OTHER INFORMATION: Synthetic - Primer

<400> SEQUENCE: 29

```
aaaaacattt ctacaccaaa aatgcctgca cctggaaaag tagaaaccgc cttttagct    60 aaaaggttgg cctttgtttg aatagtatca ttcactcttg caggtgcgta acagtatga    120 cagatattat ccttgtggat cgtttcaacg gttggataag agaaaatttc tccatccaag    180
atacgcggaa caatcaatcg                                                 200
```

<210> SEQ ID NO 30
<211> LENGTH: 200
<212> TYPE: DNA
<213> ORGANISM: Artificial Sequence
<220> FEATURE:
<223> OTHER INFORMATION: Synthetic - Primer

<400> SEQUENCE: 30

```
tttattacct gacggtgaac tgttaatcaa tgaaattgca ccaagacctc acaattctgg    60
ccattatacg attgatgctt gcgtcacttc tcagtttgaa gcacatatta gagctatttc    120
tggattgcct atgcccaaaa attttacttg cttttctact ccccaaacaa atgccattat    180
gtttctccct tccctgatag                                                 200
```

<210> SEQ ID NO 31
<211> LENGTH: 200
<212> TYPE: DNA
<213> ORGANISM: Artificial Sequence
<220> FEATURE:
<223> OTHER INFORMATION: Synthetic - Primer

<400> SEQUENCE: 31

```
acttctttaa gatattacaa ccagcagaca tgacaggtaa atccgaatct gaacccatta    60
taacacccac taatggagct ttagaggtgc ctgaaaccgc attttctgtt gattttgtta    120
tcggaaggcc accagagccc tcaatgtatg caagtttacg ttcacaatca gacatagaag    180
atacgcggaa caatcaatcg                                                 200
```

<210> SEQ ID NO 32
<211> LENGTH: 200
<212> TYPE: DNA
<213> ORGANISM: Artificial Sequence
<220> FEATURE:
<223> OTHER INFORMATION: Synthetic - Primer

<400> SEQUENCE: 32

```
tgcttgcgtc acttctcagt ttgaagcaca tattagagct atttctggat tgcctatgcc    60 caaaatttt acttgctttt ctactcccca acaaatgcc attatgctca atattttagg    120
gtctgatgtg ccaaatggcg aacttgaact tgtagaaga gcacttgaaa ctacaagcgc    180
gtttctccct tccctgatag                                                 200
```

```
<210> SEQ ID NO 33
<211> LENGTH: 200
<212> TYPE: DNA
<213> ORGANISM: Artificial Sequence
<220> FEATURE:
<223> OTHER INFORMATION: Synthetic - Primer

<400> SEQUENCE: 33
cctcaatcgc atacttggcc atcctttgtg gggttctatg tgctgacaca atggtgactt    60
caaacggaac accaaacttc tttaagatat tacaaccagc agacatgaca ggtaaatccg   120
aatctgaacc cattataaca cccactaatg gagctttaga ggtgcctgaa accgcattag   180
atacgcggaa caatcaatcg                                               200

<210> SEQ ID NO 34
<211> LENGTH: 649
<212> TYPE: DNA
<213> ORGANISM: Artificial Sequence
<220> FEATURE:
<223> OTHER INFORMATION: Synthetic - Guide#1

<400> SEQUENCE: 34
cacaaaacac acaaacaaac acatgctagc cagagaagca ttagaagttt tgcacaatag    60
acctttatat gcagataaac agacttagtg ggtattaaaa tgttggtcaa tcttctgccg   120
tcttgattta aaagcacttc tcttttacta ttgtaagacg gaatatgcat gcaagatcgc   180
tttagttggt tgaatgtctc tttctttgtg ttgtggtttg ttcgtttttt tctaatttgg   240
aatattataa gaaacgttgt tttcttgcaa cattttgaaa tggtcattca aaaagctgga   300
ttcggtacca cttttctttt taccttgtct tctaagctct gttaaatttc ttgatggggt   360
ccagttaaac caaccccaa gttggtttat gtgagccttg tctctttttt ggatgaatag    420
tagcttagat agtgatagtt attattatga ctgatggaat ctacttaaaa atggattcca   480
ttttttgtct actgtaattg aattcttttt ggtacacttt ttggctgcat tgttatcctt   540
gaaagcactt acaatgttta aactttgcga atgactgaaa cagaaaagaa ataaaacgac   600
tgtacctgaa ctattgttga acaatatta aaacgtattc ctgaaacag                649

<210> SEQ ID NO 35
<211> LENGTH: 684
<212> TYPE: DNA
<213> ORGANISM: Artificial Sequence
<220> FEATURE:
<223> OTHER INFORMATION: Synthetic - Guide#2

<400> SEQUENCE: 35
cacaaaacac acaaacaaac acatgctagc gaagagcact tgaaactaca agcgcttctg    60
tctatcttta cgggataaac agacttagtg ggtattaaaa tgttggtcaa tcttctgccg   120
tcttgattta aaagcacttc tcttttacta ttgtaagacg gaatatgcat gcaagatcgc   180
tttagttggt tgaatgtctc tttctttgtg ttgtggtttg ttcgtttttt tctaatttgg   240
aatattataa gaaacgttgt tttcttgcaa cattttgaaa tggtcattca aaaagctgga   300
ttcggtacca cttttctttt taccttgtct tctaagctct gttaaatttc ttgatggggt   360
ccagttaaac caaccccaa gttggtttat gtgagccttg tctctttttt ggatgaatag    420
tagcttagat agtgatagtt attattatga ctgatggaat ctacttaaaa atggattcca   480
ttttttgtct actgtaattg aattcttttt ggtacacttt ttggctgcat tgttatcctt   540
gaaagcactt acaatgttta aactttgcga atgactgaaa cagaaaagaa ataaaacgac   600
```

-continued

```
tgtacctgaa ctattgttga aacaatatta aaacgtattc ctgaaacaga ttaaactcct        660
aggacaggcc ccttttcctt tgtc                                              684

<210> SEQ ID NO 36
<211> LENGTH: 684
<212> TYPE: DNA
<213> ORGANISM: Artificial Sequence
<220> FEATURE:
<223> OTHER INFORMATION: Synthetic - Guide#3

<400> SEQUENCE: 36
cacaaaacac acaaacaaac acatgctagc gtttacgttc acaatcagac atagaacccg        60
aaacaatgtt aacattaaac agacttagtg ggtattaaaa tgttggtcaa tcttctgccg       120
tcttgattta aaagcacttc tcttttacta ttgtaagacg gaatatgcat gcaagatcgc       180
tttagttggt tgaatgtctc tttctttgtg ttgtggtttg ttcgtttttt tctaatttgg       240
aatattataa gaaacgttgt tttcttgcaa cattttgaaa tggtcattca aaaagctgga       300
ttcggtacca cttttctttt taccttgtct tctaagctct gttaaatttc ttgatggggt       360
ccagttaaac caaccccccaa gttggtttat gtgagccttg tctctttttt ggatgaatag       420
tagcttagat agtgatagtt attattatga ctgatggaat ctacttaaaa atggattcca       480 tttttttgtct actgtaattg aattctttt ggtacacttt ttggctgcat tgttatcctt       540
gaaagcactt acaatgttta aactttgcga atgactgaaa cagaaaagaa ataaaacgac       600
tgtacctgaa ctattgttga aacaatatta aaacgtattc ctgaaacaga ttaaactcct       660
aggacaggcc ccttttcctt tgtc                                              684
```

GENOME EDITING SYSTEM

CROSS-REFERENCE TO RELATED APPLICATIONS

This application is a national phase application of International Application No. PCT/US2018/033496, filed May 18, 2018, entitled "GENOME EDITING SYSTEM", which claims the benefit of U.S. Provisional Patent Application No. 62/508,040, filed May 18, 2017, entitled "GENOME EDITING SYSTEM", each of which is hereby incorporated by reference in its entirety.

INCORPORATION BY REFERENCE OF SEQUENCE LISTING

A Sequence Listing is provided herewith as a text file, "N00499_ST25.txt" created on Sep. 8, 2021 and having a size of 113 kb. The contents of the text file are incorporated by reference herein in their entirety.

BACKGROUND

The general strategy in genomic engineering using site-specific nucleases is to select a target nucleotide sequence in the genome, generate a nuclease construct directed at the selected target, deliver the construct to the cell nucleus, and analyze the produced mutations. Nucleases make single- or double-strand breaks in a target site that are repaired by the cell through one of two possible mechanisms: nonhomologous end joining (NHEJ), during which errors can occur that result in indel type (insertions, deletions) mutations in the target locus, or homologous recombination (HR), in which an intact homolog serves as a template to restore the original DNA structure. In particular, the following mutations can be produced using site-specific nucleases: NHEJ in the absence of donor DNA mediates deletions or insertions of several nucleotides at the breakage point; in the presence of donor DNA, fragments of more than 14 kb can be inserted through NHEJ-mediated ligation; simultaneous introduction of several double-strand breaks may lead to deletions, inversions, or translocations of the DNA regions located between these breaks; and homologous recombination in the presence of donor DNA with homology arms flanking the donor DNA to be inserted, leads to insertion of nucleotides (or a deletion of the existing sequence), thus altering the existing genomic sequence.

The TALEN genome editing system is based on a naturally occurring system. Effector proteins (transcription activator-like effectors, TALEs) are capable of DNA binding and activating the expression of target genes via mimicking eukaryotic transcription factors. TALE proteins are composed of a central domain responsible for DNA binding, a nuclear localization signal, and a domain that activates the target gene transcription. Chimeric TALEN nucleases encode the DNA-binding domain of TALE. Because the DNA-binding domain of TALEN consists of almost identical repeats, and to increase the efficiency and to accelerate the assembly process, type IIS restriction endonucleases are used to hydrolyze DNA at a fixed distance from the recognition site. A double-strand break can be introduced in any region of the genome with known recognition sites of the DNA-binding domains using chimeric TALEN nucleases. TALEN proteins are methylation sensitive and a specific chimera with defined spacing may be needed for each target site.

Another genome editing system, CRISPR, employs non-coding RNAs and Cas proteins (CRISPR associated). In contrast to the chimeric TALEN proteins, recognition by the CRISPR/Cas system is carried out via the complementary interaction between a non-coding RNA and the target site DNA. In this case, a complex of non-coding RNA and Cas proteins, which have nuclease activity, is formed. In particular, for cleavage of DNA in vitro and in bacterial cells using CRISPR/Cas9, the following components are necessary and sufficient: non-coding RNAs (tracrRNA and pre-crRNA), RNase polymerase III, and the Cas9 protein. Instead of two non-coding RNAs, a single chimeric sgRNA is often introduced, in which mature crRNA is fused with a part of the tracrRNA through the synthetic "stem-loop" structure to simulate the natural crRNA-tracrRNA duplex. The CRISPR system is dependent on protospacer adjacent motifs (PAM) in the target DNA.

Existing genome editing tools, such as TALENS and CRISPR, offer several options to enable modification of genes within multiple research organisms. Each of the currently available tools does, however, have limitations. TALENs can be custom designed to target virtually any DNA sequence. Nevertheless, they are large proteins and the customization step requires engineering the large effector protein, which can be costly or time consuming. CRISPR/Cas systems depend upon the existence of PAM motifs nearby the sequence of interest to enable targeting that specific locus within the genome. If the target locus does not contain a PAM site recognized by the Cas protein, the site cannot be engineered.

SUMMARY

The system described herein uses specific RNA components and specific polypeptide components that may be altered so that they retain at least one of their original functions but also perform a new function, which together allows for genome editing. A "RNA component" as used herein includes a targeting RNA sequence and a RNA segment that binds a specific polypeptide (protein) (a RNA component containing both targeting sequence and a protein binding segment may also be referred to as guide RNA or gRNA). A "polypeptide component" as used herein includes an endonuclease and a RNA-binding protein, and a "DNA component" as used herein includes a DNA molecule (also known as donor DNA) having at least one contiguous portion of a target sequence, e.g., a genomic target sequence ("locus"). In one embodiment, the DNA component has at least one nucleotide sequence capable of binding (hybridization via complementarity) the genomic target sequence at the locus. The at least one nucleotide sequence that is capable of binding the genomic target sequence at the locus may have a sequence that differs from the genomic target sequence, e.g., differs at one or more nucleotides (e.g., one or more nucleotide substitutions, insertions or deletions, or any combination thereof) from the genomic target sequence, resulting in at least one homology "arm." The homology arm may be linked to heterologous sequence (e.g., one that does not bind to the target sequence at the locus). The DNA component may have two different nucleotide sequences that are each capable of binding the target sequence at the locus, at least one of which may have a sequence that differs from the target sequence, e.g., differs at one or more nucleotides, resulting in two homology "arms." The two homology arms may be separated a heterologous sequence. The heterologous sequence may encode a protein, e.g., an enzyme, and/or a screenable or selectable marker.

A system for editing of a target sequence at a locus in a host cell is provided. In one embodiment, the system includes a first isolated DNA molecule comprising a first DNA segment encoding a targeting RNA sequence (or a first isolated RNA molecule comprising a first RNA segment comprising the targeting RNA sequence); a second isolated DNA molecule comprising a second DNA segment encoding a second RNA segment that binds a protein, for example, that binds a protein having at least 80% amino acid sequence identity to SEQ ID NO:5 or binds a portion of the protein having at least 80% amino acid sequence identity to SEQ ID NO:5, portions including those with at least 80% amino acid sequence identity to SEQ ID NO:6 or 7 (or a second isolated RNA molecule comprising a second RNA segment comprising the RNA segment that binds the protein or a portion thereof); a third isolated DNA molecule comprising a third DNA segment encoding an endonuclease or a portion thereof with nuclease activity (or a third isolated RNA molecule comprising a third RNA segment encoding the endonuclease or the portion thereof), or an isolated polypeptide comprising the endonuclease or the portion thereof; a fourth isolated DNA molecule comprising a fourth DNA segment encoding the protein that binds the RNA segment (or a fourth isolated RNA molecule comprising a fourth RNA segment encoding the protein that binds the RNA segment), or an isolated polypeptide comprising the protein that binds the RNA segment; and a fifth double stranded DNA molecule comprising DNA comprising at least one nucleotide sequence capable of binding the target sequence at the locus. In one embodiment, the DNA molecule has sequences that result in insertion of a heterologous sequence at the genome target locus, such as sequences for a screenable or selectable marker flanked by sequences ("arms") homologous to the targeted locus. The protein-binding RNA segment may comprise a meiRNA sequence from *S. pombe* or a homolog thereof, and the endonuclease comprises Spo11 from *S. cerevisiae* (e.g., SEQ ID NO: 1) or a homolog thereof, e.g., a protein with at least 80%, 85%, 87%, 90%, 92%, 94%, 95%, 96%, 97%, 98%, or 99% amino acid sequence identity to one of SEQ ID NOs. 2-4, or other endonucleases such as those from *S. cerevisiae*, phage or *Flavobacterium*, e.g., one of SEQ ID NOs. 24-27 or a protein with at least 80%, 85%, 87%, 90%, 92%, 94%, 95%, 96%, 97%, 98%, or 99% amino acid sequence identity to one of SEQ ID NOs. 24-27. The RNA component may contain the meiRNA-S subunit fused to the targeting RNA sequence, this composite RNA binds a polypeptide through meiRNA-S and binds a genomic DNA locus of interest (hybridization via complementarity) through the targeting RNA sequence. The polypeptide component may contain a Mei2 polypeptide fused to a Spo11 polypeptide, which allows for binding to the meiRNA-S segment of the RNA component. Binding of meiRNA-5 by the mei2-Spo11 fusion protein results in localization Spo11 to a specific target site in the genome that is recognized by the targeting RNA segment of the RNA component (hybridization via complementarity). The meiRNA-S function in *S. pombe* is to bind the Mei2 polypeptide, and the Spo11 function in yeast is to initiate homologous recombination at multiple sites in the genome during meiosis. In one embodiment, the Mei2 protein is from yeast (e.g., *S. pombe, Hansenula polymorpha, Pichia membranifaciens* or *Issatchenkia orientalis*), fungi (e.g., *Aspergillis terreus* or *Sporotrichum*), plants (e.g., *Arabidopsis* or *Oryza*), or green algae (e.g., *Volvox*).

The Mei2 protein or a homolog thereof may be from *Schizosaccharomyces pombe, Schizosaccharomyces japonicus, Trichoderma virens, Trichoderma atroviride, Trichoderma reesei, Gibberella zeae, Sporotrichum thermophile, Magnaporthe grisea, Hansenula polymorpha, Phytophthora ramorum, Arabidopsis thaliana, Oryza sativa, Glycine max, Aspergillus terreus, Pyrenophora tritici-repentis, Neurospora crassa* OR74A, *Volvox carteri, Fragilariopsis cylindrus, Chlamydomonas reinhardtii, Pichia membranifaciens, Arthroderma gypseum, Chlorella* sp., *Ostreococcus, Medicago truncatula, Aspergillus clavatus, Thalassiosira pseudonana, Plasmodium falciparum, Zea mays, Aspergillus niger, Thielavia terrestris, Aspergillus fumigatus, Phanerochaete chrysosporium, Chaetomium globosum*, or *Yarrowia lipolytica*. In one embodiment, the Spo11 protein or homolog thereof is from *Saccharomyces cerevisiae, Saccharomyces paradoxus, Saccharomyces bayanus, Zygosaccharomyces rouxii, Lachancea thermotolerans, Saccharomyces kluyveri* strain, *Candida glabrata, Yarrowia lipolytica, Micromonas pusilla* or *Aspergillus nidulans*.

The first isolated DNA molecule, the second isolated DNA molecule, the third isolated DNA molecule or the fourth isolated DNA molecule may be on one or more vectors, such as a plasmid. One or more of the first isolated DNA molecule, the second isolated DNA molecule, the third isolated DNA molecule or the fourth isolated DNA molecule may be integrated into the genome of a host cell. The first isolated DNA molecule or the first isolated RNA molecule may be fused to the second isolated DNA molecule or the second isolated RNA molecule, respectively. The first isolated DNA molecule or the first isolated RNA molecule may be 5' to the second isolated DNA molecule or the second RNA molecule, respectively. The first isolated DNA molecule or the first isolated RNA molecule may be 3' to the second isolated DNA molecule or the second isolated RNA molecule, respectively. In one embodiment, the RNA segment that binds the protein has at least 80%, 85%, 87%, 90%, 92%, 94%, 95%, 96%, 97%, 98%, 99% or 100% nucleic acid sequence identity to one of SEQ ID NOs. 8 to 10. The protein that binds the RNA segment may have at least 85%, 87%, 90%, 92%, 94%, 95%, 96%, 97%, 98%, 99% or 100% amino acid sequence identity to SEQ ID NO:5 or a portion thereof such as one having at least about 80%, 85%, 90%, 94%, 95%, 96%, 97%, 98%, 99% or 100% amino acid sequence identity to the RNA binding motifs in Mei2, e.g., motifs having SEQ ID NO:6 or SEQ ID NO:7. The endonuclease includes but is not limited to Spo11, i-TEV1, i-Sce1, HO, or Fok1, or an endonuclease having at least 80%, 85%, 87%, 90%, 92%, 94%, 95%, 96%, 97%, 98%, 99% or 100% amino acid sequence identity to SEQ ID NO:1. The third and fourth isolated DNA molecules or the third and fourth isolated RNA molecules may be fused to express a fusion protein having the endonuclease or the portion thereof and the RNA segment binding protein or the portion thereof. In one embodiment, the endonuclease is C-terminal to the RNA segment binding protein or the portion thereof. The RNA segment that binds the protein may be about 0.3 to about 1.6 Kb in length. The targeting RNA sequence may be about 15 to about 500 nucleotides in length, e.g., about 15 to about 200 nucleotides in length or about 20 to about 100 nucleotides in length. The first isolated RNA molecule and the second isolated RNA molecule may have complementary sequences at the 5'-end and 3'-end, respectively, allowing for hybridization of the complementary sequences, resulting in a physical link between the two RNA molecules. In one embodiment, those complementary sequences that link the targeting RNA sequence and the RNA segment are about 15 to about 500 nucleotides in length, e.g., about 20 to about 200 or about 20 to about 100 nucleotides in length. In one embodiment, the endonuclease may be fused to a first heterologous protein that binds to a second heterologous protein, and the protein having at least 80% amino acid sequence identity to SEQ ID NO:5 is fused to the second heterologous protein, thereby allowing for a complex of the endonuclease and RNA segment binding protein that is based on a protein-protein interaction between the first and the second proteins. For example, a first protein or a second protein may include one of the following domains: a fluorescent protein such as green fluorescent protein (GFP) or other fluorescent proteins such as YFP, c-jun, c-fos, GST, FRB, mTOR, FKBP, e.g., FKBP1A, SH2 domain, SH3 domain, cLIM domain, WW domain, phosphotyrosine-binding (PTB) domain, sterile alpha motif (SAM) domain, PDZ domain, FERM domain or calponin homology (CH) domain. For instance, the first protein or the second protein may be an Aequoreidae fluorescent protein, or a mammalian, fungal or plant protein, having at least 80%, 85%, 87%, 90%, 92%, 94%, 95%, 96%, 97%, 98%, or 99% amino acid sequence identity to one of SEQ ID NOs. 11-23.

A method for editing a target sequence at a locus in a host cell is also provided. In one embodiment, the method includes introducing to a host cell one or more of the following: a first isolated DNA molecule encoding a targeting RNA sequence or a first isolated RNA molecule comprising the targeting RNA sequence; a second isolated DNA molecule encoding a RNA segment that binds a protein, e.g., a protein having at least 80% amino acid sequence identity to SEQ ID NO:5 or a portion thereof with RNA binding activity or a second isolated RNA molecule comprising the RNA segment; a third isolated DNA molecule encoding an endonuclease or a portion thereof with nuclease activity, a third isolated RNA molecule encoding the endonuclease or the portion thereof or an isolated polypeptide comprising the endonuclease or the portion thereof with nuclease activity; and a fourth isolated DNA molecule encoding the RNA-binding protein, e.g., one having at least 80% amino acid sequence identity to SEQ ID NO:5, or a portion thereof that binds the RNA segment, a fourth RNA molecule encoding the RNA-binding protein or the portion thereof, or an isolated polypeptide comprising the RNA-binding protein or the portion thereof; and a double stranded DNA molecule comprising at least one nucleotide sequence that is capable of binding (hybridization via complementarity) the target sequence at the locus and optionally a heterologous sequence, such as a selectable or screenable gene or a sequence encoding a protein, e.g., such as a heterologous enzyme, that alters the amount of a biomolecule in the cell, that optionally is flanked by nucleotide sequences that are capable of binding to the target sequence at the locus. The host cell prior to editing may have one or more of the isolated DNA molecules (the first, second, third or fourth isolated DNA molecules) integrated into the genome. Modified cells (edited cells) having or expressing the nucleotide sequence in the double stranded DNA molecule and optionally having or expressing a heterologous sequence such as a selectable gene, screenable gene or other heterologous open reading frame, are then identified. The host cell may be a plant, yeast, algal or fungal cell. The cells may be modified with more than one (different) double stranded DNA molecules, e.g., sequentially, each double stranded DNA molecule optionally targeted to a different locus or target sequence, and each optionally having a distinct selectable gene. In one embodiment, e.g., in diploid cells, one double stranded DNA molecule may be employed to modify both alleles. In another embodiment, two different double stranded DNA molecules are used to modify alleles. For example, the modified cells have an altered phenotype, including but not limited to, altered ethanol production, altered starch production, altered glycerol production, altered chitin production, altered organic acid production, altered central metabolites, altered levels of cell wall components, or altered glucan production, relative to a corresponding unmodified cell. For example, a modified yeast cell may have an insertion of a gene encoding an enzyme that degrades starch. In another embodiment, a modified yeast cell may have a disruption in one or more native genes encoding an enzyme involved in ethanol fermentation or consumption, including for example pyruvate decarboxylase (PDC, catalyzes the conversion of pyruvate to acetaldehyde) and/or alcohol dehydrogenase 1 (ADH1, catalyzes the conversion of acetaldehyde to ethanol) or 2 (ADH2, catalyzes the conversion of ethanol to acetaldehyde). Such modifications decrease the ability of the yeast cell to produce ethanol, thereby maximizing production of other metabolites. In certain embodiments, the modified yeast cells comprise a disruption of one or more native genes encoding an enzyme involved in producing alternate fermentative products such as glycerol or other by-products such as acetate or diols, including for example glycerol 3-phosphate dehydrogenase (GPD, catalyzes the conversion of dihydroxyacetone phosphate to glycerol 3-phosphate).

BRIEF DESCRIPTION OF THE FIGURES

FIG. 4 shows the where each of the first, second, and third URA3 integration fragments correspond relative to the ADE2 gene.

DETAILED DESCRIPTION

Figures 1A, 1B, 1C, 1D, 1E, 1F, 1G, 1H:
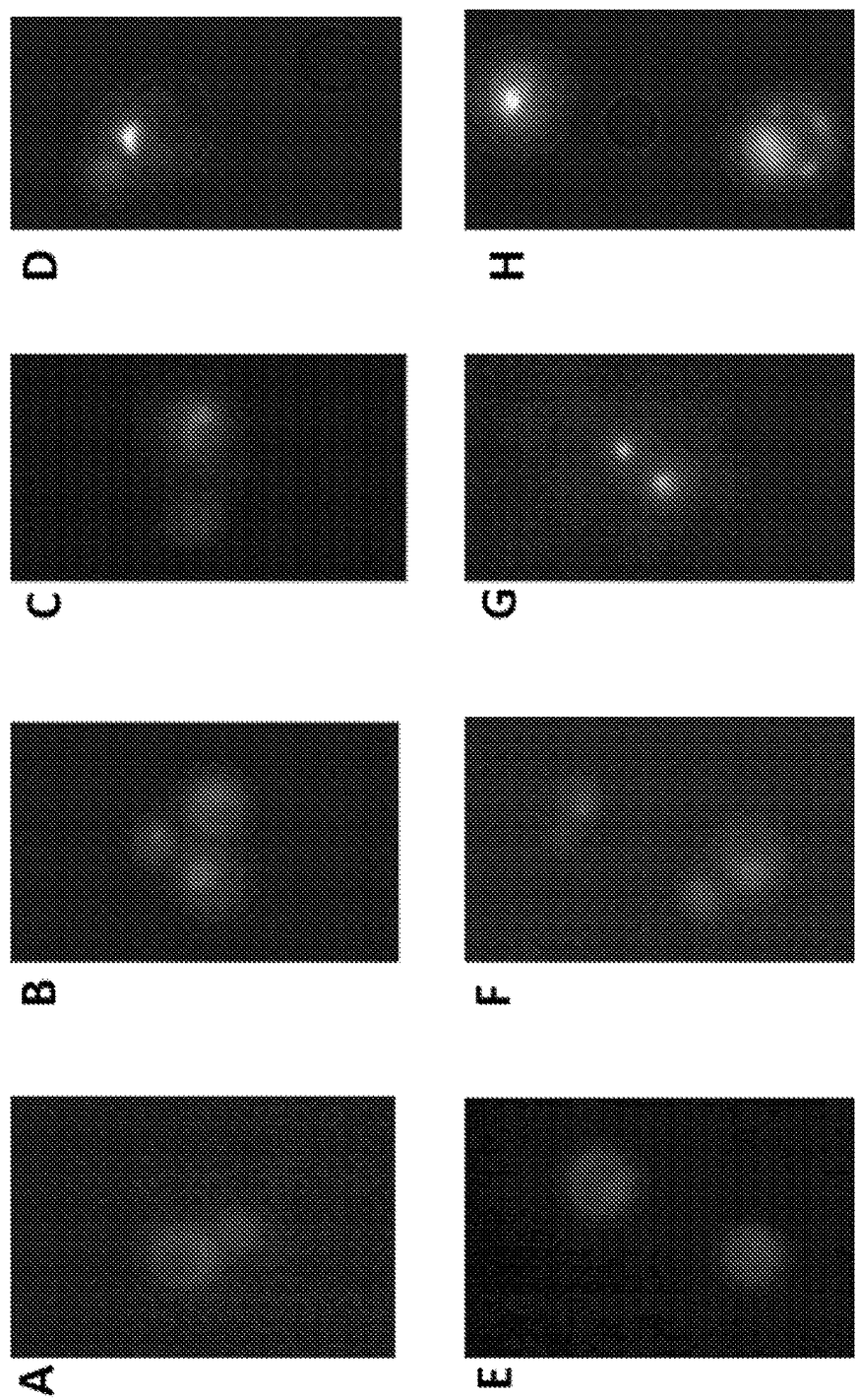
FIGS. 1A-1H. Localization of GFP fused to Spo11-Mei2 or Mei2-Spo11 in the absence of one of the RNA components (the absence of a targeting RNA sequence) (panels A and E), or in the presence of meiRNA fused to targeting RNA sequences of varying lengths (panels B-D and F-H). Orientation A, Spo11-Mei2-GFP: A) GFP fluorescence with an incomplete RNA component construct (pPS015) (when both the targeting RNA sequence and the RNA segment that binds the protein are present in a cell, they correspond to the "RNA component," which is also referred to as guide RNA or gRNA), i.e., the constructs in A) only contain the RNA segment); B) GFP fluorescence with meiRNA fused to a 20 bp targeting sequence construct (pPS017); C) GFP fluorescence with meiRNA fused to a 45 bp targeting sequence construct (pPS019); D) GFP fluorescence with meiRNA fused to a 70 bp targeting sequence construct (pPS021), Orientation B, Mei2-Spo11-GFP: E) GFP fluorescence with meiRNA alone (pPS016); F) GFP fluorescence with meiRNA fused to a 20 bp targeting sequence construct (pPS018); G) GFP fluorescence with meiRNA fused to a 45 bp targeting sequence construct (pPS020); H) GFP fluorescence with meiRNA fused to a 70 bp targeting sequence construct (pPS022).

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature or occurs at a frequency that is less common than wild type.

The terms "non-naturally occurring," "isolated" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

The term "heterologous" in the context of a contiguous nucleic acid sequence or a protein sequence refers to a portion of the nucleic acid or protein that is from a different source, or is in a different context (linear) than is found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into an mRNA or another type of RNA) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

A "promoter" is a nucleotide sequence that controls the expression of a coding and/or non-coding sequence by providing the recognition for RNA polymerase and other factors required for proper transcription.

An "enhancer" is a DNA sequence that can stimulate promoter activity and may be an innate element of the promoter or a heterologous element inserted to enhance the level or tissue specificity of a particular promoter. An enhancer may be capable of operating in both orientations (5' to 3' and 3' to 5' relative to the gene of interest coding sequences), and is capable of functioning even when moved either upstream or downstream from the promoter. Both enhancers and other upstream promoter elements bind sequence-specific DNA-binding proteins that mediate their effects.

The terms "polypeptide", "peptide" and "protein" are used interchangeably herein to refer to polymers of amino acids of any length. The polymer may be linear or branched, it may comprise modified amino acids, and it may be interrupted by non native (heterologous) amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The term "effective amount" refers to the amount of an agent that is sufficient to achieve desired results. The effective amount may vary.

A "vector" is employed to maintain genetic material in or transfer genetic material to a cell. Vectors includes plasmids, cosmids, YACs (yeast artificial chromosomes), BACs (bacterial artificial chromosomes) and segments of DNA or RNA. Vectors for use in transforming cells may comprise DNA encoding a gene product (e.g., protein or RNA) or a portion thereof, e.g., sequences for homologous recombination, as well as other DNA that one desires to introduce into the cells. These DNA constructs can further include elements such as promoters, enhancers, polylinkers, marker or selectable genes, or even regulatory genes, as desired. For instance, one of the DNA segments or genes chosen for cellular introduction will often encode a protein that will be expressed in the resultant transformed (recombinant) cells, such as to result in a screenable or selectable trait.

Methods and Systems

The practice of the present method employs, unless otherwise indicated, conventional techniques of biochemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Several aspects of the disclosure relate to vector systems, e.g., a system having one or more vectors. Vectors can be designed for expression of RNA transcripts (e.g., for RNA products or proteins such as enzymes) in prokaryotic or eukaryotic cells ("expression vectors"). For example, transcripts can be expressed in bacterial cells such as *Escherichia coli*, insect cells (using baculovirus expression vectors), yeast cells, plant cells, algal cells, fungal cells, or other cells. Suitable host cells are discussed further in Goeddel, GENE EXPRESSION TECHNOLOGY: METHODS IN ENZYMOLOGY 185, Academic Press, San Diego, Calif. (1990), which is incorporated by reference herein. Alternatively, the recombinant expression vector can be transcribed and translated in vitro, for example using T3, T7, RNA PolI, RNA PolII, or RNA PolIII promoter regulatory sequences and T3, T7, RNA PolI, RNA PolII, or RNA PolIII polymerase.

Vectors may be introduced and propagated in a prokaryote or eukaryote. In some embodiments, a prokaryote is used to amplify copies of a vector to be introduced into a eukaryotic cell or a vector that is an intermediate in the production of a subsequent vector to be introduced into a eukaryotic cell. In some embodiments, a prokaryote is used to amplify copies of a vector and express one or more nucleic acids, such as to provide a source of one or more proteins for delivery to a host cell or host organism. Expression of proteins in prokaryotes may be carried out in *Escherichia coli* with vectors containing constitutive or inducible promoters directing the expression of either fusion or non-fusion proteins. Fusion vectors may add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. A proteolytic cleavage site (for a specific enzyme) may be introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to a different protein.

In some embodiments, a vector is a yeast expression vector. Examples of vectors for expression in yeast such as *Saccharomyces cerevisiae* include but are not limited to pYepSec1 (Baldari, et al., 1987. EMBO J. 6: 229-234), pMFa (Kuijan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.). Yeast cells useful in the present methods include but are not limited those from phylum Ascomycota, subphylum Saccharomycotina, class Saccharomycetes or Schizosaccharomycetes, order Saccharomycetales or Schizosaccharomycetales, family Saccharomycetaceae, genus *Saccharomyces, Schizosaccharomyces*, or *Pichia (Hansenula)*, e.g., species: *P. anomola, P. guilliermondiii, P. norvegenesis, P. ohmeri*, or *P. kluyven, B. exigua, P. occidentalis, P. sattulata, P. terricola, P. kudriazevii, P. pastoris*, or *Yarrowia*. Yeast cells employed in the method may be native (non-recombinant) cells or recombinant cells, e.g., those which have already been transformed with exogenous DNA. An enzyme(s) that is encoded by the exogenous DNA may be from the same species or heterologous (from a different species).

Host cells useful in the present methods include yeast (e.g., *S. pombe, Hansenula polymorpha, Pichia membranifaciens* or *Issatchenkia orientalis*), fungi (e.g., *Aspergillis terreus* or *Sporotrichum*), plants (e.g., *Arabidopsis* or *Oryza*), or green algae (e.g., Volvox), *Schizosaccharomyces pombe, Schizosaccharomyces japonicus, Trichoderma virens, Trichoderma atroviride, Trichoderma reesei, Gibberella zeae, Sporotrichum thermophile, Magnaporthe grisea, Hansenula polymorpha, Phytophthora ramorum, Arabidopsis thaliana, Oryza sativa, Glycine max, Aspergillus terreus, Pyrenophora tritici-repentis, Neurospora crassa* OR74A, *Volvox carteri, Fragilariopsis cylindrus, Chlamydomonas reinhardtii, Pichia membranifaciens, Arthroderma gypseum, Chlorella* sp., *Ostreococcus, Medicago truncatula, Aspergillus clavatus, Thalassiosira pseudonana, Plasmodium falciparum, Sclerotium rolfsii, Zea mays, Aspergillus niger, Thielavia terrestris, Aspergillus fumigatus, Phanerochaete chrysosporium, Chaetomium globosum, Yarrowia lipolytica, Saccharomyces cerevisiae, Saccharomyces paradoxus, Saccharomyces bayanus, Zygosaccharomyces rouxii, Lachancea thermotolerans, Saccharomyces kluyveri* strain, *Candida glabrata, Yarrowia lipolytica, Micromonas pusilla* and *Aspergillus nidulans*.

In one embodiment, a cell is transformed with DNA described herein, e.g., in a vector. The vector may include elements such as promoters, enhancers, polylinkers, marker or selectable genes, or even regulatory genes, as desired. For instance, one of the DNA segments or genes chosen for cellular introduction will often encode a protein that will be expressed in the resultant transformed (recombinant) cells, such as to result in a screenable or selectable trait.

DNA useful for introduction into cells includes that which has been derived or isolated from any source, that may be subsequently characterized as to structure, size and/or function, chemically altered, and later introduced into cells. An example of DNA "derived" from a source would be a DNA sequence that is identified as a useful fragment within a given organism, and that is then chemically synthesized in essentially pure form. An example of such DNA "isolated" from a source would be a useful DNA sequence that is excised or removed from said source by biochemical means, e.g., enzymatically, such as by the use of restriction endonucleases, so that it can be further manipulated, e.g., amplified, for use in the invention, by the methodology of genetic engineering. Such DNA is commonly also referred to as "recombinant DNA."

Therefore, useful DNA includes completely synthetic DNA, semi-synthetic DNA, DNA isolated from biological sources, and DNA derived from introduced RNA. The introduced DNA may be or may not be a DNA originally resident in the host cell genotype that is the recipient of the DNA (native or heterologous, respectively, to the host cell). It is within the scope of this disclosure to isolate a gene from a given genotype, and to subsequently introduce multiple copies of the gene into the same genotype, e.g., to enhance production of a given gene product.

The introduced DNA includes, but is not limited to, DNA from genes such as those from bacteria, yeasts, fungi, plants or vertebrates. The introduced DNA can include modified or synthetic genes, e.g., "evolved" genes, portions of genes, or chimeric genes, including genes from the same or different genotype. The term "chimeric gene" or "chimeric DNA" is defined as a gene or DNA sequence or segment comprising at least two DNA sequences or segments from species that do not combine DNA under natural conditions, or which DNA sequences or segments are positioned or linked in a manner that does not normally occur in the native genome of the untransformed cell.

The introduced DNA used for transformation herein may be circular or linear, double-stranded or single-stranded. Generally, the DNA is in the form of chimeric DNA, such as plasmid DNA, which can also contain coding regions flanked by regulatory sequences that promote the expression of the recombinant DNA present in the transformed cell. For example, the DNA may include a promoter that is active in a cell that is derived from a source other than that cell, or may utilize a promoter already present in the cell that is the transformation target.

Generally, the introduced DNA is relatively small, e.g., less than about 30 kb to minimize any susceptibility to physical, chemical, or enzymatic degradation that is known to increase as the size of the DNA increases. The number of proteins, RNA transcripts or mixtures thereof that is introduced into the cell may be preselected and defined, e.g., from one to about 5 to 10 such products of the introduced DNA may be formed.

The selection of an appropriate expression vector depends upon the host cells. An expression vector in a bacterial host can contain, for example, (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a gene of interest that is operatively linked to the DNA elements to control transcription initiation. The expression vector used may be one capable of autonomously replicating in the host cell or one capable of integrating into the chromosome, and which optionally contains a promoter enabling transcription of the linked gene.

Yeast or fungal expression vectors may comprise an origin of replication, a suitable promoter and enhancer, and also any necessary ribosome binding sites, polyadenylation site, splice donor and acceptor sites, transcription termination sequences, and 5' and 3' flanking nontranscribed sequences. Several well-characterized yeast expression systems are known in the art. A large variety of shuttle vectors with yeast promoters are also known to the art. However, any other plasmid or vector may be used as long as they are replicable and viable in the host.

The construction of vectors that may be employed is known to those of skill of the art (e.g., Sambrook and Russell, Molecular Biology: *A Laboratory Manual,* 2001). An expression vector may contain one or a plurality of restriction sites allowing for placement of a polynucleotide, e.g., encoding an enzyme. The expression vector may also contain a termination signal operably linked to the polynucleotide as well as regulatory sequences required for proper translation of the polynucleotide. The expression vector containing the polynucleotide may be chimeric, meaning that at least one of its components is heterologous with respect to at least one of the other components. Expression of the polynucleotide in the expression vector may be under the control of a constitutive promoter, inducible promoter, regulated promoter, viral promoter or synthetic promoter.

The expression vector may include, in the 5'-3' direction of transcription, a transcriptional and translational initiation region, a polynucleotide and a transcriptional and translational termination region functional in vivo and/or in vitro. The termination region may be native with the transcriptional initiation region, may be native with the polynucleotide, or may be derived from another source. The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences that may be a combination of synthetic and natural sequences. The vector may also include appropriate sequences for amplifying expression.

In some embodiments, a promoter for use in the vectors includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. A promoter may also include a regulatory element or elements capable of controlling the expression of a coding sequence or functional RNA. This type of promoter sequence contains proximal and more distal elements, the latter elements are often referred to as enhancers.

Representative examples of promoters include, but are not limited to, promoters known to control expression of genes in prokaryotic or eukaryotic cells or their viruses. For instance, any promoter capable of expressing in yeast hosts can be used as a promoter in the present invention, for example, the GAL4 promoter may be used. Additional promoters useful for expression in a yeast cell are well described in the art. Examples thereof include promoters of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes and the like in the glycolytic pathway, heat shock protein promoter, MFa-1 promoter, CUP 1 promoter, MET, the promoter of the TRP1 gene, the AOX (alcohol oxidase) gene promoter, e.g., the AOX1 or AOX2 promoter, the ADC1 gene (coding for the alcohol dehydrogenase I) or ADR2 gene (coding for the alcohol dehydrogenase II), acid phosphatase (PHO5) gene, isocytochrome c gene, a promoter of the yeast mating pheromone genes coding for the a- or α-factor, or the GAL/CYC1 hybrid promoter (intergenic region of the GAL1-GAL10 gene/Cytochrome1 gene). Promoters with transcriptional control that can be turned on or off by variation of the growth conditions include, e.g., PHO5, ADR2, and GAL/CYC1 promoters. The PHO5 promoter, for example, can be repressed or derepressed at will, solely by increasing or decreasing the concentration of inorganic phosphate in the medium. Some promoters, such as the ADH1 promoter, allow high-level constitutive expression of the gene of interest.

Any promoter capable of expressing in fungi may be used. Examples are a promoter induced strongly by starch or cellulose, e.g., a promoter for glucoamylase or a-amylase from the genus *Aspergillus* or cellulase (cellobiohydrase) from the genus *Trichoderma*, a promoter for enzymes in the glycolytic pathway, such as phosphoglycerate kinase (pgk) and glycerylaldehyde 3-phosphate dehydrogenase (gpd), etc.

Overexpression can be achieved by insertion of a strong promoter in a position that is operably linked to the target gene, or by insertion of one or more than one extra copy of the selected gene. For example, extra copies of the gene of interest may be positioned on an autonomously replicating plasmid, such as pYES2.0 (Invitrogen Corp., Carlsbad, Calif.), where overexpression is controlled by the GAL4 promoter after addition of galactose to the medium.

Several inducible promoters are known in the art. Many are described in a review by Gatz, Curr. Op. Biotech., 7.168 (1996) (see also Gatz, Ann. Rev. Plant. Physiol. Plant Mol. Biol. 4889 (1997)). Examples include tetracycline repressor system, Lac repressor system, copper-inducible systems, salicylate-inducible systems (such as the PR1a system), glucocorticoid-inducible (Aoyama T. et al., 1997), alcohol-inducible systems, e.g., AOX promoters, and ecdysome-inducible systems. Also included are the benzene sulphonamide-inducible (U.S. Pat. No. 5,364,780) and alcohol-inducible (WO 97/06269 and WO 97/06268) systems and glutathione S-transferase promoters.

In addition to the use of a particular promoter, other types of elements can influence expression of linked sequences. In particular, introns have demonstrated the potential for enhancing expression.

Vectors may be constructed to include an enhancer element. Constructs may also include the gene of interest along with a 3' end DNA sequence that acts as a signal to terminate transcription and allow for the polyadenylation of the resultant RNA.

As the DNA sequence between the transcription initiation site and the start of the coding sequence, i.e., the untranslated leader sequence, can influence gene expression, one may also wish to employ a particular leader sequence. Leader sequences are contemplated to include those that include sequences predicted to direct optimum expression of the attached gene, e.g., to include a consensus leader sequence that may increase or maintain mRNA stability and prevent inappropriate initiation of translation. The choice of such sequences will be known to those of skill in the art in light of the present disclosure.

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait that one can "select" for by chemical means, i.e., through the use of a selective agent (e.g., an antibiotic, or the like), or whether it is simply a trait that one can identify through observation or testing, i.e., by screening. Of course, many examples of suitable marker genes are known to the art and can be employed in the practice of the invention.

Included within the terms selectable or screenable marker genes are also genes that encode a "secretable marker" whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA and small active enzymes detectable in extracellular solution.

Screenable markers that may be employed include, but are not limited to, a 0-glucuronidase or uidA gene (GUS) that encode an enzyme for which various chromogenic substrates are known; a beta-lactamase gene, which encodes an enzyme for which various chromogenic substrates are known (e.g., PADAC, a chromogenic cephalosporin); a xylE gene, which encodes a catechol dioxygenase that can convert chromogenic catechols; an alpha-amylase gene; a tyrosinase gene that encodes an enzyme capable of oxidizing tyrosine to DOPA and dopaquinone that in turn condenses to form the easily detectable compound melanin; a beta-galactosidase gene, which encodes an enzyme for which there are chromogenic substrates; a luciferase (lux) gene, which allows for bioluminescence detection; or even an aequorin gene, which may be employed in calcium-sensitive bioluminescence detection, or a green fluorescent protein gene. Selectable nutritional markers may also be used, such as HIS3, URA3, TRP-1, LYS-2 and ADE2.

In general, the present editing system refers collectively to transcripts and other elements involved in the expression of or directing the activity of a RNA-binding protein, a RNA segment to which the protein binds, an endonuclease, a targeting RNA sequence, and a double stranded DNA molecule having DNA with at least one nucleotide sequence that is capable of binding to a target sequence at a locus. In general, the system is characterized by elements that promote the formation of a complex at the genome site of the target sequence. In the context of formation of a complex, a "target sequence" refers to a sequence in a locus to which a targeting RNA sequence is designed to have complementarity (additionally, sequences in the DNA component have complementarity to sequences at the locus that flank or overlap those with complementarity to the targeting RNA sequence), where hybridization between a target sequence, e.g., in the genome, and a targeting RNA sequence, or the DNA component, promotes the formation of a complex. By definition, a nucleotide sequence in a DNA molecule that is capable of binding to a target sequence in a locus and sequences in the targeting RNA sequence have at least 80%, 82%, 84% 85%, 87%, 90%, 91%, 92%, 95%, 97%, 98%, 99% or more, nucleotide sequence identity to target sequences at the locus. Thus, full complementarity is not necessarily required, provided there is sufficient complementarity to cause hybridization and promote formation of a complex. A target sequence may comprise any polynucleotide, such as DNA or RNA polynucleotides but is generally genomic. In some embodiments, a target sequence is located in the nucleus or cytoplasm of a cell. In some embodiments, the target sequence may be within an organelle of a eukaryotic cell, for example, nucleus, mitochondrion or chloroplast.

Typically, in the context of the system, formation of a complex comprising a targeting RNA sequence hybridized to a genomic target sequence (locus) and bound to an endonuclease and a RNA-binding protein, as a result of the RNA segment being linked to the targeting RNA sequence that binds to the RNA-binding protein, provides for cleavage of one or both strands in or near (e.g., within 1, 2, 3, 4, 5, 6, 7, 8, 9, 10, 20, 50, or more base pairs from) the genomic target sequence. In some embodiments, one or more vectors driving expression of one or more elements of the system are introduced into a host cell such that expression of the elements of the system direct formation of a complex at one or more target sites. For example, an endonuclease, a RNA-binding protein, a targeting RNA sequence optionally covalently linked to a RNA segment that binds the RNA-binding protein, could each be operably linked to separate regulatory elements on separate vectors. Alternatively, two or more of the elements expressed from the same or different regulatory elements, may be combined in a single vector, with one or more additional vectors providing any components of the system not included in the first vector. System elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a fusion of an endonuclease and a RNA-binding protein and another promoter (optionally which is the same type of promoter) may drive expression of the RNA segment and the targeting RNA sequence (which are optionally covalently linked). In some embodiments, a fusion of nucleic acid encoding an endonuclease and a RNA-binding protein, and a fusion of the RNA segment and targeting RNA sequence, are operably linked to and expressed from different promoters.

In some embodiments, a vector comprises a regulatory element operably linked to a coding sequence such as one encoding an endonuclease, e.g., as a Spo11 protein, or a RNA-binding protein, e.g., Mei2. Non-limiting examples of Spo11 or related proteins include SEQ ID NOs:1-4, and proteins having at least 80%, 85%, 87%, 90%, 92%, 95%, 97%, 98%, 99% or 100% amino acid sequence identity thereto. Non-limiting examples of a RNA-binding protein include Mei2, e.g., having SEQ ID NO:5 and proteins having at least 80%, 85%, 87%, 90%, 92%, 95%, 97%, 98%, 99% or 100% amino acid sequence identity thereto. In some embodiments, the endonuclease directs cleavage of one or both strands at the location of a genomic target sequence, such as within the target sequence and/or within the complement of the target sequence. In some embodiments, the endonuclease directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes an endonuclease that is mutated with respect to a corresponding wild-type endonuclease such that the endonuclease lacks the ability to cleave one or both strands of a target polynucleotide containing a target sequence. In some aspects, nickases may be used for genome editing via homologous recombination. In some embodiments, a nickase may be used in combination with targeting RNA sequences which target respectively sense and antisense strands of the DNA target. This combination allows both strands to be nicked and used to induce NHEJ.

In some embodiments, a coding sequence encoding an endonuclease or a RNA-binding protein is codon optimized for expression in particular cells, such as eukaryotic cells. The eukaryotic cells may be those of or derived from a particular organism, such as a plant, yeast, fungal or insect cells. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding an endonuclease enzyme or a RNA-binding protein correspond to the most frequently used codon for a particular amino acid.

In general, a targeting RNA sequence, or homology sequences ("arms" that include a nucleotide sequence that is capable of binding to the target sequence) in the DNA component (donor DNA), may be any sequence having sufficient complementarity with a target genomic polynucleotide sequence to hybridize with (bind to) the target sequence at the locus to be edited and, for the targeting RNA sequence to direct sequence-specific binding of a complex to the target sequence. Generally, the targeting RNA sequences are internal or can overlap to the arms of the DNA component relative to the target sequence at the locus. Exemplary genomic target sequences include those that are unique in a target sequence to be edited. In some embodiments, the degree of complementarity between a targeting RNA sequence or homology arm(s) in the DNA component and its corresponding target sequence to be edited, when optimally aligned using a suitable alignment algorithm, is about or more than about 80%, 85%, 90%, 95%, 97.5%, 99%, or 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). Inspection of nucleic acid or amino acid sequences for two nucleic acids or two polypeptides reveal sequence identity and similarities between the compared sequences. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters. Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLOSUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, −2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

In some embodiments, a targeting RNA sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a targeting RNA sequence is less than about 75, 50, 45, 40, 35, 30, 25, 20, 15, 12, or fewer nucleotides in length. The ability of a targeting RNA sequence to direct sequence-specific binding of a complex to a target sequence may be assessed by any suitable assay. For example, the components of a system sufficient to form a complex, including the targeting RNA sequence to be tested, may be provided to a host cell having the corresponding target sequence, such as by transformation or transfection with vectors encoding the components of the sequence, followed by an assessment of preferential cleavage within the target sequence, such as by Surveyor assay as described herein. Similarly, cleavage of a target sequence may be evaluated in a test tube by providing the target sequence, components of a complex, including the targeting RNA sequence to be tested and a control sequence different from the test targeting RNA sequence, and comparing binding or rate of cleavage at the target sequence between the test and control sequence reactions. Other assays are possible, and will occur to those skilled in the art.

In some embodiments, the endonuclease may be part of a fusion protein comprising one or more heterologous peptide or protein domains (e.g., about or more than about 1, 2, 3, 4, 5, 6, 7, 8, 9, 10, or more domains in addition to the endonuclease), such as a RNA binding domain, e.g., a binding domain other than Mei2, or other proteins such as a heterologous protein that binds to another protein. A fusion protein may comprise a linker sequence between any two domains, e.g., a linker of one or more amino acids, e.g., 2 to about 25, or up to 20, e.g., 5 to 15, amino acid residues. Examples of protein domains that may be fused to an endonuclease or RNA-binding protein include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). The reporter gene may be introduced into a cell to encode a gene product which serves as a marker by which to measure the alteration or modification of expression of the gene product. In one embodiment, the DNA molecule encoding the gene product may be introduced into the cell via a vector.

In some aspects, the disclosure provides methods comprising delivering one or more polynucleotides, such as or one or more vectors as described herein, one or more transcripts thereof, and/or one or proteins transcribed therefrom, to a host cell. In some aspects, the disclosure further provides cells produced by such methods, and organisms (such as animals, plants, or fungi) comprising or produced from such cells. In some embodiments, an endonuclease and a RNA-binding protein in combination with (and optionally complexed with) a targeting RNA sequence linked to a RNA having the binding domain for the RNA-binding protein, are delivered to a cell. Conventional gene transfer methods can be used to introduce nucleic acids in cells including yeast, plant, fungal or mammalian cells. Such methods can be used to administer nucleic acids encoding components of a system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. Conventional viral based systems could include retroviral, lentivirus, adenoviral, adeno-associated and herpes simplex virus vectors.

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995): Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

In some embodiments, one or more vectors described herein are used to produce a transgenic plant including transgenic algae. In certain embodiments, the organism or subject is a plant. In certain embodiments, the organism or subject or plant is algae. Methods for producing transgenic plants are known in the art, and generally begin with a method of cell transfection, such as described herein.

In one aspect, the disclosure provides for methods of modifying a target polynucleotide in a eukaryotic cell, which may be in vivo, ex vivo or in vitro. In some embodiments, the method comprises sampling a cell or population of cells from a lower eukaryote, e.g., yeast, fungi or plant (including micro-algae), and modifying the cell or cells. Culturing may occur at any stage ex vivo. The cell or cells may even be re-introduced into the lower eukaryote or plant (including micro-algae).

In one aspect, the disclosure provides for methods of modifying a target sequence in a eukaryotic cell. In some embodiments, the method comprises allowing a genome editing complex to bind to the target sequence to effect cleavage of said target sequence thereby modifying the target sequence wherein the genome editing complex comprises an endonuclease complexed with a targeting RNA sequence hybridized to a target sequence within a locus, wherein said targeting RNA sequence is linked to a RNA segment which in turn is bound to a RNA-binding protein that is associated with the endonuclease.

In one aspect, the disclosure provides a method of modifying expression of a target sequence in a locus in a eukaryotic cell. In some embodiments, the method comprises allowing a genome editing complex to bind to target sequence such that said binding results in increased or decreased expression of said target sequence; wherein the genome editing complex comprises an endonuclease complexed with a targeting RNA sequence hybridized to a target sequence within the locus, wherein said targeting RNA sequence is linked to a RNA segment that binds a protein that is associated with the endonuclease.

The ability to use the systems to perform efficient and cost effective gene editing and manipulation allows the rapid selection and comparison of single and multiplexed genetic manipulations to transform such genomes for improved production and enhanced traits. In this regard reference is made to U.S. patents and publications: U.S. Pat. Nos. 6,603,061, 7,868,149 and US 2009/0100536, all the contents and disclosure of each of which are herein incorporated by reference in their entirety. In the practice of the invention, the contents and disclosure of Morrell et al "Crop genomics: advances and applications" Nat Rev Genet. 2011 Dec. 29; 13(2):85-96 are also herein incorporated by reference in their entirety.

In one aspect, the disclosure provides methods for using one or more elements of a genome editing system. The complex described herein provides an effective means for modifying a target sequence at a locus. The genome editing complex has a wide variety of utility including modifying (e.g., deleting, inserting, translocating, inactivating, activating) a target sequence in a multiplicity of cell types. As such the complex has a broad spectrum of applications in, e.g., gene therapy, or drug screening.

EXEMPLARY EMBODIMENTS

The disclosed editing system has three components: a RNA component; a polypeptide component; and a DNA component. DNA may be employed to prepare the RNA component, and RNA or DNA may be employed to prepare the polypeptide component.

In one embodiment, the RNA component includes a targeting RNA sequence of about 15 to about 500, e.g., about 15 to about 200 or about 20 to 100, nucleotides in length, complementary to a region of DNA of interest in the target sequence in the locus to be edited. The targeting RNA sequence is variable based on the target sequence to be edited. The RNA component also includes a protein binding RNA, the RNA segment. In one embodiment, the RNA is meiRNA. meiRNA is encoded by the sme2 gene from S. pombe. The meiRNA has 2 iso-forms, meiRNA-S (0.5 kb) and meiRNA-L (1.0 kb). As meiRNA-S is a subset of the meiRNA-L sequence, the entire meiRNA-L sequence may be used. Alternatively, the genome editing system may use meiRNA-S.

In one embodiment, the two parts of the RNA component may be covalently linked by fusing the sequences together at the DNA level, which DNA when expressed provides for a single RNA molecule where the two parts of the RNA component are linked together. In one embodiment, a spacer having one or more nucleotides, e.g., 2 to about 20 nucleotides, such as 10 to 20 nucleotides, may be between the RNA segment and the targeting RNA sequence (regardless of the order of the two). In one embodiment, the first bases, e.g., from 20-100 nucleotides at the 5' end have the targeting RNA sequence and the rest of the RNA is RNA that binds the protein (RNA segment). The two subparts may (or may not) be separated by a heterologous sequence. The targeting RNA sequence in the RNA component allows for binding of the RNA component to a target sequence at a locus to be edited (through complementarity) and the RNA segment binds the polypeptide component.

In one embodiment, the RNA component may be in two separate parts. The first part has the targeting RNA and the second part has the RNA segment that binds the protein. In one embodiment, the 3' end of the RNA component has about 40 to 100 bases of homology to the 5' region of the meiRNA-S sequence. Therefore, the two parts of the RNA component are not covalently linked together, but are associated with each other through homology (base-paired RNA component, i.e., hydrogen bonds). The base-paired RNA component forms a bi-functional RNA component that can associate with the target DNA sequence of interest and also binds to the RNA-binding protein.

The polypeptide component includes a RNA-binding protein, e.g., Mei2 from S. pombe, that binds to the RNA segment in the RNA component, e.g., meiRNA-S sequence, and an endonuclease such as Spo11 (product of the S. cerevisiae SPO11 gene), that cuts DNA by making a double strand break. In one embodiment, the polypeptide component is a fusion (in-frame) of, for example, the Mei2 and Spo11 polypeptides coupled together by a flexible amino acid linker. A flexible amino acid linker may separate the two parts of the polypeptide by four or more amino acids, such as a glycine amino acid, or by 10, 15 or up to 25 residues. The polypeptides may be fused in one of two ways: the endonuclease, e.g., Spo11, is at the amino-terminus of the protein and the RNA-binding protein, e.g., Mei2, is at the carboxy-terminus; or the RNA-binding protein, e.g., Mei2 is at the amino-terminus of the protein and the endonuclease, e.g., Spo11 is at the carboxy-terminus. In one embodiment, each of the polypeptide segments (e.g., Spo11 and Mei2) can be constructed such that they contain an interactive polypeptide domain that binds to a complementary domain engineered as a fusion on the other polypeptide segment. The two complementary domains interact via non-covalent bonds (such as electrostatic, π-effects, van der Waals forces, and hydrophobic effects), and through this interaction the Spo11 and Mei2 proteins are brought together. Examples of interactive polypeptide domains include Glutathione-S-transferase (GST), GFP, c-fos and c-jun, proteins that bind SH2 and SH3 domains, and the interacting domains of FRB and FKBP12.

Examples of the types of DNA to be inserted into the genome may include: a selectable marker, e.g., antibiotic resistance, auxotrophic markers such as URA3 and HIS3, a sequence of DNA that contains a stop codon, a sequence of DNA that contains promoter-gene-terminator sequence, a sequence of DNA that contains a mismatch base or deleted nucleotide(s) relative to the genomic target sequence to introduce a substitution mutation or deletion, respectively, or any DNA sequence desirable for insertion into the genome. The DNA component includes the nucleotide sequence that is capable of binding to the target sequence and that is to be inserted into the genome at the target locus determined by the targeting RNA sequence.

The targeting RNA sequence may overlap (have homology) with one or more of the arms in the DNA component. In one embodiment, the targeting RNA sequence corresponds to target sequences, e.g., in the genome, that are between two arms, which in the presence of Spo11, results in a cleavage site somewhere in between where there is homology in the DNA component.

In one embodiment, the components are introduced to cells sequentially or at the same time, e.g., using plasmids that do not integrate into the host genome. The RNA and polypeptide components can be encoded on the same plasmid or on different plasmids. Alternatively, the genes encoding the polypeptide component can be integrated into the genome at a specific site, and the RNA component and DNA components delivered separately. This may be advantageous for a cell line that is used repeatedly over time by reducing the size of the plasmids used for the other components.

The RNA component may be synthesized in vitro and transformed directly into cells that contain the other components of the system, e.g., delivered in other ways, or the RNA component, the DNA component and polypeptide component may be simultaneously or consecutively introduced into the cell under the appropriate conditions.

The DNA component can be synthesized in vitro, amplified by PCR, or isolated via restriction digest from a larger DNA.

For example, a system for editing of a target sequence in a host cell (locus) is provided. In one embodiment, the system includes a first isolated DNA molecule having a DNA segment encoding a targeting RNA sequence or a first isolated RNA molecule comprising the targeting RNA sequence; a second isolated DNA molecule having a DNA segment encoding a RNA segment that binds a protein having at least 80% amino acid sequence identity to SEQ ID NO:5 or a second isolated RNA molecule comprising the RNA segment; a third isolated DNA molecule having a DNA segment encoding an endonuclease or a portion thereof with nuclease activity, a third isolated RNA molecule encoding the endonuclease or the portion thereof or an isolated polypeptide comprising the endonuclease or the portion thereof; a fourth isolated DNA molecule encoding the protein having at least 80% amino acid sequence identity to SEQ ID NO:5 or a portion thereof that binds the RNA segment, a fourth isolated RNA molecule encoding the protein having at least 80% amino acid sequence identity to SEQ ID NO:5 or the portion thereof that binds the RNA segment or an isolated polypeptide comprising the protein having at least 80% amino acid sequence identity to SEQ ID NO:5 or the portion thereof that binds the RNA segment; and an isolated double stranded DNA molecule having DNA comprising at least one nucleotide sequence that is capable of binding to the target sequence at a locus.

In some embodiments, the first isolated DNA molecule and the second isolated DNA molecule, or the third isolated DNA molecule and the fourth isolated DNA molecule, are on a vector. In one embodiment, the vector is a plasmid. In one embodiment, the first isolated DNA molecule, the second isolated DNA molecule, the third isolated DNA molecule or the fourth isolated DNA molecule, or any combination thereof, is/are integrated into the genome of a host cell. In one embodiment, expression of the first isolated DNA molecule, the second isolated DNA molecule, the third isolated DNA molecule or the fourth isolated DNA molecule is inducible. In one embodiment, the first isolated DNA molecule is fused to the second isolated DNA molecule or the first isolated RNA molecule is fused to the second isolated RNA molecule. In one embodiment, the first isolated DNA molecule is 5' to the second isolated DNA molecule or the first isolated RNA molecule is 5' to the second isolated RNA molecule. In one embodiment, the first isolated DNA molecule is 3' to the second isolated DNA molecule or the first isolated RNA molecule is 3' to the second isolated RNA molecule. In one embodiment, the RNA segment that binds the protein has at least about 80% nucleotide sequence identity to SEQ ID NO:8, 9 or 10. In one embodiment, the RNA segment that binds the protein has at least about 80% nucleotide sequence identity to SEQ ID NO:9 or 10. The protein that is bound by this RNA segment has at least 80% amino acid sequence identity to SEQ ID NO:5 or portion thereof, e.g., a portion having SEQ ID NO:6 or 7. In one embodiment, the protein that binds the RNA has at least 90% amino acid sequence identity to SEQ ID NO:5 or the portion thereof. In one embodiment, the endonuclease is Spo11, i-TEV1, i-Sce1, HO, or Fok1 or a portion thereof with nuclease activity. In one embodiment, the endonuclease has at least 80% amino acid sequence identity to SEQ ID NO:1. In one embodiment, the third isolated DNA molecule is fused to the fourth isolated DNA molecule or the third isolated RNA molecule is fused to the fourth isolated RNA molecule, so as to encode a fusion protein having the endonuclease or the portion thereof and the protein having at least 80% amino acid sequence identity to SEQ ID NO:5 or the portion thereof. In one embodiment, the isolated endonuclease or the portion thereof is fused to the protein having at least 80% amino acid sequence identity to SEQ ID NO:5 or the portion thereof. In one embodiment, the endonuclease or the portion thereof is N-terminal to the protein having at least 80% amino acid sequence identity to SEQ ID NO:5 or the portion thereof. In one embodiment, the endonuclease or portion thereof is C-terminal to the protein having at least 80% amino acid sequence identity to SEQ ID NO:5 or the portion thereof. In one embodiment, the RNA segment that binds the protein is about 300 to about 1600, or about 400 to about 1000, nucleotides in length. In one embodiment, the targeting RNA sequence is about 15 to about 500, for example about 15 to about 200 or about 20 to about 100, nucleotides in length. In one embodiment, the first isolated RNA molecule and the second isolated RNA molecule each further comprise complementary sequences at the 3' end and 5' end, respectively. In one embodiment, the complementary sequences are about 15 to about 500, for example about 20 to about 200 or about 20 to about 200, nucleotides in length. In one embodiment, the endonuclease or the portion thereof is fused to a first protein that binds to a second protein, wherein the protein having at least 80% amino acid sequence identity to SEQ ID NO:5 or the portion thereof is fused to the second protein, wherein the first protein and the second protein bind to each other. In one embodiment, the first or the second protein comprises GST, c-fos, c-jun, a protein that binds SH2 or SH3 domains, FRT, or FKBP12.

In one embodiment, a method for editing a target sequence at a locus in a host cell is provided. In one embodiment, the method includes introducing to a host cell one or more of: a first isolated DNA molecule having a DNA segment encoding a targeting RNA sequence or a first isolated RNA molecule comprising the targeting RNA sequence; a second isolated DNA molecule having a DNA segment encoding a RNA segment that binds a protein having at least 80% amino acid sequence identity to SEQ ID NO:5 or a second isolated RNA molecule comprising the RNA segment; a third DNA molecule having a DNA segment encoding an endonuclease or a portion thereof with nuclease activity or a third isolated RNA molecule encoding the endonuclease or the portion thereof, or an isolated polypeptide comprising the endonuclease or the portion thereof with nuclease activity; a fourth isolated DNA molecule having a DNA segment encoding the protein having at least 80% amino acid sequence identity to SEQ ID NO:5 or a portion thereof that binds the RNA segment, a fourth isolated RNA molecule encoding the protein having at least 80% amino acid sequence identity to SEQ ID NO:5 or the portion thereof, or an isolated polypeptide comprising the protein having at least 80% amino acid sequence identity to SEQ ID NO:5 or the portion thereof; an isolated double stranded DNA molecule having DNA having at least one nucleotide sequence capable of binding to a target sequence a locus, which nucleotide sequence may include a target sequence interrupted with one or more heterologous nucleotides, such as a selectable gene, or include sequences that bind to but do not have 100% nucleic acid sequence identity to the target sequence, e.g., so that the editing substitutes one or more nucleotides, deletes one or more nucleotide or inserts one or more nucleotides relative to the target sequence at the locus; and identifying cells with genomes that have been edited. In one embodiment, the host cell is a plant, yeast, algae or fungal cell. In one embodiment, the yeast cell is a haploid cell. In one embodiment, the fungus is *Aspergillus*. In one embodiment, cells having one or more nucleotide substitutions or insertions, or a deletion of target sequences, or any combination thereof, and optionally expressing a selectable gene that may be linked to the nucleotide sequence in the isolated double stranded DNA molecule, are isolated.

After delivery of the components to a cell, the targeting RNA sequence binds to the target sequence (locus) in the genome. As the targeting RNA sequence is linked to the RNA segment, this brings the protein that binds the RNA segment to the region of interest. The RNA segment may be bound by the protein before or after the targeting RNA sequence binds to the target sequence in the locus in the genome. In one embodiment, Mei2 binds to meiRNA. The binding of the targeting RNA sequence-RNA segment complex to the locus recruits the polypeptide component, e.g., a Mei2-Spo11 fusion protein, to the target sequence at the locus to be edited. An endonuclease, e.g., Spo11, then cuts the DNA and the DNA component (editing piece of DNA) is inserted at the target sequence to fix the break. The DNA component may be used to change the sequence of the original gene or DNA region, insert a new gene or genes or DNA region, or insert a segment of DNA to delete the original gene or DNA region.

This system can be used to target any region of the genome and is not limited by the need for specific sequences near the cleavage site, e.g., a PAM site, such is required by the CRISPR system. Moreover, the targeting RNA sequence used in this system can be greater than 20 nucleotides, which can lead to a more specific targeting system. Further, in a system that employs Spo11 or a homolog thereof, Spo11 cuts the DNA randomly and does not need a specific DNA sequence, and does not include an apparent nuclear localization sequence.

EXAMPLES

Example 1

Disruption of the ADE2 gene in *S. cerevisiae* was used as a target gene for genome editing because deletion or disruption of the ADE2 gene causes colonies to turn pink, thereby providing an easy method to screen for correctly targeted ade2 mutants.

To disrupt a gene, PCR was used to generate a DNA fragment that contains a selectable marker, e.g., nutritional markers such as URA3 and HIS3 or the antibiotic resistance gene hygromycin resistance (hph). The 5' end of the PCR fragment contains about 40 to about 75 nucleotides of homology to the gene of interest, e.g., the ADE2 gene, on the 5' side of the region that is targeted. Similarly, the 3' end of the PCR fragment consists of sequences of interest, e.g., ADE2 sequences, on the 3' side of the region that is targeted.

As described below, several different selectable markers individually in independent experiments were successfully introduced into the ADE2 gene of a haploid *S. cerevisiae* strain. The hygromycin marker (hph), the URA3 and HIS3 genes were each inserted with up to 100% efficiency when the entire genome editing system is transformed along with a DNA cassette containing the resistance marker or nutritional markers.

Materials and Methods
Background Strains and Plasmids:
MT502 (MATa, sst 2-1, his3, leu2-3, 112, met1, can1)
ATCC 201389 (MATalpha, his3, leu2, lys2, ura3)
pRS313 and pRS316 plasmids: See Sikorski R S, Hieter P. (1989) *Genetics*. 122(1):19-27.

Lithium acetate transformation: transformation of yeast employed the LiAc/SS carrier DNA/PEG method (Gietz R D, Schiestl R H. (2007) Nat Protoc. 2(1):31-4).

Plasmid assembly: The TDH3 promoter and CYC terminator from *Saccharomyces cerevisiae* were amplified from genomic DNA and fused together by PCR, creating an XbaI/PacI junction in between the promoter and terminator by incorporation of these sites in the primers used to amplify the DNA. The $P_{TDH3}$-XbaI-PacI-Tcyc DNA was cloned into pRS316 (Sikorski and Hieter, 1989) creating plasmid pAV69. The in-frame polypeptide fusions were created using gBlocks (Integrated DNA Technologies (IDT), Coralville, Iowa) in which segments of the polypeptide coding DNA were produced separately with overlapping homologous flanks. The gBlocks were fused together to create the SPO11-MEI2 and MEI2-SPO11 fusions via PCR using primers that annealed to the ends of the completed sequence. The polypeptide fusion genes were then cloned into plasmid pAV69 using XbaI/PacI ligation, inserting the fused gene between the promoter and the terminator. One plasmid was created with the SPO11-MEI2 fusion, and one with the MEI2-SPO11 fusion. These two plasmids, containing the genes encoding the fused polypeptides cloned in between regulatory elements were then used as the backbones for further cloning of the meiRNA-S gRNA elements. The TDH3 promoter and CYC terminator from *S. cerevisiae* were again amplified and fused together by PCR while creating a BmtI/AvrII junction in between the promoter and terminator by incorporation of these sites in the primers used to amplify the DNA. The $P_{TDH3}$-BmtI-AvrII-Tcyc DNA was cloned into each of the backbones containing the SPO11/MEI2 and MEI2/SPO11 fusions using SacI/NotI ligation. The DNA for the fusions expressing meiRNA-S+targeting RNA sequence of 20 bp, 45 bp or 70 pb were designed as gBlocks and cloned into the BmtI/AvrII site in each of the two Spo11 and Mei2 fusion plasmid backbones to complete the genome editing plasmids listed in Table 1.

TABLE 1

Genome editing plasmids

| Plasmid Name | Plasmid Selection | Polypeptide fusion | Promoter to express RNA component | RNA segment in RNA component | Targeting RNA sequence length in RNA component | Target gene |
|---|---|---|---|---|---|---|
| pEST7 | URA3 | Spo11-Mei2 | TDH3 | meiRNA | None | — |
| pEST9 | URA3 | Spo11-Mei2 | TDH3 | meiRNA | 20 b | ADE2 |
| pEST11 | URA3 | Spo11-Mei2 | TDH3 | meiRNA | 45 b | ADE2 |
| pEST13 | URA3 | Spo11-Mei2 | TDH3 | meiRNA | 70 b | ADE2 |
| pEST8 | URA3 | Mei2-Spo11 | TDH3 | meiRNA | None | — |
| pEST10 | URA3 | Mei2-Spo11 | TDH3 | meiRNA | 20 b | ADE2 |
| pEST12 | URA3 | Mei2-Spo11 | TDH3 | meiRNA | 45 b | ADE2 |
| pEST14 | URA3 | Mei2-Spo11 | TDH3 | meiRNA | 70 b | ADE2 |
| pPS001 | URA3 | Spo11-Mei2 | TDH3 | meiRNA | 45 b | CAN1 |
| pPS002 | URA3 | Mei2-Spo11 | TDH3 | meiRNA | 45 b | CAN1 |

Further modifications of plasmids: Creation of GFP (green fluorescent protein) fused to the C-terminus of the hybrid polypeptides: The SPO11 MEI2-GFP and MEI2-SPO-GFP fusions were created by replacing the SPO11-MEI2 and MEI2-SPO11 fusions using a PCR amplified GFP. The GFP gene to be fused contained overlaps to existing sequence within the upstream region. A recombination cloning approach in which the plasmid and the GFP containing DNA were each cut with two enzymes and reassembled via recombination after transformation into *S. cerevisiae*. The resulting plasmids are described in Table 2.

TABLE 2

Genome editing plasmids with GFP fusion proteins

| Plasmid Name | Plasmid Selection | Polypeptide fusion | Promoter to express RNA component | RNA segment in RNA component | Targeting RNA sequence length in RNA component | Target gene |
|---|---|---|---|---|---|---|
| pPS015 | URA3 | Spo11-Mei2-GFP | TDH3 | meiRNA | None | — |
| pPS017 | URA3 | Spo11-Mei2-GFP | TDH3 | meiRNA | 20 b | ADE2 |
| pPS019 | URA3 | Spo11-Mei2-GFP | TDH3 | meiRNA | 45 b | ADE2 |

TABLE 2-continued

Genome editing plasmids with GFP fusion proteins

| Plasmid Name | Plasmid Selection | Polypeptide fusion | Promoter to express RNA component | RNA segment in RNA component | Targeting RNA sequence length in RNA component | Target gene |
|---|---|---|---|---|---|---|
| pPS021 | URA3 | Spo11-Mei2-GFP | TDH3 | meiRNA | 70 b | ADE2 |
| pPS016 | URA3 | Mei2-Spo11-GFP | TDH3 | meiRNA | None | — |
| pPSO18 | URA3 | Mei2-Spo11-GFP | TDH3 | meiRNA | 20 b | ADE2 |
| pPS020 | URA3 | Mei2-Spo11-GFP | TDH3 | meiRNA | 45 b | ADE2 |
| pPS022 | URA3 | Mei2-Spo11-GFP | TDH3 | meiRNA | 70 b | ADE2 |
| pPS023 | URA3 | Spo11-Mei2-GFP | TDH3 | meiRNA | 45 b | CAN1 |
| pPS024 | URA3 | Mei2-Spo11-GFP | TDH3 | meiRNA | 45 b | CAN1 |

Expression of meiRNA-S+taretin RNA sequence RNAs from SNR52 promoter: RNA polymerase III (Pol III) promoters are commonly used to express small RNAs. To test use of a Pol III promoter for expression of the RNA component having meiRNA-S based RNA and targeting RNA sequences, the SNR52 promoter and SNR52 terminator from *S. cerevisiae* were amplified and fused together by PCR while creating an BmtI/AvrII junction in between the promoter and terminator and SacI/NotI sites on the ends. The $P_{SNR52}$-BmtI-AvrII-$T_{SN52}$ DNA was cloned into each of the backbones containing the SPO11/MEI21GFP fusions created previously using SacI/NotI ligation. The fusions of DNA for meiRNA-S+targeting RNA sequences of 20 bp, 45 bp or 70 bp, were synthesized in their entirety as gBlocks (IDT, Coralville, Iowa) and cloned into the BmtI/AvrII site in each of the two SPO11/MEI2/GFP fusion plasmid backbones to complete the genome editing plasmids listed in Table 3.

TABLE 3

Genome editing plasmids with gRNA expressed from the SNR52 promoter.

| Plasmid Name | Plasmid Selection | Polypeptide fusion | Promoter to express RNA component | RNA segment in RNA component | Targeting RNA sequence length in RNA component | Target gene |
|---|---|---|---|---|---|---|
| pAVT7 | URA3 | Spo11-Mei2-GFP | SNR52 | meiRNA | 20 b | ADE2 |
| pAVT9 | URA3 | Spo11-Mei2-GFP | SNR52 | meiRNA | 45 b | ADE2 |
| pAVT11 | URA3 | Spo11-Mei2-GFP | SNR52 | meiRNA | 70 b | ADE2 |
| pAVT8 | URA3 | Mei2-Spo11-GFP | SNR52 | meiRNA | 20 b | ADE2 |
| pAVT10 | URA3 | Mei2-Spo11-GFP | SNR52 | meiRNA | 45 b | ADE2 |
| pAVT12 | URA3 | Mei2-Spo11-GFP | SNR52 | meiRNA | 70 b | ADE2 |

Creating Histidine selectable genome editing plasmids: To create hisitidine-selectable versions of the genome editing plasmids, pRS313 (Sikorski and Hieter, 1989) was cut with SacI/XhoI and ligated to the fragments of the genome editing plasmids cut with the same enzymes. This effectively exchanged the selectable markers as well as the general backbone of the plasmids while leaving the genome editing elements identical to those used previously.

TABLE 4

Histidine selectable genome editing plasmids.

| Plasmid Name | Plasmid Selection | Polypeptide fusion | Promoter to express RNA component | RNA segment in RNA component | Targeting RNA sequence length in RNA component | Target gene |
|---|---|---|---|---|---|---|
| pPS007 | HIS3 | Spo11-Mei2 | TDH3 | meiRNA | None | — |
| pPS009 | HIS3 | Spo11-Mei2 | TDH3 | meiRNA | 20 b | ADE2 |
| pPS011 | HIS3 | Spo11-Mei2 | TDH3 | meiRNA | 45 b | ADE2 |
| pPS013 | HIS3 | Spo11-Mei2 | TDH3 | meiRNA | 70 b | ADE2 |
| pAVT7 | HIS3 | Spo11-Mei2 | SNR52 | meiRNA | 20 b | ADE2 |
| pAVT9 | HIS3 | Spo11-Mei2 | SNR52 | meiRNA | 45 b | ADE2 |
| pAVT11 | HIS3 | Spo11-Mei2 | SNR52 | meiRNA | 70 b | ADE2 |
| pPS008 | HIS3 | Mei2-Spo11 | TDH3 | meiRNA | None | — |
| pPS010 | HIS3 | Mei2-Spo11 | TDH3 | meiRNA | 20 b | ADE2 |
| pPS012 | HIS3 | Mei2-Spo11 | TDH3 | meiRNA | 45 b | ADE2 |
| pPS014 | HIS3 | Mei2-Spo11 | TDH3 | meiRNA | 70 b | ADE2 |
| pAVT8 | HIS3 | Mei2-Spo11 | SNR52 | meiRNA | 20 b | ADE2 |
| pAVT10 | HIS3 | Mei2-Spo11 | SNR52 | meiRNA | 45 b | ADE2 |
| pAVT12 | HIS3 | Mei2-Spo11 | SNR52 | meiRNA | 70 b | ADE2 |

Results

The evaluation of fusion protein functionality in *S. cerevisiae* MT502 cells was assessed after transforming the cells using lithium acetate/PEG transformation (Geitz and Schiestl, 2007) with 200-300 ng of various plasmid constructs containing GFP tagged fusion polypeptides in order to visualize the cellular localization (FIG. 1). After transformation cells expressing various Spo11-Mei2 and Mei2-Spo11 fusion proteins were wet mounted from fresh ScD-ura liquid and observed using fluorescence microscopy to determine cellular localization of the fusion protein. A Zeiss Axioplan2 or a Leica microscope was used at 100× magnification and a green filter to visualize the GFP-fused proteins. Plasmids are listed in Table 2.

FIG. 1 shows images of cells expressing those plasmids. Two orientations were tested, orientation A (Spo11-Mei2) (FIGS. 1A-D), and orientation B (Mei2-Spo11) (FIG. 1E-H). FIG. 1A) shows GFP fluorescence with no targeting RNA sequence (but includes the meiRNA sequence) construct (pPS015); FIG. 1B) shows GFP fluorescence with meiRNA fused to a 20 b targeting RNA sequence (pPS017); FIG. 1C) shows GFP fluorescence with meiRNA fused to a 45 b targeting RNA sequence construct (pPS019); and FIG. 1D) shows GFP fluorescence with meiRNA fused to a 70 b targeting RNA sequence (pPSO21).

FIG. 1E) shows GFP fluorescence with no targeting RNA sequence (but includes the meiRNA sequence) (pPS016); FIG. 1F) shows GFP fluorescence with meiRNA fused to a 20 b targeting RNA sequence (pPS018); FIG. 1G) shows GFP fluorescence with meiRNA fused to a 45 b target sequence (pPS020); and FIG. 1H) shows GFP fluorescence with meiRNA fused to a 70 b target sequence construct (pPS022).

In Panels A and E, GFP is diffuse, indicating the fusion protein is dispersed throughout the cytoplasm. The fusion proteins were expressed, but not targeted within the cells because there was no targeting RNA sequence present. In Panels B, C, D, F, G, and H, the localization of the fusion protein is more pronounced with increasing lengths of the targeting RNA sequence. As homology to the target gene increases in length via the targeting RNA sequence, the concentration of the GFP-tagged Spo11/Mei2 fusion proteins in the nucleus increases.

Thus, the results show that the Spo11-Mei2 fusion protein is only localized to the nucleus when meiRNA-S is present, and greater concentrations are targeted to the nucleus in response to increased lengths of RNA homology on the targeting RNA sequence. Both orientations of the fusion protein were capable of nuclear localization in the presence of the targeting RNA sequence.

FIG. 2 shows data for integration efficiency of constructs, using hph as the functional selection marker, targeting the ADE2 gene using varying lengths of homology on the targeting RNA sequence in *S. cerevisiae* MT502. Genome editing plasmids were delivered at 200 ng alone and in combination with 3 μg of a PCR-generated hph cassette targeted to ADE2 with 45 bp homology ends. The DNA having 40 bp ADE2 homology arms flanking the hph gene, was delivered in the absence of the genome editing system plasmid as a control for necessity of the editing system for accurate integration (labelled hph on graphs). The control transformations labelled "0" consist of cells treated using the lithium acetate/PEG transformation procedure (Geitz and Schiestl, 2007), but no plasmid or DNA component was added to the cells.

Figures 2A, 2B:
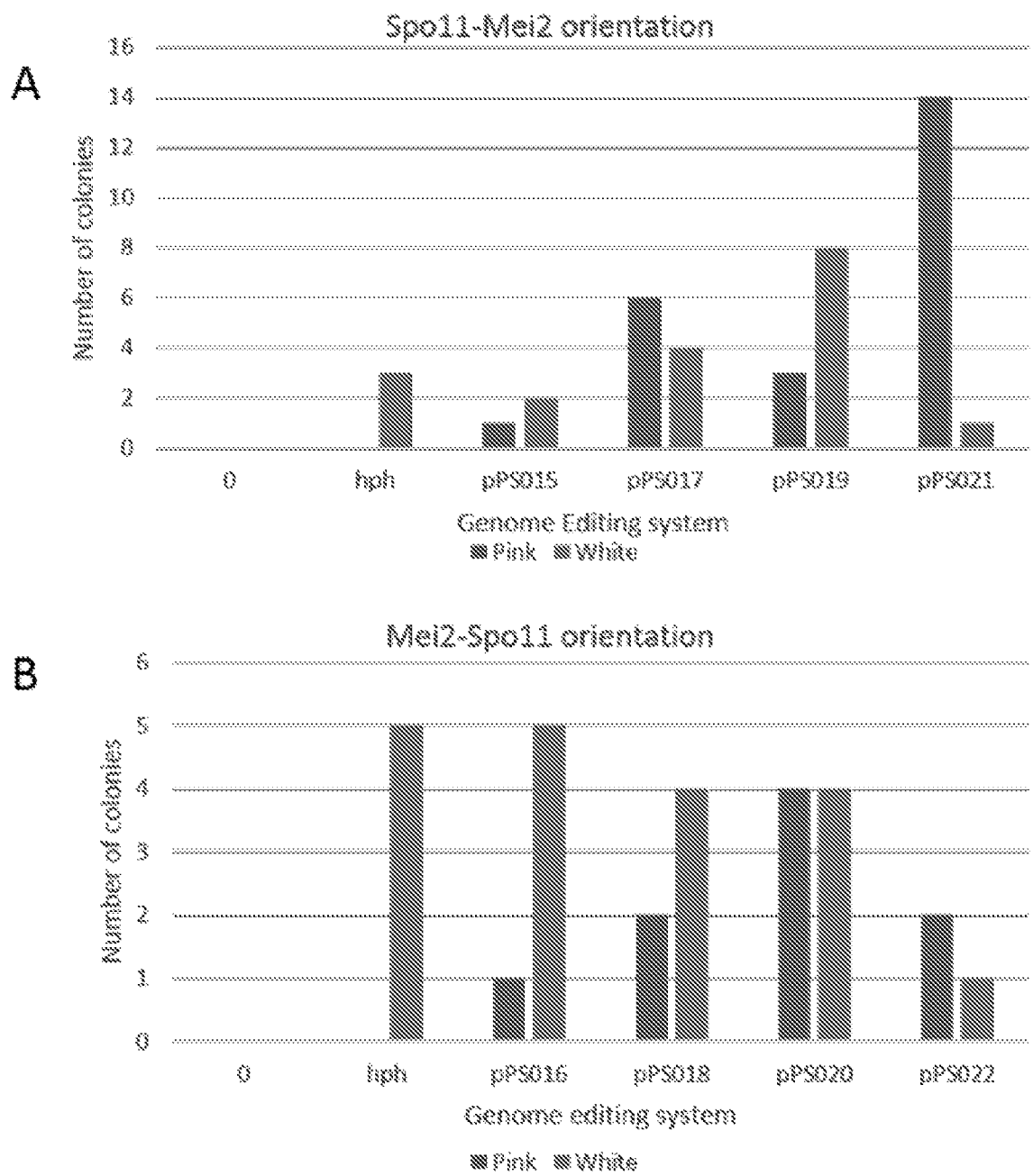
FIGS. 2A-2B. The hph gene is a functional selection marker for use in the genome editing system. Constructs targeting the ADE2 gene with varying lengths of targeting RNA sequence fused to meiRNA-S were tested for integration efficiency in S. cerevisiae. S. cerevisiae MT502 (Marioroni et al., J. Bacteriol., 181:6488 (1999)) cells were transformed using a standard lithium acetate/PEG transformation (Geitz and Schiestl, 2007). A) Transformations using Spo11-Mei2 fusion protein plasmids. Pink colonies indicate the ADE2 is accurately targeted. White colonies indicate the resistance marker integrated off-target. B) Transformations using Mei2-Spo11 fusion protein plasmids. Pink colonies indicate the ADE2 is accurately targeted. White colonies indicate the resistance marker integrated off-target.

FIG. 2A shows the number of colonies with transformations using SPO11/MEI2 fusion plasmids. FIG. 2B shows the number of colonies with transformation using MEI2/SPO11 fusion plasmids. Pink colonies indicate the ADE2 is accurately targeted and edited by integration of the resistance marker. White colonies indicate the resistance marker integrated off-target. Only white colonies were seen when the genome editing system components were not expressed in the cells along with the targeting DNA (hph vs. +plasmids). SPO11/MEI2 alone (pPS015 and pPS016) enables some targeting of the integration construct to the ADE2 gene. Both orientations of MEI2/SPO11 and MEI2/SPO11 fusions enable increased targeting of the integration DNA to ADE2.

The results in FIG. 3 illustrate use of the URA3 gene as a functional selection marker for use in the genome editing system. Constructs targeting the ADE2 gene using varying lengths of homology on the RNA were tested for integration efficiency in S. cerevisiae. S. cerevisiae ATCC 201389 cells were transformed using a standard lithium acetate/PEG transformation (Geitz and Schiestl, 2007). Genome editing plasmids were delivered at 200 ng alone and in combination with 3 μg of the DNA component, a PCR-generated URA3 cassette targeted to ADE2 with 40 bp homology ends. The DNA component containing 40 bp homology arms flanking the hph gene was delivered in the absence of the genome editing system plasmid as a control for necessity of the editing system for accurate integration (labelled URA3 on graphs). The control transformations labelled "0" on the graphs consisted of cells treated using the lithium acetate/PEG transformation procedure, but no plasmid or targeting DNA was added to the cells.

Figures 3A, 3B:
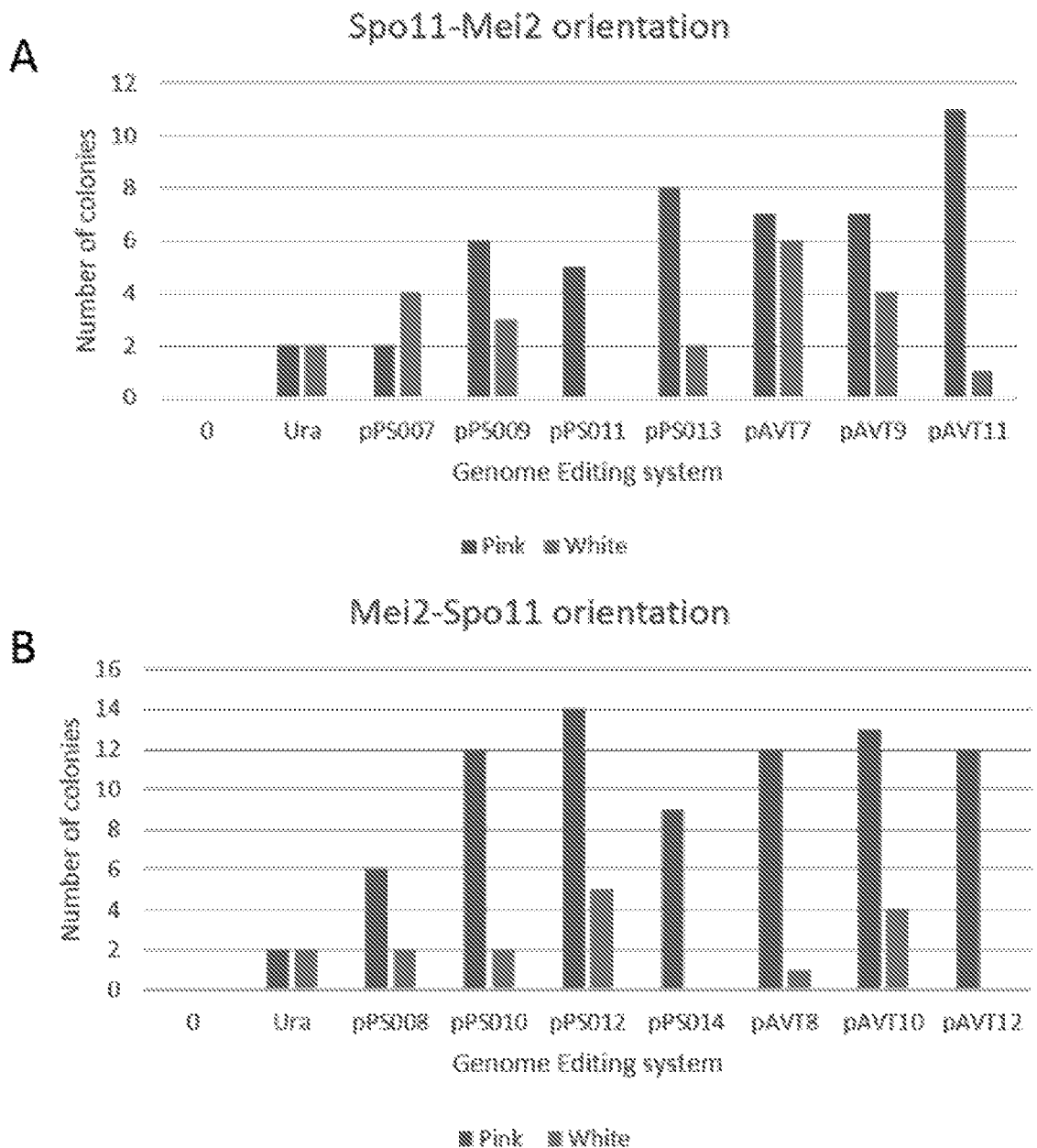
FIGS. 3A-3C. The URA3 gene is a functional selection marker for use in the genome editing system. Constructs targeting the ADE2 gene with varying lengths of targeting RNA sequence fused to meiRNA-S were tested for integration efficiency in S. cerevisiae. S. cerevisiae ATCC 201389 cells were transformed using a standard lithium acetate/PEG transformation (Geitz and Schiestl, 2007). A) Transformations using Spo11-Mei2 fusion protein plasmids. Pink colonies indicate the ADE2 is accurately targeted. White colonies indicate the resistance marker integrated off-target. B) Transformations using Mei2-Spo11 fusion protein plasmids. Pink colonies indicate the ADE2 is accurately targeted. White colonies indicate the resistance marker integrated off-target. C) Photos of plates with pink/white colonies post-transformation.
Figure 3C:
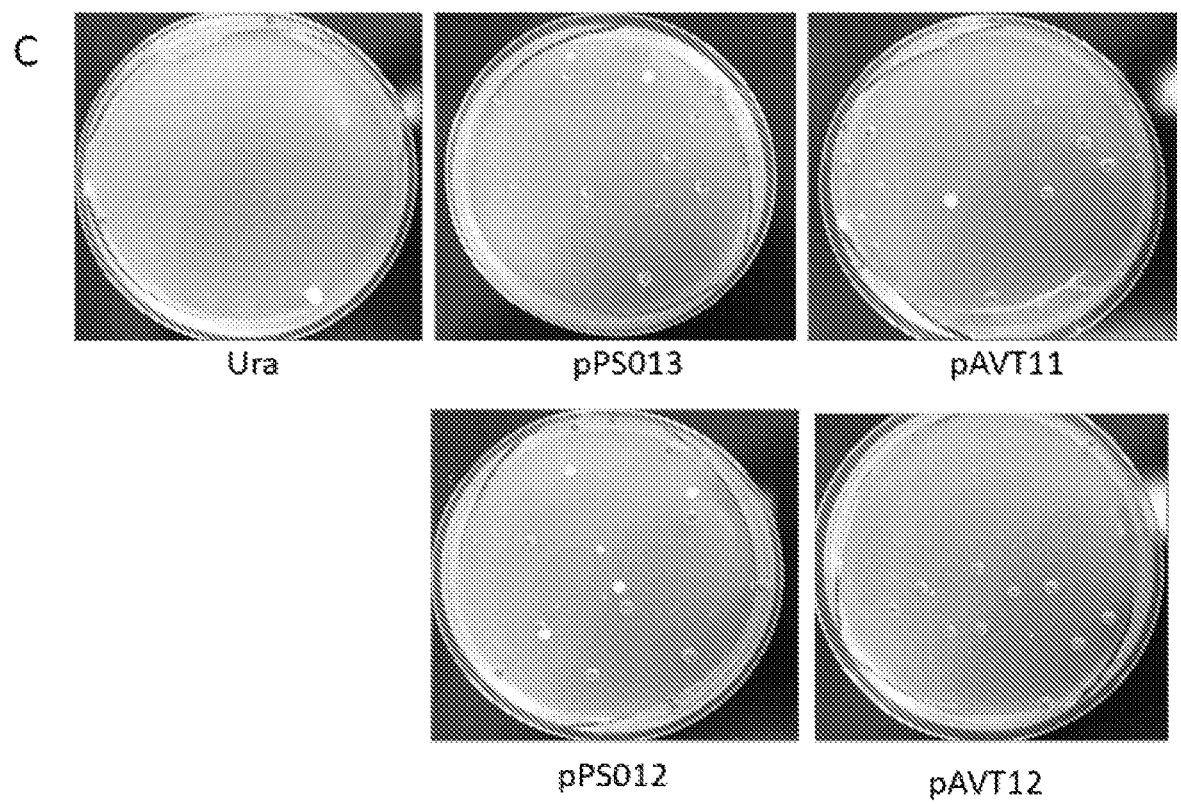

FIG. 3A shows transformations using MEI2/SPO11 fusion plasmids. Pink colonies indicate the ADE2 is accurately targeted. White colonies indicate the resistance marker integrated off-target. FIG. 3B shows transformations using Mei2-Spo11 fusion protein plasmids. Pink colonies indicate the ADE2 is accurately targeted. White colonies indicate the resistance marker integrated off-target. FIG. 3C shows images of representative plates with pink/white colonies post-transformation.

ADE2-targeted URA3 selectable linear DNA is able to disrupt ADE2 50% of the time in the absence of a genome editing system (URA3 vs. all others in A and B—equal numbers of white and pink colonies). Addition of the genome editing system and increased lengths of ADE2 homology on the targeting RNA sequence results in increased targeting specificity. Delivery of pPS011, pAVT11, pPS14 and pAVT12 in particular result in high targeted disruption efficiency. Neither orientation of the SPO11/MEI2 fusion is favored when URA3 is the selectable marker used in ATCC 201389. Both the TDH3 and SNR52 promoters were effective at directing expression of the RNA component.

The genome editing system described herein may be used to create gene deletions or other edits through the process of repairing the double strand break using an endonuclease other than Spo11, e.g. i-Tev1, i-Sce1, HO, or Fok1 (these endonucleases require a specific site in the DNA to which they bind, once bound to the DNA, these proteins then cleave the DNA at specific DNA sequences). In one embodiment, the DNA binding portion of endonucleases other than Spo11 may be replaced with a RNA-binding protein, e.g., Mei2. In addition, RNA:RNA-binding protein pairs other than meiRNA:Mei2 may be employed, including but are not limited to, proteins such as Maxi-DH, KH-like, PUF (fem-3, gld-1, gld-3s, fbf-1, fbf-2), nanos RNA binding (gld-1), RRM, Zn-finger (nos-2, glp-1, fog-1), KH (pal-1), RGG box or DEAD/DEAH box.

Example 2

The genome editing system disclosed above was applied to a Issatchenkia orientalis diploid strain. Genome editing was used to disrupt the ADE2 gene in Issatchenkia orientalis. Disruption of the ADE2 gene in Issatchenkia orientalis was used as a target gene for genome editing because deletion or disruption of the ADE2 gene causes colonies to turn pink, thereby providing an easy method to screen for correctly targeted ade2 mutants. To disrupt the ADE2 gene, PCR was used to generate a DNA fragment that contains the URA3 selectable marker and 5' and 3' overhangs with nucleotides bearing homology to the ADE2 gene. The described genome editing system resulted in targeting of the ADE2 gene and its replacement with the URA3 selectable marker.

As described below, several different selectable markers individually in independent experiments were successfully introduced into the ADE2 gene of a haploid S. cerevisiae strain. The hygromycin marker (hph), the URA3 and HIS3 genes were each inserted with up to 100% efficiency when the entire genome editing system is transformed along with a DNA cassette containing the resistance marker or nutritional markers.

Construction of new AES plasmids with ADE2 guides and amplification of URA3 knockout fragments in Issatchenkia orientalis.

Figure 4:
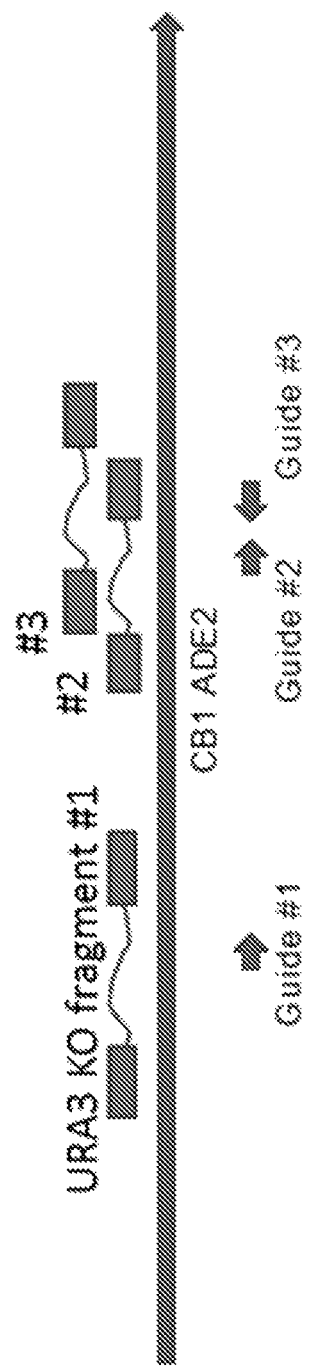
FIG. 4 shows where of each of Guide #1 (SEQ ID NO:34), Guide #2 (SEQ ID NO:35), and Guide #3 (SEQ ID NO:36) possess homology relative to the ADE2 locus.

Weak and strong promoter plasmids were constructed to evaluate new target sequences selected to target the ADE2 locus. Plasmids pVY047 and pVY053, were utilized as the base plasmids. The plasmids differ only in that plasmid pVY047 comprises a weak promoter and plasmid pVY053 comprises a strong promoter. Each plasmid was digested with NheI/AvrII and purified by gel electrophoresis to remove the excised fragment. Inserts comprising new target sequences, referred to as "guides" (e.g., Guide #1, Guide #2, and Guide #3) were inserted into the respective plasmids using HiFi enzyme (New England Biolabs). The three ADE2 guides are 45 bp in length and correspond to sequences ~500 bp, ~1000 bp, and ~1120 bp downstream of the 5' start of the locus. FIG. 4 shows where of each of Guide #1 (SEQ ID NO:34), Guide #2 (SEQ ID NO:35), and Guide #3 (SEQ ID NO:36) possess homology relative to the ADE2 locus. Each insert also comprised the nucleotides to encode the meiRNA segment. PCR was used to confirm that the six resulting plasmids comprised the respective guide. The six resulting plasmids are listed below in Table 4.

TABLE 4

| Plasmid | Description |
| --- | --- |
| pCME007 | pVY047 + ADE2 guide #1 (−500-545bp) |
| pCME008 | pVY047 + ADE2 guide #2 (−1001-1045bp) |
| pCME009 | pVY047 + ADE2 guide #3 (−1120-1067bp) |
| pCME010 | pVY053 + ADE2 guide #1 (−500-545bp) |
| pCME011 | pVY053 + ADE2 guide #2 (−1001-1045bp) |
| pCME012 | pVY053 + ADE2 guide #3 (−1120-1076bp) |

URA3 integration fragments containing ADE2 targeting homology were prepared by PCR using three sets of ultramer primers. Each ultramer primer comprised ~180 bp of homology to the ADE2 gene. PCR was performed with the respective ultramer primer set against the URA3 expression cassette from pHJJ28 using Failsafe polymerase to generate the URA3 integration fragments. The first URA3 integration fragment (URA3 KO fragment #1) was generated with A primer set oCME010 (SEQ ID NO: 28) and oCME011 (SEQ ID NO: 29). The second URA3 integration fragment (URA3 KO fragment #2) was generated with a primer set oCME012 (SEQ ID NO: 30) and oCME013 (SEQ ID NO: 31). The third URA3 integration fragment (URA3 KO fragment #3) was generated with a primer set oCME014 (SEQ ID NO: 32) and oCME015 (SEQ ID NO: 33). FIG. 4 shows the where each of the first, second, and third URA3 integration fragments correspond relative to the ADE2 gene.

slurry is transferred to a 1.5 mL microfuge tube. Each respective transformation is then plated on a ScD-Ura plate and incubated at 30° C. for 5 days.

The incubated plates were then inspected for growth of colonies and white and red colonies were counted. Red colonies corresponded to successful genome editing at the ADE2 locus with disruption of the ADE2 locus and integration of URA3. White colonies corresponded to unsuccessful attempts. The % on target referred to the percentage of successful attempts (red colonies) compared to unsuccessful attempts (white colonies). The results are shown below in Table 5.

TABLE 5

| | | | | | | | | | |
|---|---|---|---|---|---|---|---|---|---|
| | | | | Electroporation | | | | | |
| Strain | AES | amount | volume | ADE 2 KO | amount | volume | # white | # red | % on target |
| 14545 | pCME007 | 200 ng | 1 | #1 | 250 ng | 1.5 | 205 | 2 | 1.0% |
| 14545 | pCME008 | 200 ng | 1 | #2 | 250 ng | 1.3 | 172 | 8 | 4.4% |
| 14545 | pCME009 | 200 ng | 1 | #3 | 250 ng | 1.3 | 292 | 7 | 2.3% |
| 14545 | pCME010 | 200 ng | 1 | #1 | 250 ng | 1.3 | 183 | 3 | 1.6% |
| 14545 | pCME011 | 200 ng | 1 | #2 | 250 ng | 1.5 | 169 | 5 | 2.9% |
| 14545 | pCME012 | 200 ng | 1 | #3 | 250 ng | 1.3 | 441 | 11 | 2.4% |
| 14545 | pCME007 | 1 ug | 5 | #1 | 250 ng | 1.5 | 88 | 1 | 1.1% |
| 14545 | pCME008 | 1 ug | 5 | #2 | 250 ng | 1.3 | 55 | 1 | 1.8% |
| 14545 | pCME009 | 1 ug | 5 | #3 | 250 ng | 1.3 | 275 | 3 | 1.1% |
| 14545 | pCME010 | 1 ug | 5 | #1 | 250 ng | 1.3 | 55 | 4 | 6.8% |
| 14545 | pCME011 | 1 ug | 5 | #2 | 250 ng | 1.5 | 78 | 0 | 0.0% |
| 14545 | pCME012 | 1 ug | 5 | #3 | 250 ng | 1.3 | 120 | 8 | 6.3% |
| 14545 | — | — | — | #1 | 250 ng | 1.5 | 367 | 2 | 0.5% |
| 14545 | — | — | — | #2 | 250 ng | 1.3 | 412 | 2 | 0.5% |
| 14545 | — | — | — | #3 | 250 ng | 1.3 | 484 | 2 | 0.4% |
| 14545 | — | — | — | — | — | — | 0 | 0 | |

Electroporation of CD14545 with genome editing components targeting the ADE2 locus

*Issatchenkia orientalis* strain CD14545 was plated on a fresh YPD plate from a frozen glycerol stock. A single colony was used to start an 50 mL overnight liquid culture that was grown overnight in a 250 mL baffled shake flask at 30° C. with an agitation of 250 RPM. The following morning the flasks were diluted back to an OD600 of 0.02 and placed back in the shaker. Once the flask achieved an OD600 of 0.25 the culture was transferred to a 50 mL falcon tube and centrifuged at 4000 RPM for 5 minutes. The supernatant was decanted and replaced with 25 mL of Incubation Buffer containing: 625 µl 1M LioAc, 2.5 mL TE buffer (100 mM Tris, 10 mM EDTA pH 8.0), 250 µl 1M DTT, and 21.625 mL sterile water. The cell slurry is left at room temperature for 30 minutes, than centrifuged at 4000 RPM for 5 minutes in a 4° C. centrifuge. The Incubation Buffer was decanted, and the cell pellet washed twice in ice-cold sterile water by resuspension in 25 mL ice-cold sterile water and centrifugation at 4000 RPM for 5 minutes in a 4° C. centrifuge. The resulting cell pellet was resuspended in 1 mL ice-cold 1M sorbitol. To a pre-chilled 0.1 mM electroporation cuvette, 40 µl of cell slurry was added, along with a predetermined amount of DNA. The predetermined amount of DNA comprised one of pCME007-pCME012 and a specific URA3 integration fragment. Controls were also prepared with only a specific URA3 integration fragment and not any of pCME007-pCME012. Another control was prepared with neither of a URA3 integration fragment nor a pCME007-pCME012. The cuvette is electroporated using the following settings: 1.5 kV, 25 µF, 200Ω. After each transformation, 1 mL of ice-cold 1M sorbitol is added to the cuvette and the cell The results were analyzed by the respective target sequences (e.g., Guide #1, Guide #2, and Guide #3). The results are shown in Table 6.

TABLE 6

| | % on target in Diploid (14545) | | | | |
|---|---|---|---|---|---|
| | w/o AES | w/AES (200 ng) | | w/AES (1 ug) | |
| | — | weak | strong | weak | strong |
| Guide #1 | 0.5% | 1.6% | 1.0% | 6.8% | 1.1% |
| Guide #2 | 0.5% | 2.9% | 4.4% | 0.0% | 1.8% |
| Guide #3 | 0.4% | 2.4% | 2.3% | 6.3% | 1.1% |

The results were analyzed by the respective target sequences (e.g., Guide #1, Guide #2, and Guide #3) to show fold-improvement. The results are shown in Table 7.

TABLE 7

| | Fold-improvement | | | |
|---|---|---|---|---|
| | w/AES (200 ng) | | w/AES (1 ug) | |
| | weak | strong | weak | strong |
| Guide #1 | 3.0 | 1.8 | 12.5 | 2.1 |
| Guide #2 | 5.9 | 9.2 | — | 3.7 |
| Guide #3 | 5.9 | 5.7 | 15.2 | 2.6 |

The results showed that the genome editing system was able to successfully edit the genome of the diploid *Issatchenkia orientalis* strain. The genome editing system was able to successfully edit the genome of the diploid *Issatchenkia orientalis* strain CD14545 by disrupting the ADE2 locus and integrating the URA3 selectable marker. The genome editing system showed a percent targeting of between about 1 to 6.8% for weak and strong promoters. This corresponded to a fold-improvement of between 1.8 to 15.2 times.

REFERENCES

Watanabe, Y. and Yamamoto, M. (1994) *S. pombe* mei2+ encodes an RNA-binding protein essential for premeiotic DNA synthesis and meiosis I, which cooperates with a novel RNA species meiRNA. Cell (78): 487-498

Shichino, Y., Yamashita, A., and Yamamoto, M. (2014) Meiotic long non-coding meiRNA accumulates as a dot at its genetic locus facilitated by Mmi1 and plays as a decoy to lure Mmi1. Open Biology (4): 140022

Yamashita, A., Shichino, Y., Tanaka, H., Hiriart, E., Touat-Todeschini, L., Vavasseur, A., Ding, D.-Q., Hiraoka, Y., Verdel, A., and Yamamoto, M. (2012) Hexanucleotide motifs mediate recruitement of the RNA elimination machinery to silent meiotic genes. Open Biology (2): 120014

Kenney, S. (2008) Spo11 and the formation of DNA double-strand breaks in meiosis. Genome Dyn Stab. (2): 81-123

Keeney, S., Giroux, C. N., and Kleckner, N. (1997) Meiosis-specific DNA double-strain breaks are catalyzed by Spo11, a member of a widely conserved protein family. Cell (88): 375-384

All publications, patents and patent applications are incorporated herein by reference. While in the foregoing specification, this invention has been described in relation to certain embodiments thereof, and many details have been set forth for purposes of illustration, it will be apparent to those skilled in the art that the invention is susceptible to additional embodiments and that certain of the details herein may be varied considerably without departing from the basic principles of the invention.

SEQUENCES

SEQ ID NO: 1
Spo11-*Saccharomyces cerevisiae* S288C
MALEGLRKKYKTRQELVKALTPKRRSIHLNSNGHSNGTPCSNADVLAHIKHFLSLAANSLEQHQQ
PISIVFQNKKKKGDTSSPDIHTTLDFPLNGPHLCTHQFKLKRCAILLNLLKVVMEKLPLGKNTTV
RDIFYSNVELFQRQANVVQWLDVIRFNFKLSPRKSLNIIPAQKGLVYSPFPIDIYDNILTCENEP
KMQKQTIFPGKPCLIPFFQDDAVIKLGTTSMCNIVIVEKEAVFTKLVNNYHKLSTNTMLITGKGF
PDFLTRLFLKKLEQYCSKLISDCSIFTDADPYGISIALNYTHSNERNAYICTMANYKGIRITQVL
AQNNEVHNKSIQLLSLNQRDYSLAKNLIASLTANSWDIATSPLKNVIIECQREIFFQKKAEMNEI
DARIFEYK SEQ ID NO: 2
Spo11-*Saccharomyces bayanus*
MALHRLRKKHRTRQELLKALTPRTRSIHLSPNEHSNGSTSSNAEVLSHIKQILSLAANSLEQHQQ
PISIIFHNKTKGNSSGNSITTKLDFPLNGPHLFTHQFKLKRCSILLNLLKIVMEKLPLGQNTTIR
DIFYSNVELFQRQANVVQWLDVIRFNFKLSPRKSLNIIPAQKGLIYSPFPIYVYDSITKYEDDFR
VEKQTVSPGKPCLIPFFQDDAVIRLETTSHCNIVIVEKEAVFTKLVSTYNKLSANTVLITGKGFP
DFLTRLFLKKLEQNCSNLISNCSIFTDADPYGISIALNYINSNANAAYNCPMVNYKGVYITQILA
QNNRMGSKVVQLLSLNQRDYSLAKNLIVSLTNSGEGWSSPFKNFIVECQREIFFQKKAEMNEIDV
GMFQFX SEQ ID NO: 3
Spo11-*Candida glabrata*
MNFTLADIYDSADISELRARLTADKRAVFFSPVVDDNADKSQQIHNKIQDILTLCKNSVGQQQQG
FQLHGLFKKPIEFPLSGRLKGKLLQNKIQKLSITFTLLKEIQRNIEKCTAFTSRDIFYRNVELFK
SQRLVVDTVDHIQKALGLTIREDLNITATQKGLIFTAVDIIINSSDTKKIKITKGKSQLIPQFDS
NAFIMVCKDDPQMILKVLVIEKDAVYNTIIQKPTEGYIVVTGKGYPDMLTRKFLHRLEQCNSNLQ
FVILTDPDPHGINIAMKYQGFTTDSIYPCASLIRKGISIIELIDGHSSTIAQVLPLSTRDIKLAQ
NILFSGHSDLYANMRTELQRQLFLTKKGEMNTTIIEHLLSNDRITNY
SEQ ID NO: 4

Spo11-*Yarrowia lipolytica*
MDQDDTKAIINKTISRLKKQFHEDISSASIFETHASKGIPLTTLCGNSVNRFSIYLRLLQIIKSC
LDKDKITTKRDIYYDAVNLFKTQGVVDSCIARITNDFLQVPRDSLNVVAAQKGLIYSACDSALTI
SYKDDYRAPVTIPTHTTTLIPYTTNISDIQLAPQVNCILIVEKEAVFTTLCAYIPKDTLLITGKG
YPDHMTQDFVRLFDEMLPLFICVDADPHGIHIAATYRYRSFVRAPSLQGLGSSISYIGVSLVDFK
RGHLPLEDKNRKHAGRLLSAITGRQAEALELGDYIEMNKWKLELQRMLFLGKVAEMNVAGDGSEG
RNLARYIFDRIH SEQ ID NO: 5
Mei2-*Schizosaccharomyces pombe*
MIMETESPLSITSPSPSDSTFQVDMEKTMHALPSSLLDSPLLSTNEHYPPKSTLLLSGPSPIRNI
QLSATKSSESNSIDYLTDTQNIFPNFVNNENNYQFSTAPLNPIDACRVGERKVFTTGNVLLSADR
QPLSTWQQNISVLSESPPQNGIQSYISSSEQAAQALTRKPSVTGFRSSSLNSNSDDIDIFSHASR
YLFVTNLPRIVPYATLLELFSKLGDVKGIDTSSLSTDGICIVAFFDIRQAIQAAKSLRSQRFFND
RLLYFQFCQRSSIQKMINQGATIQFLDDNEGQLLLNMQGGSVLSILQLQSILQTFGPLLIMKPLR
SQNVSQIICEFYDTRDASFALDELDGRIIHNCCLQVAYYDAMADSVSTSSASSLSVPRGFSGMLN
NNSEWNNSMTMSSNQETPTAASCAVSRIGSSYGMSNNFGSVPLGRTESSPAWGTSGYYDVSSTSP
VAPSDRNPSRQYNSIRYGLDVNPIAPPNSSRLKQRNSDLLNGINPQWSPFSSNTGKVFDSPTGSL
GMRRSLTVGANASCSNPTNLSFASLTLHDSKADSTLSASSLNPDLNLQRYTPTVEKHASDRNSVD
YAQIASGIDTRTTVMIKNIPNKFTQQMLRDYIDVTNKGTYDFLYLRIDFVNKCNVGYAFINFIEP
QSIITFGKARVGTQWNVFHSEKICDISYANIQGKDRLIEKFRNSCVMDENPAYRPKIFVSHGPNR
GMEEPFPAPNNARRKLRSIASAQQIGLFPPTASKC SEQ ID NO: 6
Mei2 RNA binding motif 1-amino acids 195-270
RYLFVTNLPRIVPYATLLELFSKLGDVKGIDTSSLSTDGICIVAFFDIRQAIQAAKSLRSQRFFN
DRLLYFQFCQR SEQ ID NO: 7
Mei2 RNA binding motif 2-amino acids 596-692
RTTVMIKNIPNKFTQQMLRDYIDVTNKGTYDFLYLRIDFVNKCNVGYAFINFIEPQSIITFGKAR
VGTQWNVFHSEKICDISYANIQGKDRLIEKFR SEQ ID NO: 8
meiRNA-L
TAAATTATTGGACAGAATTGAGTTTCTTTCACTATGCATTGGAAATTCCTATAAATAGTCGATGA
AGTCTGCGAAACAAGGGAGGTAAACAGACTTAGTGGGTATTAAAATGTTGGTCAATCTTCTGCCG
TCTTGATTTAAAAGCACTTCTCTTTTACTATTGTAAGACGGAATATGCATGCAAGATCGCTTTAG
TTGGTTGAATGTCTCTTTCTTTGTGTTGTGGTTTGTTCGTTTTTTTCTAATTTGGAATATTATAA
GAAACGTTGTTTCTTGCAACATTTTGAAATGGTCATTCAAAAAGCTGGATTCGGTACCACTTTT
CTTTTTACCTTGTCTTCTAAGCTCTGTTAAATTTCTTGATGGGGTCCAGTTAAACCAACCCCCAA
GTTGGTTTATGTGAGCCTTGTCTCTTTTTTGGATGAATAGTAGCTTAGATAGTGATAGTTATTAT
TATGACTGATGGAATCTACTTAAAAATGGATTCCATTTTTTGTCTACTGTAATTGAATTCTTTTT
GGTACACTTTTTGGCTGCATTGTTATCCTTGAAAGCACTTACAATGTTTAAACTTTGCGAATGAC
TGAAACAGAAAAGAAATAAAACGACTGTACCTGAACTATTGTTGAAACAATATTAAAACGTATTC
CTGAAACAGATTAAACTACATTAAATTTTGTTAATGAATTAAACGTGAAACTTGAAAGTTTGATG
CGAAACAAAACCCGCAGTTTGTTTAAACGCTTATTTGTGATTAAAATTGATGAACCAGTTTAAAC
TATGAAAGTGTTTGAAAACGTGCTGAAACCATTCGTTAAACCCTGCAAACCAACATAAAAAAAAT
TGAAAATAAACAATAACCACAGCAAGCTAATTCAATTCCAACAATGGTATGTTGCATTGGTCTTC
GGTTGTGCTGTGCTCCCTCTTTTTTGAGCATAGTTAAAACCATTAATACTATTTAAACATTTCT
CTTTAAAAAAGAGAAGAGAATAGCAACACATAGAATTTCCAAATTCAACATGCCTTCAAATTTGA
AATCGCAAGGAACAGCTATTAATGAATGAAACGAGTTAAATTGAAATAAATCAAACACTATAAAG
ATTATTATTCTATTTCTTGCTTAAAACACACTTTAAGGAATTGAAATTTTTCACGTAAAATGTTG
ATGAACTGGCTTTAAATTTACATGCAAGTCTTGATTGTGAAATGATGCGTTGGAAGCATGAATTG
GTATTTTCTTTTTTAAAAAAAGCAATGAAAAGTTTGAAAAAGGCAATAAAACTTGGAGGTGGTTG
GACTTTGCCGATTTCACGAAGTTTTTCTTTGCTGTTTGAAACTCAACCAAATAAATTAAACAGTG
GTAGCAGCCCCAATTAAACTGAAAATCTATCAGTTATATGTTCATGAATGTGTAAAAGCAGCAGA
ACAGACAGATCCCAGCATTTTTCCCTTCTCTTTGCACTACATTATGAGAGGGATAACTGATATTC
TGTAATGTAGATCTGAGAAAACGAAGGCAAAGCTAATCCCGAATGTAAGGTTTAGGGAGCTACTT
GT SEQ ID NO: 9
meiRNA-S
TAAATTATTGGACAGAATTGAGTTTCTTTCACTATGCATTGGAAATTCCTATAAATAGTCGATGA
AGTCTGCGAAACAAGGGAGGTAAACAGACTTAGTGGGTATTAAAATGTTGGTCAATCTTCTGCCG
TCTTGATTTAAAAGCACTTCTCTTTTACTATTGTAAGACGGAATATGCATGCAAGATCGCTTTAG
TTGGTTGAATGTCTCTTTCTTTGTGTTGTGGTTTGTTCGTTTTTTTCTAATTTGGAATATTATAA
GAAACGTTGTTTCTTGCAACATTTTGAAATGGTCATTCAAAAAGCTGGATTCGGTACCACTTTT
CTTTTTACCTTGTCTTCTAAGCTCTGTTAAATTTCTTGATGGGGTCCAGTTAAACCAACCCCCAA
GTTGGTTTATGTGAGCCTTGTCTCTTTTTTGGATGAATAGTAGCTTAGATAGTGATAGTTATTAT
TATGACTGATGGAATCTACTTAAAAATGGATTCCATTTTTTGTCTACTGTAAT SEQ ID NO: 10
meiRNA-S, alternatively processed
TAAATTATTGGACAGAATTGAGTTTCTTTCACTATGCATTGGAAATTCCTATAAATAGTCGATGA
AGTCTGCGAAACAAGGGAGGTAAACAGACTTAGTGGGTATTAAAATGTTGGTCAATCTTCTGCCG
TCTTGATTTAAAAGCACTTCTCTTTTACTATTGTAAGACGGAATATGCATGCAAGATCGCTTTAG
TTGGTTGAATGTCTCTTTCTTTGTGTTGTGGTTTGTTCGTTTTTTTCTAATTTGGAATATTATAA
GAAACGTTGTTTCTTGCAACATTTTGAAATGGTCATTCAAAAAGCTGGATTCGGTACCACTTTT
CTTTTTACCTTGTCTTCTAAGCTCTGTTAAATTTCTTGATGGGGTCCAGTTAAACCAACCCCCAA
GTTGGTTTATGTGAGCCTTGTCTCTTTTTTGGATGAATAGTAGCTTAGATAGTGATAGTTATTAT
TATGACTGATGGAATCTACTTAAAAATGGATTCCATTTTTTGTCTACTGTAATTGAATTCTTTTT
GGTACACTTTTTGGCTGCATTGTTATCCTTGAAAGCACTTACAATGTTTAAACTTTGCGAAT SEQ ID NO: 11
Green Fluorescent protein (Accession number P42212)
mskgeelftg vvpilveldg dvnghkfsvs gegegdatyg kltlkfictt gklpvpwptl
vttfsygvqc fsrypdhmkq hdffksampe gyvqertiff kddgnyktra evkfegdtlv
nrielkgidf kedgnilghk leynynshnv yimadkqkng ikvnfkirhn iedgsvglad
hyqqntpigd gpvllpdnhy lstqsalskd pnekrdhmvl lefvtaagit hgmdelyk SEQ ID NO: 12
Murine GST (Accession No. CAA46155)
magkpvlhyf dgrgrmepir wllaaagvef eekflktrdd larlrsdgsl mfqqvpmvei
dgmklvqtka ilnyiaskyn lygkdmkera iidmytegva dleimilyyp hmppeekeas
lakikeqtrn ryfpafekvl kshgqdylvg nrlsradial vellyhveel dpgvvdnfpl
lkalrsrvsn lptvkkflqp gsqrkpfdda kcvesakkif s -continued

| SEQUENCES |
|---|

SEQ ID NO: 13
Maize GST (Accession No. ACG44016)
mattepaavr lvgsfaspfv hraevalrlk gvpyeliled lgnksellla hnpvhklvpv
llhgdraise slvileyvde afdgppllpa epharadarf wahfidqkfa rpfwmsfwtd
deerreamak eakenlalle aqlrgqrffg gealgfvdia acalahwvgv ieeaagvvlv
ggeefpalre wadayvndat vkqclrsrde lvdyfsarke myllraratp rs mterpsdlvv
nklvlfvvkg tatsthntvk plilleelgv phdiyvvekv sapwfseinp SEQ ID NO: 14
Saccharomyces GST (Accession No. EDN59492)
mkqkmiiydt pagpyparvr ialaeknmls svqfvrinlw kgehkkpefl aknysgtvpv
lelddgtlia ectaiteyid aldgtptltg ktplekgvih mmnkraelel ldpvsvyfhh
atpglgpeve lyqnkewglr qrdkalhgmh yfdtvlrerp yvagdsfsma ditviaglif
aaivklqvpe ecealrawyk rmqqrpsvkk lleirskss SEQ ID NO: 15
Aspergillus GST Accession No. GAQ03185)
mterpsdlvv nklvlfvvkg tatsthntvk plilleelgv phdiyvvekv sapwfseinp
hkmvpaildr spdsqdtlra weststlmyi adaydkdgtf ggrnvqerae innwltlhta
algptakywl yfyklhpekl pktieklrsn itvqydiler rlnepgqeyl alkdrpsiad
iatlpfamks taelfglefe rwpklqewsv rmsereavkr awqrvagfgh gekeygmlea SEQ ID NO: 16
Murine c-fos (Accession No. CAA24105)
mmfsgfnady easssrcssa spagdslsyy hspadsfssm gspvntqdfc adlsvssanf
iptvtaists pdlqwlvqpt lvssvapsqt raphpyglpt qsagayarag mvktvsggra
qsigrrgkve qlspeeeekr rirrernkma aakcrnrrre ltdtlqaetd qledeksalq
teianllkek eklefilaah rpackipddl gfpeemsvas ldltgglpea stpeseeaft
lplindpepk pslepvksis nvelkaepfd dflfpassrp sgsetsrsvp dvdlsgsfya
adweplhsns lgmgpmvtel eplctpvvtc tpgcttytss fvftypeads fpscaaahrk
gsssnepssd slssptllal SEQ ID NO: 17
Human c-fos (Accession No. CAA24756)
mmfsgfnady easssrcssa spagdslsyy hspadsfssm gspvnaqdfc tdlavssanf
iptvtaists pdlqwlvqpa lvssvapsqt raphpfgvpa psagaysrag vvktmtggra
qsigrrgkve qlspeeeekr rirrernkma aakcrnrrre ltdtlqaetd qledeksalq
teianllkek eklefilaah rpackipddl gfpeemsvas ldltgglpev atpeseeaft
lplindpepk psvepvksis smelktepfd dflfpassrp sgsetarsvp dmdlsgsfya
adweplhsgs lgmgpmatel eplctpvvtc tpsctaytss fvftypeads fpscaaahrk
gsssnepssd slssptllal SEQ ID NO: 18
Murine c-jun (Accession No. AAH94032)
mtakmettfy ddalnasflq sesgaygysn pkilkqsmtl nladpvgslk phlraknsdl
ltspdvgllk laspelerli iqssnghitt tptptqflcp knvtdeqegf aegfvralae
lhsqntlpsv tsaaqpvsga gmvapavasv agagggggys aslhseppvy anlsnfnpga
lssgggapsy gaaglafpsq pqqqqqppqp phhlpqqipv qhprlqalke epqtvpempg
etpplspidm esqerikaer krmrnriaas kcrkrkleri arleekvktl kaqnselast
anmlreqvaq lkqkvmnhvn sgcqlmltqq lqtf SEQ ID NO: 19
Human c-jun (Accession No. AAH06175)
mtakmettfy ddalnasflq sesgaygysn pkilkqsmtl nladpvgslk phlraknsdl
ltspdvgllk laspelerli iqssnghitt tptptqflcp knvtdeqegf aegfvralae
lhsqntlpsv tsaaqpvnga gmvapavasv aggsgsggfs aslhseppvy anlsnfnpga
lssgggapsy gaaglafpaq pqqqqqpphh lpqqmpvqhp rlqalkeepq tvpempgetp
plspidmesq erikaerkrm rnriaaskcr krkleriarl eekvktlkaq nselastanm
lreqvaqlkq kvmnhvnsgc qlmltqqlqt f SEQ ID NO: 20
Human mTOR (Accession No. AAI17167)
mlgtgpaaat taattssnvs vlqqfasglk srneetraka akelqhyvtm elremsqees
trfydqlnhh ifelvsssda nerkggilai asligveggn atrigrfany lrnllpsndp
vvmemaskai grlamagdtf taeyvefevk ralewlgadr negrrhaavl vlrelaisvp
tfffqqvqpf fdnifvavwd pkqairegav aalraclilt tqrepkemqk pqwyrhtfee
aekgfdetla ekegmnrddr ihgallilne lvrissmege rlreemeeit qqqlvhdkyc
kdlmgfgtkp rhitpftsfq avqpqqsnal vgllgysshq glmgfgtsps pakstlvesr
ccrdlmeekf dqvcqwvlkc rnsknsliqm tilnllprla afrpsaftdt qylqdtmnhv
lscvkkeker taafqalgll svavrsefkv ylprvldiir aalppkdfah krqkamqvda
tvftcismla ramgpgiqqd ikellepmla vglspaltav lydlsrqipq lkkdiqdgll
kmlslvlkhk plrhpgmpkg lahqlaspgl ttlpeasdvg sitlalrtlg sfefeghslt
qfvrhcadhf lnsehkeirm eaartcsrll tpsihlisgh ahvvsqtavq vvadvlskll
vvgitdpdpd irycvlasld erfdahlaqa enlqalfval ndqvfeirel aictvgrlss
mnpavfmpfl rkmliqilte lehsgigrik eqsarmlghl vnsaprlirp ymepilkali
lklkdpdpdp npgvinnvla tigelaqvsg lemrkwvdel fiiimdmlqd ssllakrqva -continued

| SEQUENCES |
|---| lwtlgqlvas tgyvvepyrk yptllevlln flkteqnqgt rreairvlgl lagldpykhk
vnigmidqsr dasavslses kssqdssdys tsemlvnmgn lpldefypav smvalmrifr
dqslshhhtm vvqaitfifk slglkcvqfl pqvmptflnv irvcdgaire flfqqlgmlv
sfvkshirpy medivtlmre fwvmntsiqs tiillieqiv valggefkly lpqliphmlr
vfmhdnspgr ivsikllaai qlfganlddy lhlllppivk lfdapeaplp srkaaletvd
rltesldftd yasriihpiv rtldqspelr stamdtlssl vfqlgkkyqi fipmvnkvlv
rhrinhqryd vlicrivkgy tladeeedpl iyqhrmlrsg qgdalasgpv etgpmkklhv
stinlqkawg aarrvskddw lewlrrlsle llkdssspsl rscwalaqay npmardlfna
afvscwseln edqqdelirs ielaltsqdi aevtqtllnl aefmehsdkg plplrddngi
vllgeraakc rayakalhyk elefqkgptp aileslisin nklqqpeaaa gvleyamkhf
geleiqatwy eklhewedal vaydkkmdtn kddpelmlgr mrclealgew gqlhqqccek
wtlvndetqa kmarmaaaaa wglgqwdsme eytcmiprdt hdgafyravl alhqdlfsla
qqcidkardl ldaeltamag esysraygam vschmlsele eviqyklvpe rreiirqiww
erlqgcqriv edwqkilmvr slvvsphedm rtwlkyaslc gksgrlalah ktlvlllgvd
psrqldhplp tvhpqvtyay mknmwksark idafqhmqhf vqtmqqqaqh aiatedqqhk
qelhklmarc flklgewqln lqginestip kvlqyysaat ehdrswykaw hawavmnfea
vlhykhqnqa rdekkklrha sganitnatt aattaatatt tastegsnse seaestensp
tpsplqkkvt edlskttllmy tvpavqgffr sislsrgnnl qdtlrvltlw fdyghwpdvn
ealvegvkai qidtwlqvip qliaridtpr plvgrlihql ltdigryhpq aliypltvas
kstttarhna ankilknmce hsntlvqqam mvseelirva ilwhemwheg leeasrlyfg
ernvkgmfev leplhammer gpqtlketsf nqaygrdlme aqewcrkymk sgnvkdltqa
wdlyyhvfrr iskqlpqlts lelqyvspkl lmcrdlelav pgtydpnqpi iriqsiapsl
qvitskqrpr kltlmgsngh efvfllkghe dlrqdervmq lfglvntlla ndptslrknl
siqryavipl stnsgligwv phcdtlhali rdyrekkkil lniehrimlr napdydhltl
mqkvevfeha vnntagddla kllwlkspss evwfdrrtny trslavmsmv gyilglgdrh
psnlmldrls gkikhidfgd cfevamtrek fpekipfrlt rmltnamevt gldgnyritc
htvmevlreh kdsvmavlea fvydpllnwr lmdtntkgnk rsrtrtdsys agqsveildg
velgepahkk tgttvpesih sfigdglvkp ealnkkaiqi inhvrdkltg rdfshddtld
vptqvellik qatshenlcq cyigwcpfw SEQ ID NO: 21
Mouse mTOR (Accession No. AII12905)
mlgtgpavat asaatssnvs vlqqfasglk srneetraka akelqhyvtm elremsqees
trfydqlnhh ifelvsssda nerkggilai asligveggn strigrfany lrnllpssdp
vvmemaskai grlamagdtf taeyvefevk ralewlgadr negrrhaavl vlrelaisvp
tfffqvqpf fdnifvavwd pkairegav aalraclilt tqrepkemqk pqwyrhtfee
aekgfdetla kekgmnrddr ihgallilne lvrissmege rlreemeeit qqqlvhdkyc
kdlmgfgtkp rhitptfsfq avqpqqpnal vgllgysspq glmgfgtsps pakstlvesr
ccrdlmeekf dqvcqwvlkc rssknsliqm tilnllprla afrpsaftdt qylqdtmnhv
lscvkkeker taafqalgll svavrsefkv ylprvldiir aalppkdfah krqktvqvda
tvvftcismla ramgpgiqqd ikellepmla vglspaltav lydlsrqipq lkkdiqdgll
kmlslvlmhk plrhpgmpkg lhaqlaspgl ttlpeasdva sitlalrtlg sfefeghslt
qfvrhcadhf lnsehkeirm eaartcsrll tpsihllisgh ahvvsqtavq vvadvlskll
vvgitdpdpd irycvlasld erfdahlaqa enlqalgval ndqvfeirel aictvgrlss
mnpafvmpfl rkmliqilte lehsgigrik eqsarmlghl vsnaprlirp ymepilkali
lklkdpdpdp npgvinnvla tigelaqvsg lemrkwvdel fiiimdlmqd ssllakrqva
lwtlgqlvas tgyvvepyrk yptllevlln flkteqnqgt rreairvlgl lgaldpykhk
vnigmidqsr dasavslses kssqdssdys tsemlvmngn lpldefypav smvalmrifr
dqslshhhtm vvqaitfifk slglkcvqfl pqvmptflnv irvcdgaire flfqqlgmlv
sfvkshirpy mdeivtlmre fwvmntsiqs tiillieqiv valggefkly lpqliphmlr
vfmhdnsqgr ivsikllaai qlfganlddy lhlllppivk lfdapevplp srkaaletvd
rltesldftd yasriihpiv rtldqspelr stamdtlssl vfqlgkkyqi fipmvnkvlv
rhrinhqryd vlicrivkgy tladeeedpl iyqhrmlrss qgdalasgpv etgpmkklhv
stinlqkawg aarrvskddw lewlrrlsle llkdssspsl rscwalaqay npmardlfna
afvscwseln edqqdelirs ielaltsqdi aevtqtllnl aefmehsdkg plplrddngi
vllgeraakc rayakhlhyk elefqkgptp aileslisin nklqqpeaas gvleyamkhf
geleiqatwy eklhewedal vaydkkmdtn kedpemmlgr nrclealgew gqlhqqccek
wtlvndetqa kmarmaaaaa wglgqwdsme eytcmiprdt hdgafyravl alhqdlfsla
qqcidkardl ldaeltamag esysraygam vschmlsele eviqyklvpe rreiirqiww
erlqgcqriv edwqkilmvr slvvsphedm rtwkkyaslc gksgrlalah ktlvlllgvd
psrqldhplp tahpqvtyay mknmwksark idafqhmqhf vqtmqqqaqh aiatedqqhk
qelhklmarc flklgewqln lqginestip kvlqyysaat ehdrswykaw hawavmnfea
vlhykhqnqa rdekkklrha sganitnatt aattaasaaa atstegsnse seasnensp
tpsplqkkvt edlsktllly tvpavqgffr sislsrgnnl qdtlrvltlw fdyghwpdvn
ealvegvkai qidtwlqvip qliaridtpr plvgrlihql ltdigryhpq aliypltvas
kstttarhna ankilknmce hsntlvqqam mvseelirva ilwhemwheg leeasrlyfg
ernvkgmfev leplhammer gpqtlketsf nqaygrdlme aqewcrkymk sgnvkdltqa
wdlyyhvfrr iskqlpqlts lelqyvspkl lmcrdlelav pgtydpnqpi iriqsiapsl
qvitskqrpr kltlmgsngh efvfllkghe dlrqdervmq lfglvntlla ndptslrknl
siqryavipl stnsgligwv phcdtlhali rdyrekkkil lniehrimlr mapdydhltl
mqkvevfeha vnntagddla kllwlkspss evwfdrrtny trslavmsmv gyilglgdrh
psnlmldrls giklhidfgd cfevamtrek fpekipfrlt rmltnamevt gldgnyrttc
htvmevlreh kdsvmavlea fvydpllnwr lmdtntkgnk rsrtrtdsys agqsveildg
velgepahkk agttvpesih sfigdglvkp ealnkkaiqi inrvrdkltg rdfshddtld
vptqvellik qatshenlcq ciygwcpfw -continued

SEQUENCES

SEQ ID NO: 22
Human FK506 binding protein 1A, 12 kDa (Accession No. AAP35729)
mgvqvetisp gdgrtfpkrg qtcvvhytgm ledgkkfdss rdrnkpfkfm lgkqevirgw
eegvaqmsvg qrakltispd yaygatghpg lipphatlvf dvellkle SEQ ID NO: 23
Mouse FK506 binding protein 1A, 12 kDa (Accession No. AAH04671)
mgvqvetisp gdgrtfpkrg qtcvvhytgm ledgkkfdss rdrnkpfkft lgkqevirgw
eegvaqmsvg qrakliissd yaygatghpg iipphatlvf dvellkle SEQ ID NO: 24
iTEV-1 (Accession No. P13299)
mksgiyqikn tlnnkvyvgs akdfekrwkr hfkdlekgch ssiklqrsfn khgnvfecsi
leeipyekdl iierenfwik elnskingyn iadatfgdtc sthplkeeii kkrsetvkak
mlklgpdgrk alyskpgskn grwnpethkf ckcgvriqts aytcskcrnr sgennsffnh
khsditkski sekmkgkkps nikkiscdgv ifdcaadaar hfkissglvt yrvksdkwnw
fyina SEQ ID NO: 25
iSceI (Accession No. P03882)
mkniknknqvm nlgpnskllk eyksqlieln iegfeagigl ilgdayirsr degktycmqf
ewknkaymdh vcllydqwvl spphkkervn hlgnlvitwg aqtfkhqafn klanlfivnn
kktipnnlve nyltpmslay wfmddggkwd ynknstnksi vlntqsftfe eveylvkglr
nkfqlncyvk inknkpiiyi dsmsylifyn likpylipqm myklpntiss etflk SEQ ID NO: 26
FokI (Accession No. P14870)
mflsmvskir tfgwvqnpgk fenlkrvvqv fdrnskvhne vknikiptlv keskiqkelv
almnqhdliy tykelvgtgt sirseapcda iiqatiadqg nkkgyidnws sdgflrwaha
lgfieyinks dsfvitdvgl ayskdasga iekeilieal ssyppairil tlledgqhlt
kfdlgknlgf sgesgftslp egilldtlan ampkdkgeir nnwegssdky armiggwldk
lglvkqgkke fiiptlgkpd nkefishafk itgeglkvlr rakgstkftr vpkrvyweml
atnltdkeyv rtrralilei likagslkie qiqdnlkklg fdevietien dikglintgi
fieikgrfyq lkdhilqfvi pnrgvtkqlv kseleekkse lrhklkyvph eyielielar
nstqdrilem kvmeffmkvy gyrgkhlggs rkpdgaiytv gspidygviv dtkaysggyn
lpigqademq ryveenqtrn khinpnewwk vypssvtefk flfvsghfkg nykaqltrln
hitncngavl sveelligge mikagtltle evrrkfnnge inf SEQ ID NO: 27
HO (Accession No. P09932)
mlsenttilm angeikdian vtansyvmca dgsaarvinv tqgyqkiyni qqktkhrafe
gepgrldprr rtvyqrlalq ctaghklsvr vptkplleks grnatkykvr wrnlqqcqtl
dgriiiipkn hhktfpmtve gefaakrfie emerskgeyf nfdievrdld yldaqlriss
cirfgpvlag ngvlskfltg rsdlvtpavk smawmlglwl gdsttkepei svdsldpklm
eslrenakiw glyltvcddh vplrakhvrl hygdgpdenr ktrnlrknnp fwkavtilkf
krdldgekqi pefmygehie vreaflagli dsdgyvvkkg egpesykiai qtvyssimdg
ivhisrslgm satvttrsar eeiiegrkvq cqftydcnva ggttsqnvls ycrsghktre
vppiikrepv yfsftddfqg estvygltie ghknfllgnk ievkscrgcc vgeqlkisqk
knlkhcvacp rkgikyfykd wsgknrvcar cygrykfsgh hcinckyvpe arevkkakdk
geklgitpeg lpvkgpecik cggilqfdav rgphkscgnn agaric SEQ ID NO: 28
oCME010
GTTAAGATTTACCCTTCTCCAGAGACAATCGAAATCATTAAGGACAAATACAGACAGAAAGAACA
TTTGGTGCAACATGGTGTTGCAGTTGCAGACTCTGTTAGCGTTGAAAGCACCGAGACAGCATTGC
AAAATGTTGGTTTGAAATTTGGTTTCCCATTTATGCTGAAGTCCAAAACTGTTTCTCCCTTCCCT
GATAG SEQ ID NO: 29
oCME011
AAAAACATTTCTACACCAAAAATGCCTGCACCTGGAAAAGTAGAAACCGCCTTTTTAGCTAAAAG
GTTGGCCTTTGTTTGAATAGTATCATTCACTCTTGCAGGTGCGTAAACAGTATGACAGATATTAT
CCTTGTGGATCGTTTCAACGGTTGGATAAGAGAAAATTTCTCCATCCAAGATACGCGGAACAATC
AATCG SEQ ID NO: 30
oCME012
TTTATTACCTGACGGTGAACTGTTAATCAATGAAATTGCACCAAGACCTCACAATTCTGGCCATT
ATACGATTGATGCTTGCGTCACTTCTCAGTTTGAAGCACATATTAGAGCTATTTCTGGATTGCCT
ATGCCCAAAAATTTTACTTGCTTTTCTACTCCCCAAACAAATGCCATTATGTTTCTCCCTTCCCT
GATAG SEQ ID NO: 31
oCME013
ACTTCTTTAAGATATTACAACCAGCAGACATGACAGGTAAATCCGAATCTGAACCCATTATAACA
CCCACTAATGGAGCTTTAGAGGTGCCTGAAACCGCATTTTCTGTTGATTTTGTTATCGGAAGGCC

SEQUENCES

ACCAGAGCCCTCAATGTATGCAAGTTTACGTTCACAATCAGACATAGAAGATACGCGGAACAATC
AATCG

SEQ ID NO: 32
oCME014
TGCTTGCGTCACTTCTCAGTTTGAAGCACATATTAGAGCTATTTCTGGATTGCCTATGCCCAAAA
ATTTTACTTGCTTTTCTACTCCCCAAACAAATGCCATTATGCTCAATATTTTAGGGTCTGATGTG
CCAAATGGCGAACTTGAACTTTGTAGAAGAGCACTTGAAACTACAAGCGCGTTTCTCCCTTCCCT
GATAG

SEQ ID NO: 33
oCME015
CCTCAATCGCATACTTGGCCATCCTTTGTGGGGTTCTATGTGCTGACACAATGGTGACTTCAAAC
GGAACACCAAACTTCTTTAAGATATTACAACCAGCAGACATGACAGGTAAATCCGAATCTGAACC
CATTATAACACCCACTAATGGAGCTTTAGAGGTGCCTGAAACCGCATTAGATACGCGGAACAATC
AATCG

SEQ ID NO: 34
Guide #1
CACAAAACACACAAACAAACACATGCTAGCCAGAGAAGCATTAGAAGTTTGCAGAATAGACGTTTATATGCAGATAAACAGA
CTTAGTGGGTATTAAAATGTTGGTCAATCTTCTGCCGTCTTGATTTAAAAGCACTTCTCTTTTAC
TATTGTAAGACGGAATATGCATGCAAGATCGCTTTAGTTGGTTGAATGTCTCTTTCTTTGTGTTG
TGGTTTGTTCGTTTTTTTCTAATTTGGAATATTATAAGAAACGTTGTTTTCTTGCAACATTTTGA
AATGGTCATTCAAAAAGCTGGATTCGGTACCACTTTTCTTTTTACCTTGTCTTCTAAGCTCTGTT
AAATTTCTTGATGGGGTCCAGTTAAACCAACCCCCAAGTTGGTTTATGTGAGCCTTGTCTCTTTT
TTGGATGAATAGTAGCTTAGATAGTGATAGTTATTATTATGACTGATGGAATCTACTTAAAAATG
GATTCCATTTTTTGTCTACTGTAATTGAATTCTTTTTGGTACACTTTTTGGCTGCATTGTTATCC
TTGAAAGCACTTACAATGTTTAAACTTTGCGAATGACTGAAACAGAAAAGAAATAAAACGACTGT
ACCTGAACTATTGTTGAAACAATATTAAAACGTATTCCTGAAACAG SEQ ID NO: 35
Guide #2

SEQ ID NO: 36
Guide #3

What is claimed is:

1. A system for editing of a target sequence at a locus of a host cell, comprising:
   i) a first isolated nucleic acid molecule comprising a nucleic acid segment comprising or encoding a targeting RNA sequence;
   ii) a second isolated nucleic acid molecule comprising a nucleic acid segment comprising or encoding a RNA segment that binds a protein having at least 80% amino acid sequence identity to SEQ ID NO:5;
   iii) a third isolated nucleic acid molecule comprising a nucleic acid segment encoding an endonuclease or a portion thereof with nuclease activity, or an isolated polypeptide comprising the endonuclease or the portion thereof;
   iv) a fourth isolated nucleic acid molecule comprising a nucleic acid segment encoding the protein having at least 80% amino acid sequence identity to SEQ ID NO:5 or a portion thereof that binds the RNA segment, or an isolated polypeptide comprising the protein having at least 80% amino acid sequence identity to SEQ ID NO:5 or the portion thereof that binds the RNA segment; and
   v) an isolated double stranded DNA molecule comprising DNA comprising at least one nucleotide sequence that is capable of binding to the target sequence at the locus.

2. The system of claim 1 wherein the first isolated nucleic acid molecule, the second isolated nucleic acid molecule, the third isolated nucleic acid molecule or the fourth isolated nucleic acid molecule, or any combination thereof, is/are integrated into the host cell genome.

3. The system of claim 2 wherein the third isolated nucleic acid molecule or the fourth isolated nucleic acid molecule, or both, is/are integrated into the host cell genome.

4. The system of claim 1 wherein the first isolated nucleic acid molecule, the second isolated nucleic acid molecule, the third isolated nucleic acid molecule or the fourth nucleic acid molecule, or any combination thereof, is/are on one or more isolated vectors.

5. The system of claim 1 wherein the nucleic acid segment in the first isolated nucleic acid molecule, the second isolated nucleic acid molecule, the third isolated nucleic acid molecule or the fourth isolated nucleic acid molecule is operably linked to an inducible promoter or enhancer.

6. The system of claim 1 wherein the first isolated nucleic acid molecule is fused to the second isolated nucleic acid molecule.

7. The system of claim 6 wherein the first isolated nucleic acid molecule is 5' to the second isolated nucleic acid molecule.

8. The system of claim 6 wherein the first isolated nucleic acid molecule is 3' to the second isolated nucleic acid molecule.

9. The system of claim 1 wherein the first isolated nucleic acid molecule and the second isolated nucleic acid molecule each further comprise complementary sequences at the 3' end and 5' end, respectively.

10. The system of claim 1 wherein the RNA segment that binds the protein having at least 80% amino acid sequence identity to SEQ ID NO:5 or the portion thereof, has at least about 80% nucleotide sequence identity to one of SEQ ID NOs:8-10.

11. The system of claim 1 wherein the endonuclease comprises Spo11, i-TEV1, i-SceI, HO, or FokI.

12. The system of claim 1 wherein the third isolated nucleic acid molecule is fused to the fourth isolated nucleic acid molecule, so as to encode a fusion protein having the endonuclease or the portion thereof fused to the protein having at least 80% amino acid sequence identity to SEQ ID NO:5 or the portion thereof.

13. The system of claim 1 wherein the endonuclease or the portion thereof is fused to a first protein that binds to a second protein, wherein the protein having at least 80% amino acid sequence identity to SEQ ID NO:5 or the portion thereof is fused to the second protein, wherein the first protein and the second protein bind to each other.

14. The system of claim 13 wherein the first protein or the second protein comprises GFP, GST, c-fos, c-jun, a protein that binds SH2 or SH3 domains, FRB, or FKBP12.

15. The system claim 1 wherein the DNA in the isolated double stranded DNA molecule comprises at least two different nucleotide sequences that are each capable of binding to the target sequence at the locus.

16. The system of claim 15 wherein at least one of the two different nucleotide sequences has less than 100% nucleotide sequence identity with the target sequence at the locus.

17. The system of claim 15 wherein the two different nucleotide sequences in the DNA in the isolated double stranded DNA molecule are separated by a non-target specific sequence.

18. The system of claim 15 wherein the two corresponding different nucleotide sequences at the locus are not contiguous with each other.

19. The system of claim 18 wherein the two nucleotide sequences in the DNA in the isolated double stranded DNA molecule are contiguous.

20. The system of claim 1 wherein the at least one nucleotide sequence in the DNA in the isolated double stranded DNA molecule has one or more nucleotide substitutions, insertions or deletions relative to the target sequence.

* * * * *